(12) United States Patent
Rathwell et al.

(10) Patent No.: US 10,052,373 B2
(45) Date of Patent: Aug. 21, 2018

(54) **PROTEIN AND PEPTIDE-FREE SYNTHETIC VACCINES AGAINST *STREPTOCOCCUS PNEUMONIAE* TYPE 3**

(71) Applicant: MAX-PLANCK-GESELLSCHAFT ZUR FÖRDERUNG DER WISSENSCHAFTEN E.V., Munich (DE)

(72) Inventors: Dominea Rathwell, Gyeonggi-do (KR); Sharavathi Guddehalli Parameswarappa, Berlin (DE); Subramanian Govindan, Tamil Nadu (IN); Chakkumkal Anish, The Hague (NL); Claney Lebev Pereira, Berlin (DE); Peter H. Seeberger, Klein Machnow (DE); Felix Bröcker, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 4 days.

(21) Appl. No.: 15/022,708

(22) PCT Filed: Sep. 18, 2014

(86) PCT No.: PCT/EP2014/069947
§ 371 (c)(1),
(2) Date: Mar. 17, 2016

(87) PCT Pub. No.: WO2015/040140
PCT Pub. Date: Mar. 26, 2015

(65) Prior Publication Data
US 2016/0279224 A1    Sep. 29, 2016

(30) Foreign Application Priority Data

Sep. 18, 2013 (EP) .................................. 13185039

(51) Int. Cl.
| | | |
|---|---|---|
| A61K 39/09 | (2006.01) | |
| A61K 47/54 | (2017.01) | |
| A61K 47/55 | (2017.01) | |
| A61K 47/61 | (2017.01) | |
| A61K 39/00 | (2006.01) | |

(52) U.S. Cl.
CPC ............ *A61K 39/092* (2013.01); *A61K 47/54* (2017.08); *A61K 47/543* (2017.08); *A61K 47/545* (2017.08); *A61K 47/549* (2017.08); *A61K 47/55* (2017.08); *A61K 47/61* (2017.08); *A61K 2039/55555* (2013.01); *A61K 2039/575* (2013.01); *A61K 2039/6012* (2013.01); *A61K 2039/6087* (2013.01)

(58) Field of Classification Search
CPC ........ A61K 47/48092; A61K 47/48061; A61K 47/48023; A61K 47/4823; A61K 2039/55555

USPC .......................................................... 536/55.1
See application file for complete search history.

(56) References Cited

U.S. PATENT DOCUMENTS

| | | | |
|---|---|---|---|
| 7,771,726 B2 | 8/2010 | Tsuji et al. | |
| 2008/0305127 A1* | 12/2008 | Poolman | A61K 39/092 424/194.1 |

FOREIGN PATENT DOCUMENTS

| | | |
|---|---|---|
| WO | WO 2006027685 | 3/2006 |
| WO | WO 2007/051004 | 5/2007 |
| WO | WO 2013/139803 | 9/2013 |

OTHER PUBLICATIONS

Communication under Rule 71(3) EPC dated Jun. 23, 2017 for EP Application No. 14776605.9, filed Sep. 18, 2014.
Invitation pursuant to Article 94(3) and Rule 71(1) EPC dated Apr. 12, 2017 for EP Application No. 14776605.9, filed Sep. 18, 2014.
AlonsoDeVelasco et al., "*Streptococcus pneumoniae*: Virulence Factors, Pathogenesis, and Vaccines" Microbiological Reviews (1995) 59(4):591-603.
Bai et al., "Natural kilter T (NKT)-B-cell interactions promote prolonged antibody responses and long-term memory to pneumococcal capsular polysaccharides" PNAS (2013) 110(40):16097-16102.
Campbell et al., "A Simplified Route to the (R)-Garner Aldehyde and (S)-Vinyl Glycinol" Synthesis (1998) 1998(12):1707-1709.
Cavallari et al., "A semisynthetic carbohydrate-lipid vaccine that protects against *S. pneumoniae* in mice" Nature Chemical Biology (2014) 10:950-956 (including online methods).
Kim et al., "Practical Synthesis of KRN7000 from Phytosphingosine" Synthesis (2004) 2004(6):847-850.
Lefeber et al., "Synthesis of *Streptococcus pneumoniae* Type 3 Neoglycoproteins Varying in Oligosaccharide Chain Length, Loading and Carrier" Chem. Eur. J. (2001) 7(20):4411-4421.
Li et al., "Design of a potent CD1d-binding NKT cell ligand as a vaccine adjuvant" PNAS (2010) 107(29):13010-13015.
Zhou et al., "Synthesis and NKT Cell Stimulating Properties of Fluorophore- and Biotin-Appended 6"-Amino-6"-deoxy-galactosylceramides" Org. Lett. (2002) 4(8):1267-1270.
International Search Report and Written Opinion dated Dec. 9, 2014 for PCT Application No. PCT/EP2014/069947, filed Sep. 18, 2014.

* cited by examiner

*Primary Examiner* — Shaojia Anna Jiang
*Assistant Examiner* — Michael C Henry
(74) *Attorney, Agent, or Firm* — Knobbe, Martens, Olson & Bear, LLP

(57) ABSTRACT

The present invention provides a protein- and peptide-free conjugate comprising a synthetic carbohydrate and a carrier molecule, wherein the synthetic carbohydrate is a *Streptococcus pneumoniae* type 3 capsular polysaccharide related carbohydrate and the carrier molecule is a glycosphingolipid. Said conjugate and pharmaceutical composition thereof are useful for immunization against diseases associated with *Streptococcus pneumoniae*, and more specifically against diseases associated with *Streptococcus pneumoniae* type 3.

18 Claims, 6 Drawing Sheets a b

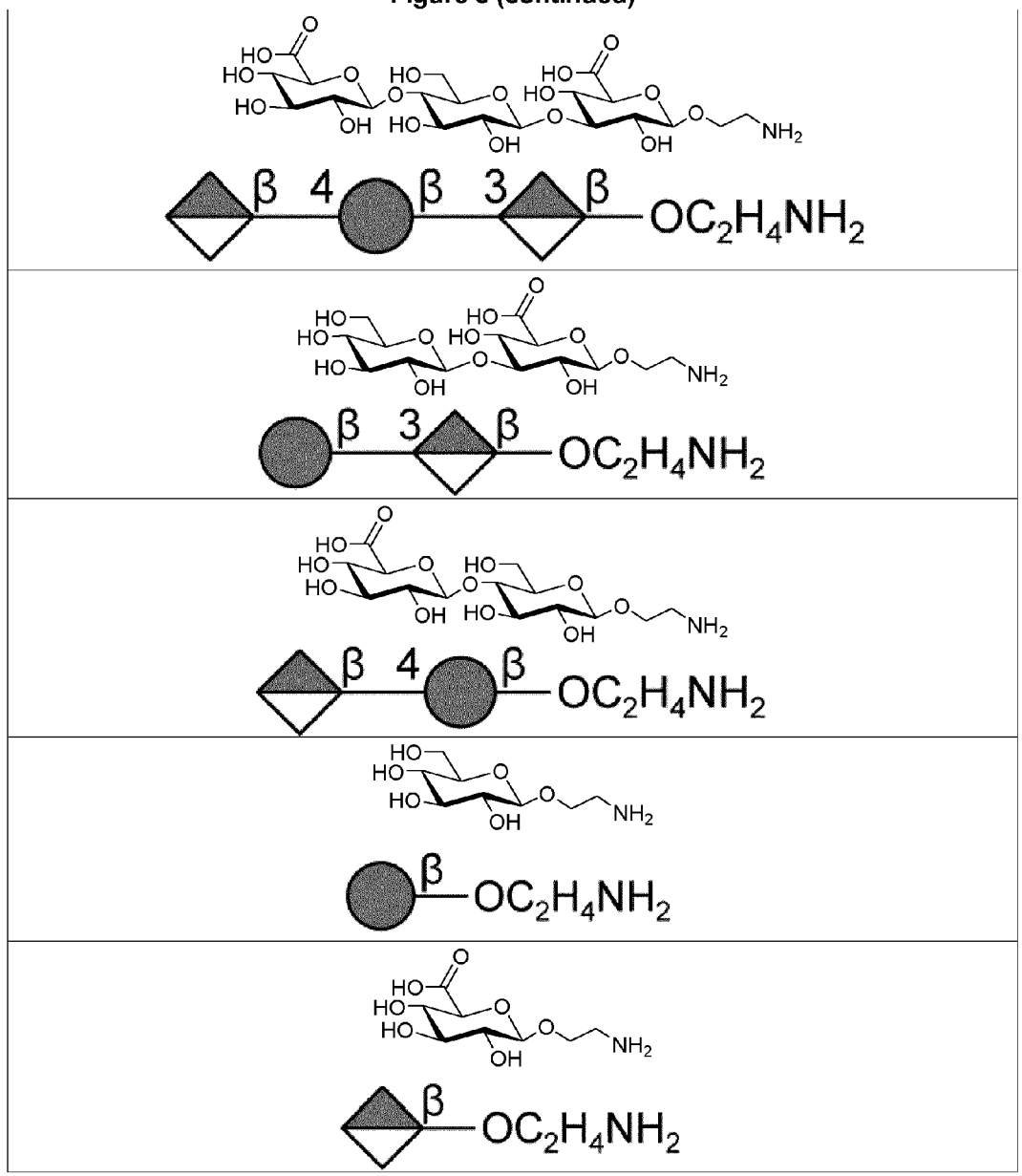

b.

c.

IgG3

0     1     2     Weeks d.

e.

PROTEIN AND PEPTIDE-FREE SYNTHETIC VACCINES AGAINST *STREPTOCOCCUS PNEUMONIAE* TYPE 3

FIELD OF THE INVENTION

The present invention provides a protein- and peptide-free conjugate comprising a synthetic carbohydrate and a carrier molecule, wherein the synthetic carbohydrate is a *Streptococcus pneumoniae* type 3 capsular polysaccharide related carbohydrate and the carrier molecule is a glycosphingolipid. Said conjugate and pharmaceutical composition thereof are useful for prevention and/or treatment of diseases associated with *Streptococcus pneumoniae*, and more specifically of diseases associated with *Streptococcus pneumoniae* type 3.

BACKGROUND OF THE INVENTION

Vaccination is a powerful tool for improving human health. By contributing to the education of the immune system, vaccination has pioneered the fight against infectious diseases caused by pathogens such as bacteria.

*Streptococcus pneumoniae* is a Gram-positive bacterium and one of the main pathogens causing invasive diseases. 90 serotypes of *Streptococcus pneumoniae* have been identified based on difference in their core capsular polysaccharides (CPS) structures consisting of polymer of repeating oligosaccharides units, which are the virulent factor of the bacteria. *Streptococcus pneumoniae* type 3 (SP3) is part of the current pneumococcal vaccines consisting of isolated CPS (PPV-23 valent and PCV-13 valent). The capsular polysaccharide (CPS) of SP3 consists of [→3)-β-D-GlcpA-(1→4)-β-D-Glcp-(1→] repeating units. The commercially available 23-valent pneumococcal polysaccharide vaccine (PPV) contains purified capsular polysaccharide (CPS) antigens of 23 serotypes. However, this vaccine is not effective in the case of infants and young children. PCV-13 contains immunogenic conjugates comprising the purified polysaccharides of 13 different *S. pneumoniae* serotypes covalently linked to a protein, such as $CRM_{197}$.

The currently marketed vaccines are effective in North America and Europe for individuals of a particular age. The manufacturing process for these vaccines is complex and results in a higher price. Therefore, the vaccine is unaffordable in most developing countries.

The glycosphingolipid α-galactosylceramide, also known as KRN7000, is a synthetic derivative of a glycolipid found in marine sponges, and identified as an immune activator that lowered the tumor burden of mice. This glycosphingolipid is known to be presented by antigen-presenting cells (APCs) by loading it unto the protein CD1d. After being loaded with the glycolipid, CD1d will interact with an invariant T-cell receptor (TCR) of invariant natural killer T cells (iNKT cells), resulting in the activation of the iNKT cells, expansion of their population, and secretion of a plethora of cytokines. A variety of α-galactosylceramide analogs able to stimulate iNKT cells were described in the literature (X. Li et al. *PNAS* 2010, 107, 29, 13010-13015). Also, αGalCer or analogs are being investigated in many contexts as vaccine adjuvants (U.S. Pat. No. 7,771,726 B2; WO 2006027685 A2). L. Bai et al. *PNAS*, 2013, 110, 40, 16097-16102 discloses that elevated IgM and IgG titers against pneumococcal capsular polysaccharide of SP14 are raised by immunizing mice with liposomes co-expressing the tetrasaccharide repeating unit of *S. pneumoniae* capsular polysaccharide serotype 14 linked to diacylglycerol and the NKT ligand PBS57. WO 2007/051004 A2 provides a conjugate comprising α-galactosylceramide conjugated at C-2 position of the galactose moiety via a linker to p-hydroxy-m-nitro phenyl antigen (NP-α-GalCer). Immunization of mice with said conjugate stimulated a strong antibody response specific for NP. To the best of our knowledge, no work has focused on covalently linking a glycosphingolipid to a saccharidic antigen of defined length.

It is the objective of the present invention to provide peptide-free and protein-free fully synthetic conjugates of general formula (I) comprising a *Streptococcus pneumoniae* type 3 capsular polysaccharide related carbohydrate of defined length covalently linked to a glycosphingolipid and pharmaceutical compositions thereof, useful for prevention and/or treatment of diseases associated with *Streptococcus pneumoniae*, and more specifically of diseases associated with *Streptococcus pneumoniae* type 3. Said conjugates and compositions thereof are heat-resistant or heat-stable. Immunization with said conjugates results in the production of high titters of antibodies against pneumococcal capsular polysaccharide of SP3. The antibodies present opsonophagocytosis activity and bactericidal activity.

The objective of the present invention is solved by the teaching of the independent claims. Further advantageous features, aspects and details of the invention are evident from the dependent claims, the description, the figures, and the examples of the present application.

DESCRIPTION OF THE INVENTION

The present invention provides fully synthetic conjugates of general formula I

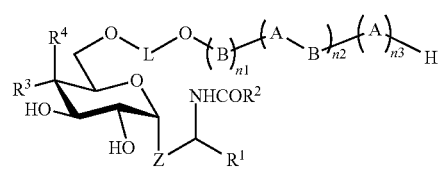

wherein
A is

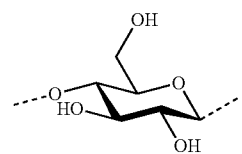

B is

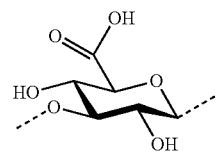

$R^1$ is selected from

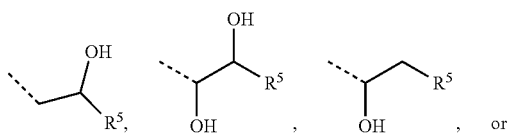

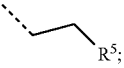

$R^2$ is $-(X^1)_{p1}-(X^2)_{p2}-(X^3)_{p3}-X^4$;

$R^3$ and $R^4$ are selected from —H and —OH and cannot be simultaneously —H or —OH;

$R^5$ is $-(Y^1)_{m1}-(Y^2)_{m2}-(Y^3)_{m3}-Y^4$;

Z represents $-O-CH_2-$, $-S-CH_2-$, $-CH_2-CH_2-$, $-O-CH_2-CH_2-$, $-CH_2-CH_2-CH_2-$, or $-CH_2-CH=CH-$;

$X^4$ represents: —H, -iPr, -tBu, -sBu,

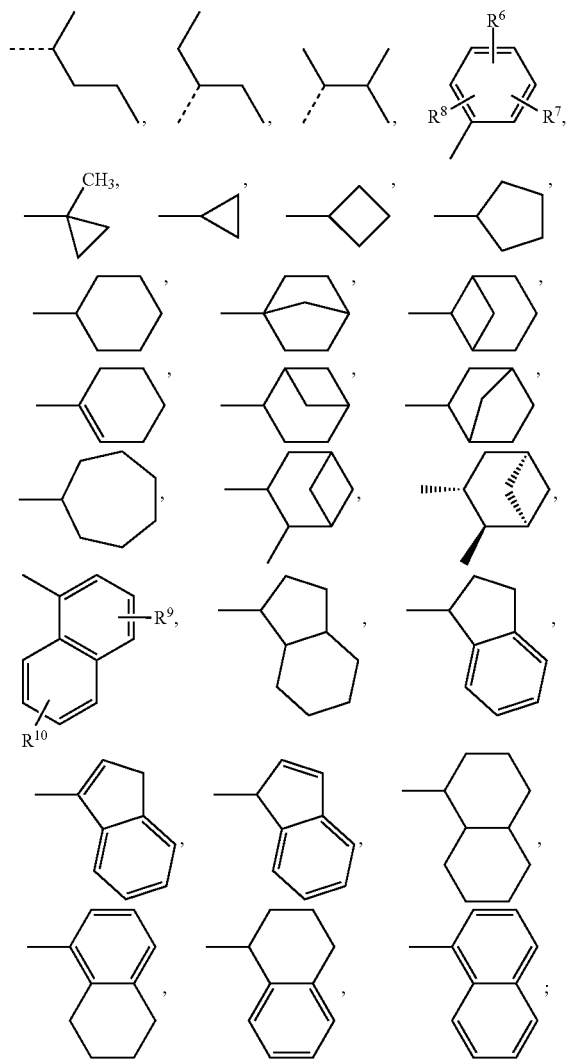

$Y^4$ is selected from: —H, -iPr, -tBu, -Ph, sBu,

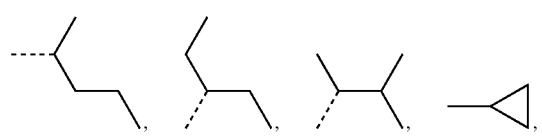

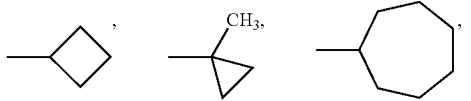

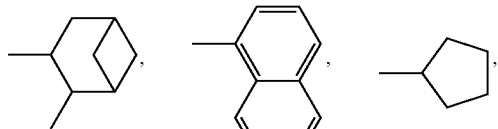

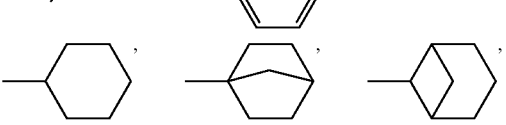

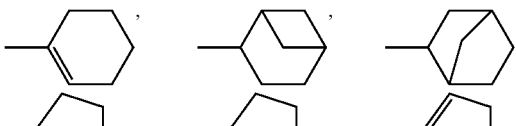

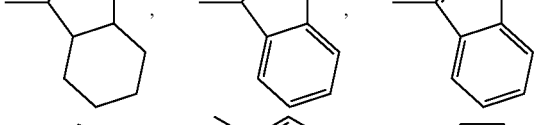

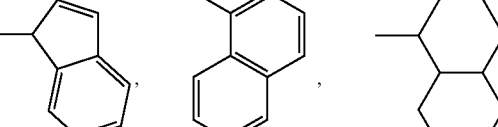

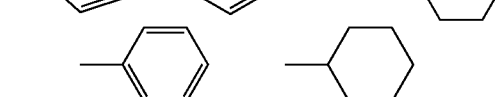

$X^1$, $X^2$, $X^3$, $Y^1$, $Y^2$ and $Y^3$ are independently of each other selected from:

$-CH_2-$, $-CH(OH)-$, $-CH(CH_3)-$, $-CH(C_2H_5)-$, $-CH(C_3H_7)-$, $-CH(C_4H_9)-$,

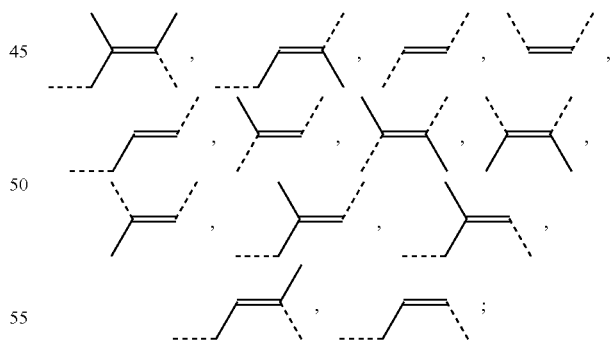

n2 is an integer selected from 1, 2, 3, 4, 5, 6, 7, 8, 9 and 10;

n1 and n3 represent independently of each other an integer selected from 0 and 1;

L represents -$L^1$-NH-$L^2$-NH-$L^3$-;

$L^1$ represents -$L^{1'}$-$L^{1''}$-$L^{1'''}$- or -$L^{1'}$-$L^{1''}$- or -$L^{1'}$-; and $L^3$ represents -$L^{3'}$-$L^{3''}$-$L^{3'''}$- or -$L^{3'}$-$L^{3''}$- or -$L^{3'}$-; and $L^{1'}$, $L^{1''}$, $L^{1'''}$, $L^{3'}$, $L^{3''}$ and $L^{3'''}$ are independently of each other selected from: $-CH_2-$, $-C_2H_4-$, $-C_3H_6-$, $-C_4H_8-$, $-C_5H_{10}-$, $-C_6H_{12}-$, $-C_7H_{14}-$, —$C_8H_{16}$—, —$C_9H_{18}$—, —$C_{10}H_{20}$—, —$CR^9R^{10}$—, —$CR^{11}R^{12}$—, —$CR^{13}R^{14}$—, —$CR^{15}R^{16}$—, —$CR^{17}R^{18}$—, —$CR^{19}R^{20}$—, —$(CH_2—CH_2—O)_o—CH_2—CH_2$—, —$(CH_2—CH_2—O)_o—CH_2$—, -o-$C_6H_4$—, -m-$C_6H_4$—, -p-$C_6H_4$—, —$CH_2—S—CH_2$—, —$CH_2—O—CH_2$—;

$L^2$ is selected from:

—C(O)—, -E-, —C(O)—NH—NH—C(O)—,

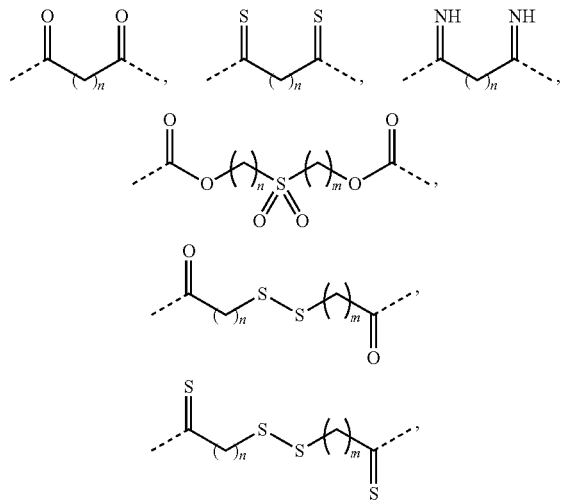

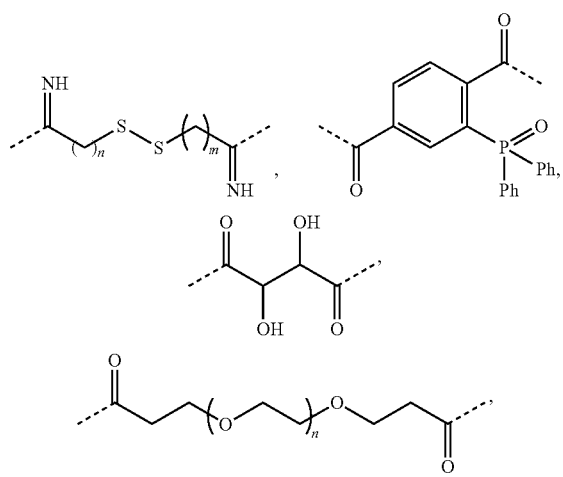

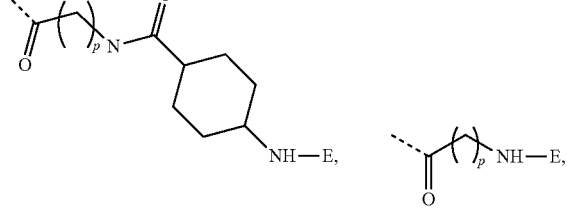

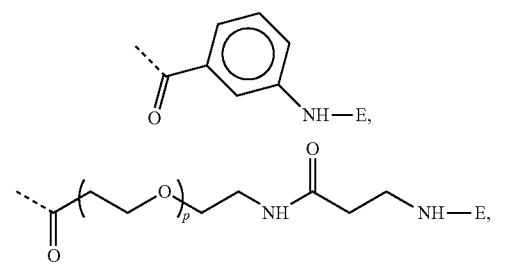

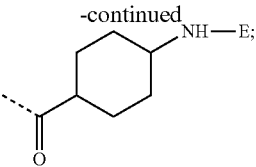

E is selected from

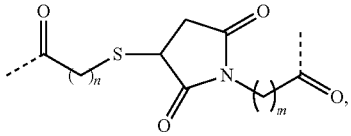

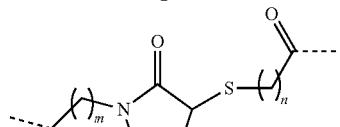

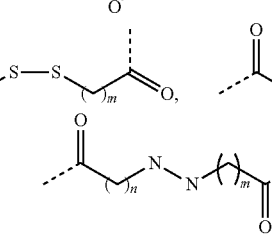

$R^6$, $R^7$ and $R^8$ are independently of each other selected from: —H, —$CH_3$, —$C_2H_5$, —$C_3H_7$, —$C_4H_9$, —$C_5H_{11}$, -Ph, —F, —Cl, —Br, —I, —$OCH_3$, —$OCF_3$, —$CF_3$;

$R^9$ to $R^{20}$ represent independently of each other —H, —$OCH_3$, —$OC_2H_5$, —$OC_3H_7$, cyclo-$C_3H_5$, cyclo-$C_4H_7$, cyclo-$C_5H_9$, cyclo-$C_6H_{11}$, cyclo-$C_7H_{13}$, cyclo-$C_8H_{15}$, -Ph, —$CH_2$-Ph, —$CPh_3$, —$CH_3$, —$C_2H_5$, —$C_3H_7$, —CH$(CH_3)_2$, —$C_4H_9$, —$CH_2$—CH$(CH_3)_2$, —CH$(CH_3)$—$C_2H_5$, —C$(CH_3)_3$, —$C_5H_{11}$, —CH$(CH_3)$—$C_3H_7$, —$CH_2$—CH$(CH_3)$—$C_2H_5$, —CH$(CH_3)$—CH$(CH_3)_2$, —C$(CH_3)_2$—$C_2H_5$, —$CH_2$—C$(CH_3)_3$, —CH$(C_2H_5)_2$, —$C_2H_4$—CH$(CH_3)_2$, —$C_6H_{13}$, —$C_3H_6$—CH$(CH_3)_2$, —$C_2H_4$—CH$(CH_3)$—$C_2H_5$, —CH$(CH_3)$—$C_4H_9$, —$CH_2$—CH$(CH_3)$—$C_3H_7$, —CH$(CH_3)$—$CH_2$—CH$(CH_3)_2$, —CH$(CH_3)$—CH$(CH_3)$—$C_2H_5$, —$CH_2$—CH$(CH_3)$—CH$(CH_3)_2$, —$CH_2$—C$(CH_3)_2$—$C_2H_5$, —C$(CH_3)_2$—$C_3H_7$, —C$(CH_3)_2$—CH$(CH_3)_2$, —$C_2H_4$—C$(CH_3)_3$, —CH$(CH_3)$—C$(CH_3)_3$, —$C_7H_{15}$, —$C_8H_{17}$, —$C_6H_4$—$OCH_3$, —$CH_2$—$CH_2$—$OCH_3$, —$CH_2$—$OCH_3$, —$CH_2$—$C_6H_4$—$OCH_3$;

p1, p2, p3, m1, m2 and m3 represent independently of each other an integer from 0 to 10;

m, n, o and p represent independently of each other an integer from 1 to 10;

and enantiomers, stereoisomeric forms, mixtures of enantiomers, anomers, diastereomers, mixtures of diastereomers, tautomers, hydrates, solvates and racemates of the above mentioned compounds and pharmaceutically acceptable salts thereof.

The compounds of the present invention bear acidic substituents and they may form salts with organic or inorganic bases. Examples for suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the conjugate of general formula I with a solution of base, selected out of the group mentioned above.

It is clear for the skilled person in the art of carbohydrate chemistry that the conjugates of general (I) are not containing —O—O— bonds and or sugar fragments (A, B) connected or bound to each other via their anomeric or C-1 carbons.

Surprisingly, it was found that the conjugates of general formula (I) presenting the SP3 capsular polysaccharide related carbohydrate of defined length at the C-6 position of the sugar moiety of the glycosphingolipid are able to provide a protective immune response against SP3 bacteria in a human and/or animal host. Said protective immune response against SP3 bacteria cannot be elicited by immunization with the conjugates presenting the SP3 capsular polysaccharide related carbohydrate at position 2, 3 or 4 of the sugar moiety of the glycosphingolipid.

Additionally, the conjugate of general formula (I) is able to elicit in mice serum IgG responses that are superior both in terms of kinetics and IgG2a and IgG3 production to the corresponding $CRM_{197}$ conjugate presenting the same SP3 capsular polysaccharide related carbohydrate. Antibodies elicited by the conjugate of general formula (I) are cross-reacting with the natural SP3 polysaccharide, thus indicating the ability of these antibodies to bind to *S. pneumoniae* serotype 3 bacteria and to confer protection against pneumococcal infection.

The conjugate of general formula (I) is fully synthetic i.e. both the *Streptococcus pneumoniae* type 3 capsular polysaccharide related carbohydrate of defined length and the glycosphingolipid are synthetically accessed. The fully synthetic SP3 capsular polysaccharide related carbohydrate enabled the identification of the most immunogenic epitope and the reproducibility of the antibody response from one batch to another. These achievements cannot be completed by employing SP3 capsular polysaccharide isolated from natural sources due to microheterogenicity problems.

A preferred embodiment according to the current invention is directed to conjugates of general formula I, wherein n1 is 0 and n3 is 1. Thus, conjugates of general formula IV

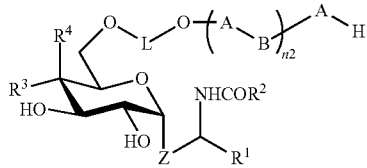

IV wherein

A is

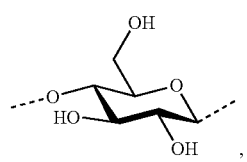

B is

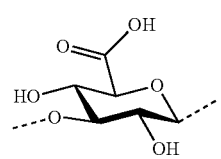

and $R^1$, $R^2$, $R^3$, $R^4$, Z, L and n2 have the meanings defined herein, are especially preferred.

Another embodiment of the present invention refers to conjugates of general formula I, wherein n1 is 1 and n3 is 0 or 1. Hence, conjugates of general formula V and VI wherein A, B, $R^1$, $R^2$, $R^3$, $R^4$, Z and n2 have the meanings defined herein are also preferred.

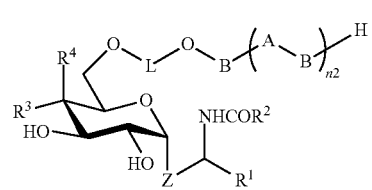

V

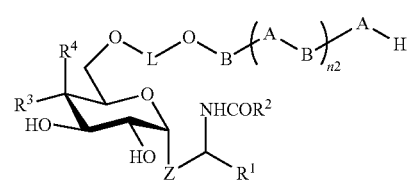

VI

Even more preferred conjugates of the present invention are conjugates of general formula I, wherein n1 and n3 are 0. Therefore, a particularly preferred embodiment of the invention is directed to conjugates of general formula VII, wherein A, B, $R^1$, $R^2$, $R^3$, $R^4$, Z and n2 have the meanings defined herein.

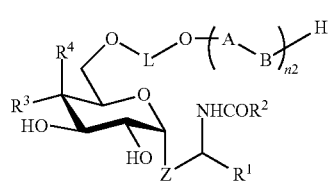

VII

The conjugates according to the current invention comprise a *Streptococcus pneumoniae* type 3 capsular polysaccharide related carbohydrate conjugated or connected to a glycosphingolipid. Preferably, the glycosphingolipid of the present invention contains as sugar moiety a α-galactoside. Therefore, a further embodiment of the present invention refers to a conjugate of general formula VIII,

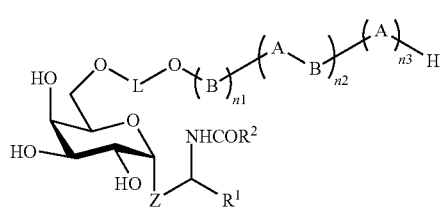

VIII wherein A, B, $R^1$, $R^2$, Z, n1, n2 and n3 have the meanings defined herein.

Conjugates of general formula IV, V, VI and VII, wherein $R^3$ is —H and $R^4$ is —OH are particularly preferred.

A further embodiment is directed towards conjugates of general formula I, IV, V, VI and VII, wherein $R^3$ is —OH and $R^4$ is —H, in other words, the glycosphingolipid presents an α-glucoside as sugar moiety.

Preferably, the Z residue is selected from —O—$CH_2$— or —O—$CH_2$—$CH_2$—; and $R^1$ residue represents

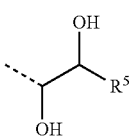

wherein $R^5$ has the meaning as defined herein.

In yet another preferred embodiment, the residue Z represents —$CH_2$—$CH_2$—$CH_2$—, or —$CH_2$—CH=CH—.

Other particularly preferred conjugates according to the current invention are conjugates of general formula IX,

IX

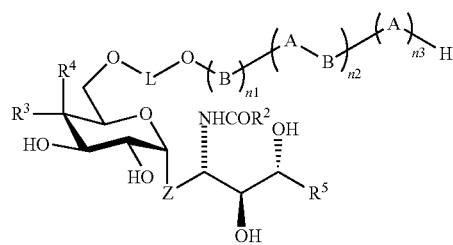

wherein A, B, $R^2$, $R^3$, $R^4$, $R^5$, Z, n1, n2 and n3 have the meanings defined herein.

The carbohydrate related to *Streptococcus pneumoniae* type 3 capsular polysaccharide is connected to the glycosphingolipid via a linker L, of general formula -$L^1$-NH-$L^2$-NH-$L^3$-, wherein the $L^2$ residue is preferably selected from:

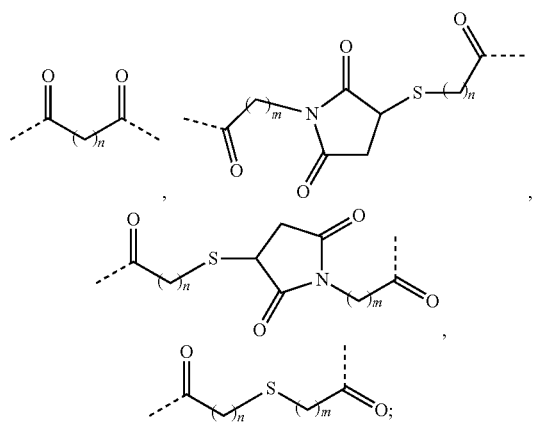

and m and n represent independently of each other an integer from 1 to 10.

Preferably, the $X^4$ residue is selected from:
—H, -iPr, -tBu,

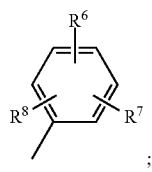

the $Y^4$ is selected from: —H, -iPr, -tBu, or -Ph; and the $X^1$, $X^2$, $X^3$, $Y^1$, $Y^2$, $Y^3$ residues are independently of each other selected from: —$CH_2$—, —CH(OH)—, —CH($CH_3$)—, —CH($C_2H_5$)—, —CH($C_3H_7$)—, —CH($C_4H_9$)—,

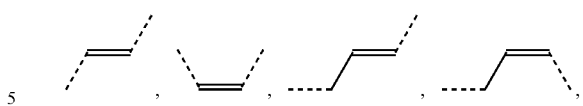

wherein the substituents $R^6$, $R^7$ and $R^8$ are independently of each other selected from: —H, —$CH_3$, —$C_2H_5$, —$C_3H_7$, —$C_4H_9$, —$C_5H_{11}$, -Ph, —F, —Cl, —Br, —I.

More preferably, the substituents $R^6$, $R^7$ and $R^5$ are independently of each other selected from —H, —F, —Cl, —Br, and —I.

Preferably, the chain —$(X^1)_{p1}$—$(X^2)_{p2}$—$(X^3)_{p3}$— of $R^2$ in general formula (I) contains maximum 25 carbon atoms. Thus, the chain —$(X^1)_{p1}$—$(X^2)_{p2}$—$(X^3)_{p3}$— of $R^2$ in general formula (I) contains preferably between 5 and 25 carbon atoms, more preferably between 7 and 25 carbon atoms and even more preferably between 9 and 25 carbon atoms.

Preferably, the chain —$(Y^1)_{m1}$—$(Y^2)_{m2}$—$(Y^3)_{m3}$— of $R^5$ in general formula (I) contains maximum 14 carbon atoms.

An embodiment of the present invention is directed to a conjugate of general formula (I-A)

I-A

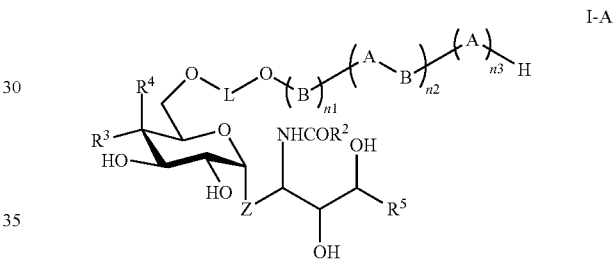

wherein

A is

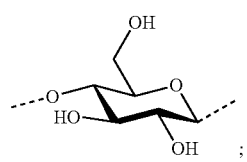

B is

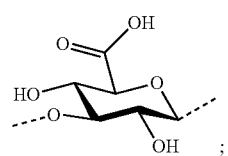

$R^2$ is —$(X^1)_{p1}$—$(X^2)_{p2}$—$(X^3)_{p3}$—$X^4$;

$R^3$ and $R^4$ are selected from —H and —OH and cannot be simultaneously —H or —OH;

$R^5$ is —$(Y^1)_{m1}$—$(Y^2)_{m2}$—$(Y^3)_{m3}$—$Y^4$;

Z represents: —O—$CH_2$—, —S—$CH_2$— or —$CH_2$—$CH_2$—;

$X^4$ represents: —H or

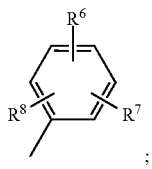
;

$Y^4$ represents: —H or -Ph;

$X^1$, $X^2$, $X^3$, $Y^1$, $Y^2$, and $Y^3$ are independently of each other selected from: —$CH_2$—,

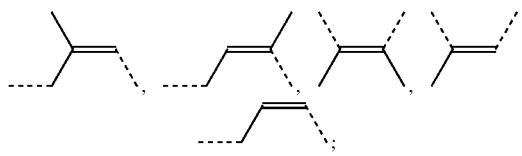
;

n2 is an integer selected from 1, 2, 3, 4, 5, 6, 7, 8, 9 and 10;

n1 and n3 represent independently of each other an integer selected from 0 and 1;

L represents $-L^1-NH-L^2-NH-L^3-$;

$L^1$ represents $-L^{1'}-L^{1''}-L^{1'''}-$ or $-L^{1'}-L^{1'''}-$ or $-L^{1'}-$; and $L^3$ represents $-L^{3'}-L^{3''}-L^{3'''}-$ or $-L^{3'}-L^{3'''}-$ or $-L^{3'}-$; and $L^{1'}$, $L^{1''}$, $L^{1'''}$, $L^{3'}$, $L^{3''}$, and $L^{3'''}$ are independently of each other selected from: —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —($CH_2$—$CH_2$—O$)_o$—$CH_2$—$CH_2$, —($CH_2$—$CH_2$—O$)_o$—$CH_2$—;

$L^2$ is selected from: —C(O)—,

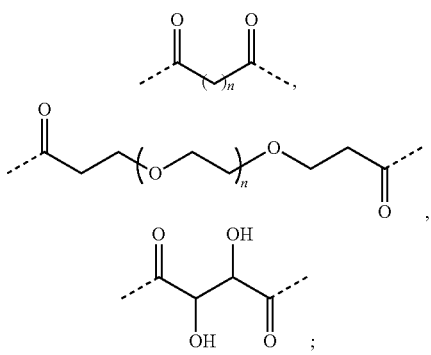
;

$R^6$, $R^7$ and $R^8$ are independently of each other selected from: —H, —$CH_3$, —$C_2H_5$, —F, —Cl, —Br, —$OCH_3$ and —$CF_3$;

n and o represent independently of each other an integer selected from 1, 2, 3, 4, 5 and 6;

p1, p2, p3, m1, m2 and m3 represent independently of each other an integer from 0 to 10.

Preferably, the chain —$(X^1)_{p1}$—$(X^2)_{p2}$—$(X^3)_{p3}$— of $R^2$ in general formula (I-A) contains maximum 25 carbon atoms and the chain —$(Y^1)_{m1}$—$(Y^2)_{m2}$—$(Y^3)_{m3}$— of $R^5$ in general formula (I) contains maximum 14 carbon atoms.

A conjugate of general formula (I-B)

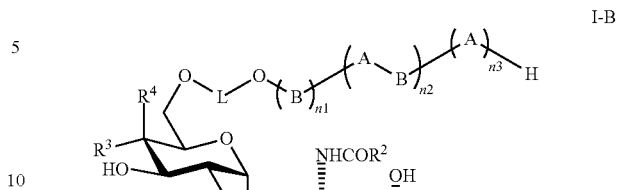

wherein

A is

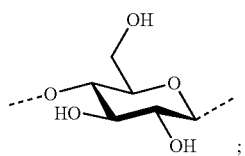
;

B is

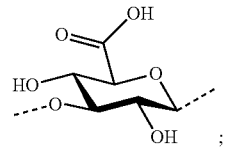
;

$R^2$ is —$(X^1)_{p1}$—$(X^2)_{p2}$—$(X^3)_{p3}$—$X^4$;

$R^3$ and $R^4$ are selected from —H and —OH and cannot be simultaneously —H or —OH;

$R^5$ is —$(Y^1)_{m1}$—$(Y^2)_{m2}$—$(Y^3)_{m3}$—$Y^4$;

$X^4$ represents: —H or

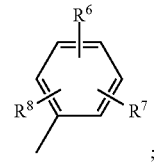
;

$Y^4$ represents: —H or -Ph;

$X^1$, $X^2$, $X^3$, $Y^1$, $Y^2$, and $Y^3$ are independently of each other selected from: —$CH_2$—, and

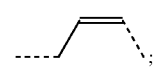
;

n2 is an integer selected from 1, 2, 3, 4, 5, 6, 7, 8, 9 and 10;

n1 and n3 represent independently of each other an integer selected from 0 and 1;

L represents $-L^1NH-L^2-NH-L^3-$;

$L^1$ represents $-L^{1'}-L^{1''}-L^{1'''}-$ or $-L^{1'}-L^{1'''}-$ or $-L^{1'}-$; and $L^3$ represents $-L^{3'}-L^{3''}-L^{3'''}-$ or $-L^{3'}-L^{3'''}-$ or $-L^{3'}-$; and $L^{1'}$, $L^{1''}$, $L^{1'''}$, $L^{3'}$, $L^{3''}$, and $L^{3'''}$ are independently of each other selected from: —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—;

$L^2$ is selected from: —C(O)—,

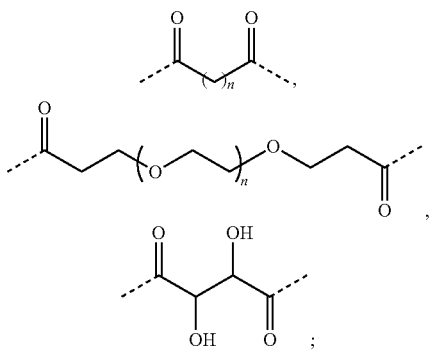

$R^6$, $R^7$ and $R^8$ are independently of each other selected from: —H, —$CH_3$, —$C_2H_5$, —F, —Cl, —Br, —$OCH_3$ and —$CF_3$;

n represents an integer selected from 1, 2, 3, 4, 5 and 6;

p1, p2, p3, m1, m2 and m3 represent independently of each other an integer from 0 to 10; is also preferred.

Preferably, residue $R^3$ represents —H and residue $R^4$ represents —OH. Thus, a conjugate of general formula (VIII) is preferred. Also preferred is a conjugate of general formula (I-A) or (I-B), wherein $R^3$ represents —H and residue $R^4$ represents —OH.

Another preferred conjugate according to the present invention is a conjugate of general formula (I-C)

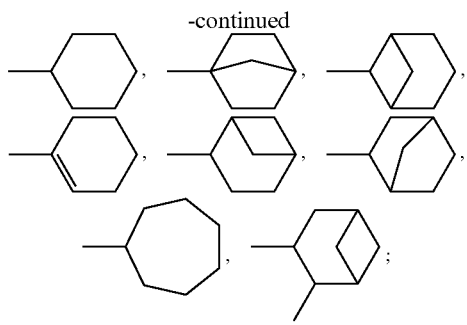

$Y^4$ is selected from: —H, -iPr, -tBu, -Ph, -sBu;

$X^1$, $X^2$, $X^3$, $Y^1$, $Y^2$, and $Y^3$ are independently of each other selected from: —$CH_2$—, —CH(OH)—, —CH($CH_3$)—, —CH($C_2H_5$)—, —CH($C_3H_7$)—, —CH($C_4H_9$)—,

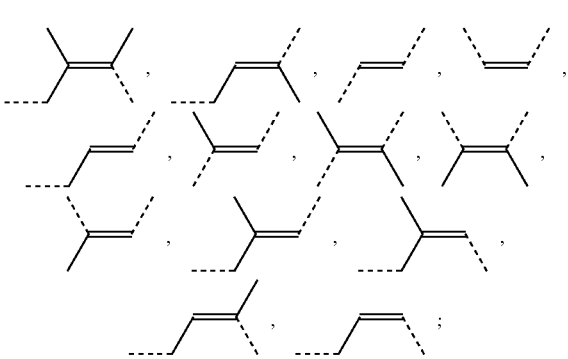

I-C

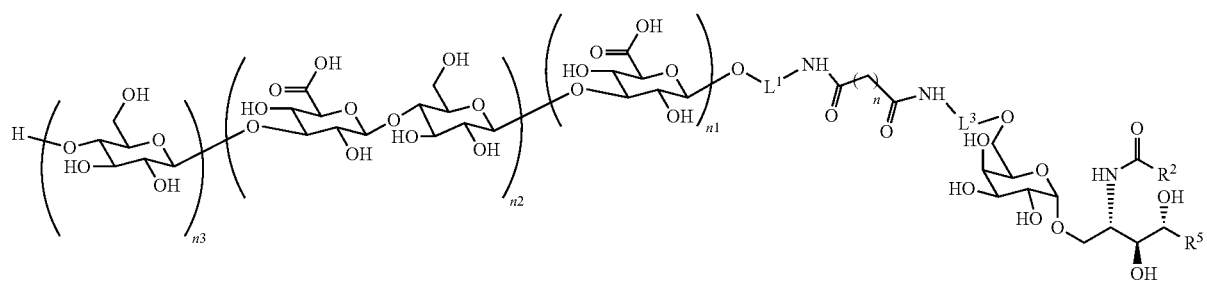

wherein $R^2$ is —$(X^1)_{p1}$—$(X^2)_{p2}$—$(X^3)_{p3}$—$X^4$;

$R^5$ is —$(Y^1)_{m1}$—$(Y^2)_{m2}$—$(Y^3)_{m3}$—$Y^4$;

$X^4$ represents: —H, -iPr, -tBu, -sBu,

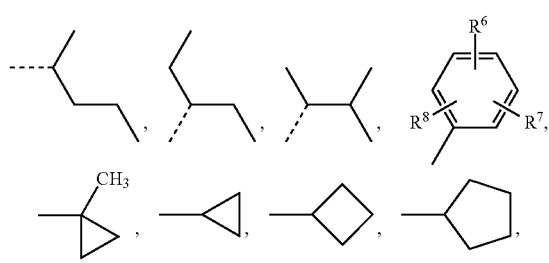

n2 is an integer selected from 1, 2, 3, 4, 5, 6, 7, 8, 9 and 10;

n1 and n3 represent independently of each other an integer selected from 0 and 1;

$L^1$ represents -$L^{1'}$-$L^{1''}$-$L^{1'''}$- or -$L^{1'}$-$L^{1''}$- or -$L^{1'}$-; and $L^3$ represents -$L^{3'}$-$L^{3''}$-$L^{3'''}$- or -$L^{3'}$-$L^{3''}$- or -$L^{3'}$-; and $L^{1'}$, $L^{1''}$, $L^{1'''}$, $L^{3'}$, $L^{3''}$, and $L^{3'''}$ are independently of each other selected from: —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —$CR^9R^{10}$—, —$CR^{11}R^{12}$—, —$CR^{13}R^{14}$—, —$CR^{15}R^{16}$—, —$CR^{17}R^{18}$—, —$CR^{19}R^{20}$—, —($CH_2$—$CH_2$—O)$_o$—$CH_2$—$CH_2$—, —($CH_2$—$CH_2$—O)$_o$—$CH_2$—, -o-$C_6H_4$—, -m-$C_6H_4$—, -p-$C_6H_4$—, —$CH_2$—S—$CH_2$—, —$CH_2$—O—$CH_2$—;

$R^6$, $R^7$ and $R^8$ are independently of each other selected from: —H, —$CH_3$, —$C_2H_5$, —F, —Cl, —Br, —$OCH_3$ and —$CF_3$;

$R^9$ to $R^{20}$ represent independently of each other —H, —$CH_3$, —$C_2H_5$, —$C_3H_7$;

o represents an integer selected from 1, 2, 3, 4, 5 and 6;

n is an integer selected from 1, 2, 3, 4, 5, 6, 7, 8, 9 and 10;

p1, p2, p3, m1, m2 and m3 represent independently of each other an integer from 0 to 10.

Preferably, the chain —$(X^1)_{p1}$—$(X^2)_{p2}$—$(X^3)_{p3}$— of $R^2$ in general formula (I), (I-A), (I-B), (I-C), (IV), (V), (VI), (VII) or (VIII) contains maximum 25 carbon atoms. Thus, the chain —$(X^1)_{p1}$—$(X^2)_{p2}$—$(X^3)_{p3}$— of $R^2$ in general formula (I), (I-A), (I-B), (I-C), (IV), (V), (VI), (VII) or (VIII) contains preferably between 5 and 25 carbon atoms, more preferably between 7 and 25 carbon atoms and even more preferably between 9 and 25 carbon atoms.

Preferably, the chain —$(Y^1)_{m1}$—$(Y^2)_{m2}$-$(Y^3)_{m3}$— of $R^5$ in general formula (I), (I-A), (I-B), (I-C), (IV), (V), (VI), (VII) or (VIII) contains maximum 14 carbon atoms.

Preferably, the residue $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{10}$—$CH_3$, —$(CH_2)_{10}$—$CH_3$, —$(CH_2)_9$—$CH_3$, —$(CH_2)_8$—$CH_3$,

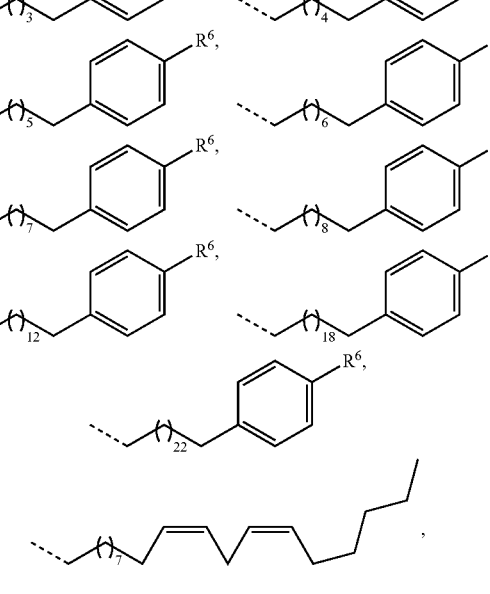

$R^6$ is selected from: —H, —$CH_3$, —F, —Cl, —$OCH_3$ and —$CF_3$.

Therefore, a conjugate of general formula (I), (I-A), (I-B), (I-C), (IV), (V), (VI), (VII) or (VIII), wherein the residue $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$,

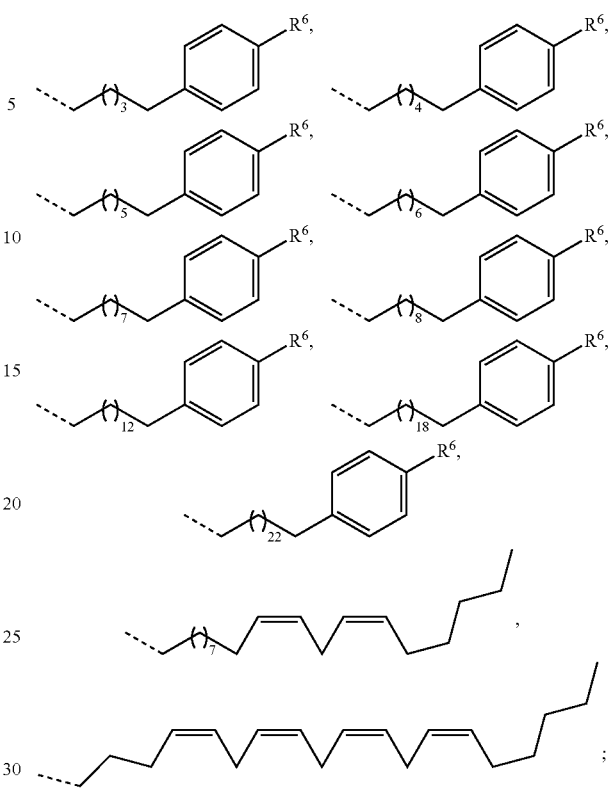

$R^6$ is selected from: —H, —$CH_3$, —F, —Cl, —$OCH_3$ and —$CF_3$, is especially preferred.

Also preferred is that the residue $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$, —$(CH_2)_7$—$CH_3$, —$(CH_2)_6$—$CH_3$, —$(CH_2)_5$—$CH_3$, —$(CH_2)_4$—$CH_3$, —$(CH_2)_2$-Ph, —$(CH_2)_3$-Ph, —$(CH_2)_4$-Ph, —$(CH_2)_5$-Ph, —$(CH_2)_6$-Ph, —$(CH_2)_7$-Ph, —$(CH_2)_8$-Ph, —$(CH_2)_9$-Ph.

Therefore, a conjugate of general formula (I), (I-A), (I-B), (I-C), (IV), (V), (VI), (VII) or (VIII), wherein the residue $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$, —$(CH_2)_7$—$CH_3$, —$(CH_2)_6$—$CH_3$, —$(CH_2)_5$—$CH_3$, —$(CH_2)_4$—$CH_3$, —$(CH_2)_2$-Ph, —$(CH_2)_3$-Ph, —$(CH_2)_4$-Ph, —$(CH_2)_5$-Ph, —$(CH_2)_6$-Ph, —$(CH_2)_7$-Ph, —$(CH_2)_8$-Ph, —$(CH_2)_9$-Ph is also preferred.

Especially preferred is a conjugate of general formula (I), (I-A), (I-B), (I-C), (IV), (V), (VI), (VII) or (VIII), wherein the residue $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$, —$(CH_2)_7$—$CH_3$, —$(CH_2)_6$—$CH_3$, —$(CH_2)_5$—$CH_3$, —$(CH_2)_4$—$CH_3$, —$(CH_2)_2$-Ph, —$(CH_2)_3$-Ph, —$(CH_2)_4$-Ph, —$(CH_2)_5$-Ph, —$(CH_2)_6$-Ph, —$(CH_2)_7$-Ph, —$(CH_2)_8$-Ph, —$(CH_2)_9$-Ph;

and the residue $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$,

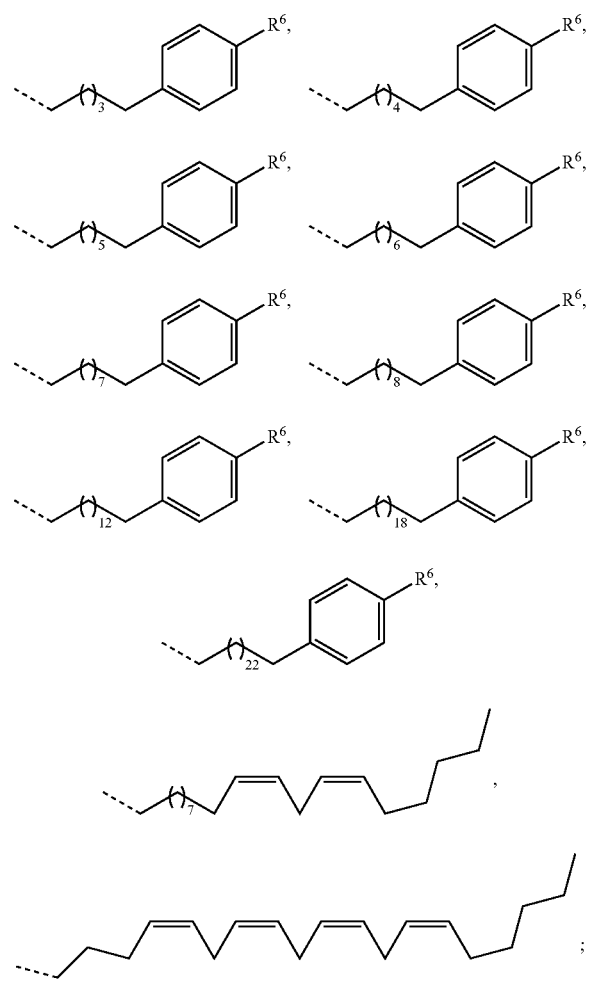

with R[6] being selected from: —H, —CH$_3$, —F, —Cl, —OCH$_3$ and —CF$_3$.

Especially preferred conjugates of the present invention have the fragments -L[1]- and -L[3]- independently of each other selected from: —CH$_2$—, —C$_2$H$_4$—, —C$_3$H$_6$—, —C$_4$H$_8$—, —C$_5$H$_{10}$— and —C$_6$H$_{12}$—. Thus, a conjugate of general formula (I), (I-A), (I-B), (I-C), (IV), (V), (VI), (VII) or (VIII), wherein the fragments -L[1]- and -L[3]- are independently of each other selected from: —CH$_2$—, —C$_2$H$_4$—, —C$_3$H$_6$—, —C$_4$H$_8$—, —C$_5$H$_{10}$— and —C$_6$H$_{12}$— is especially preferred.

A particularly preferred conjugate is a conjugate of general formula (I-D)

wherein
n2 is an integer selected from 1, 2, 3, 4, 5, 6, 7, 8, 9 and 10;
n1 and n3 represent independently of each other an integer selected from 0 and 1;
R[2] is selected from —(CH$_2$)$_{24}$—CH$_3$, —(CH$_2$)$_{23}$—CH$_3$, —(CH$_2$)$_{22}$—CH$_3$, —(CH$_2$)$_{21}$—CH$_3$, —(CH$_2$)$_{20}$—CH$_3$, —(CH$_2$)$_{19}$—CH$_3$, —(CH$_2$)$_{18}$—CH$_3$, —(CH$_2$)$_{17}$—CH$_3$, —(CH$_2$)$_{16}$—CH$_3$, —(CH$_2$)$_{15}$—CH$_3$, —(CH$_2$)$_{14}$—CH$_3$, —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$,

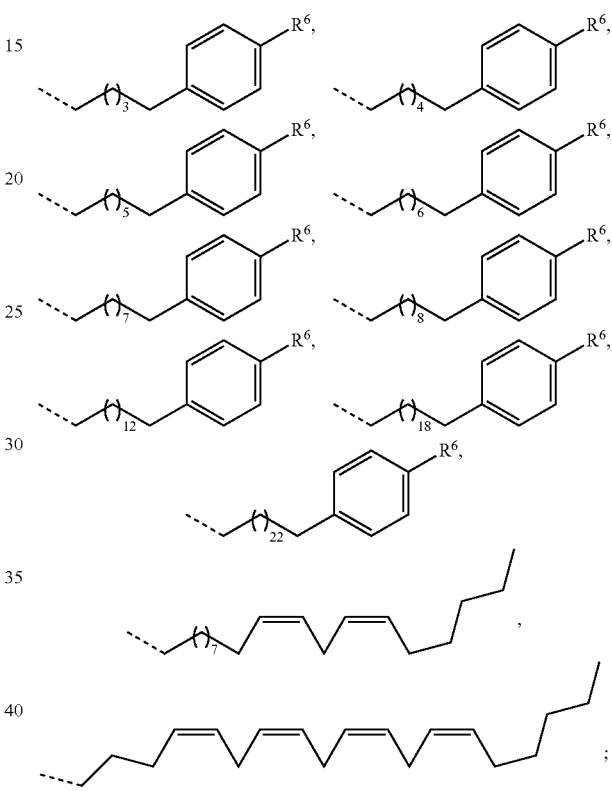

R[6] is selected from: —H, —CH$_3$, —F, —OCH$_3$ and —CF$_3$;
R[5] is selected from —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$, —(CH$_2$)$_7$—CH$_3$, —(CH$_2$)$_6$—CH$_3$, —(CH$_2$)$_5$—CH$_3$, —(CH$_2$)$_4$—CH$_3$, —(CH$_2$)$_2$-Ph, —(CH$_2$)$_3$-Ph, —(CH$_2$)$_4$-Ph, —(CH$_2$)$_5$-Ph, —(CH$_2$)$_6$-Ph, —(CH$_2$)$_7$-Ph, —(CH$_2$)$_8$-Ph, —(CH$_2$)$_9$-Ph;

I-D

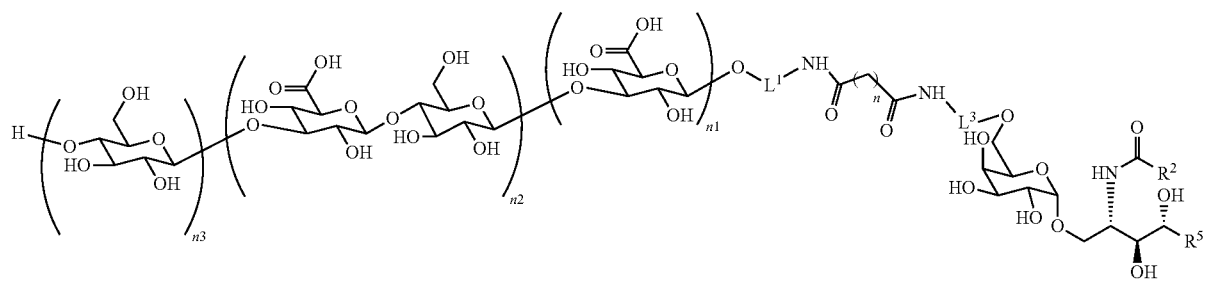

-L$^1$- and -L$^3$- are independently of each other selected from: —CH$_2$—, —C$_2$H$_4$—, —C$_3$H$_6$—, —C$_4$H$_8$—, —C$_5$H$_{10}$— and —C$_6$H$_{12}$—.

Also preferred is a conjugate of general formula (I-E)

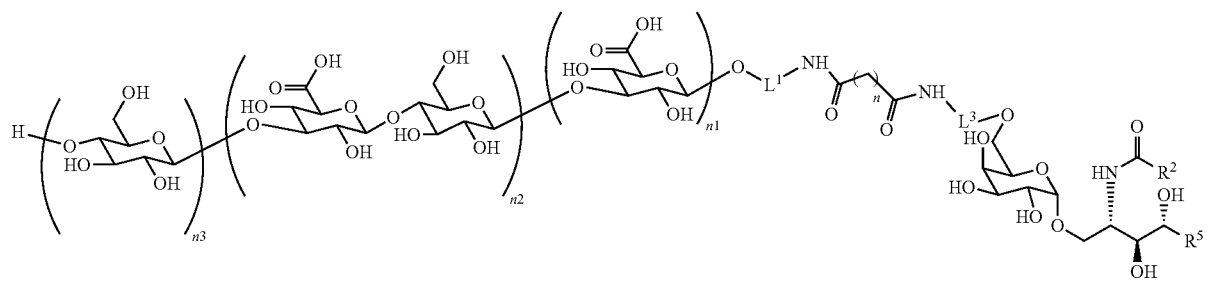

I-E wherein n2 is an integer selected from 1, 2, 3, and 4;

n1 and n3 represent independently of each other an integer selected from 0 and 1;

R$^2$ is selected from —(CH$_2$)$_{24}$—CH$_3$, —(CH$_2$)$_{23}$—CH$_3$, —(CH$_2$)$_{22}$—CH$_3$, —(CH$_2$)$_{21}$—CH$_3$, —(CH$_2$)$_{20}$—CH$_3$, —(CH$_2$)$_{19}$—CH$_3$, —(CH$_2$)$_{18}$—CH$_3$, —(CH$_2$)$_{17}$—CH$_3$, —(CH$_2$)$_{16}$—CH$_3$, —(CH$_2$)$_{15}$—CH$_3$, —(CH$_2$)$_{14}$—CH$_3$, —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$,

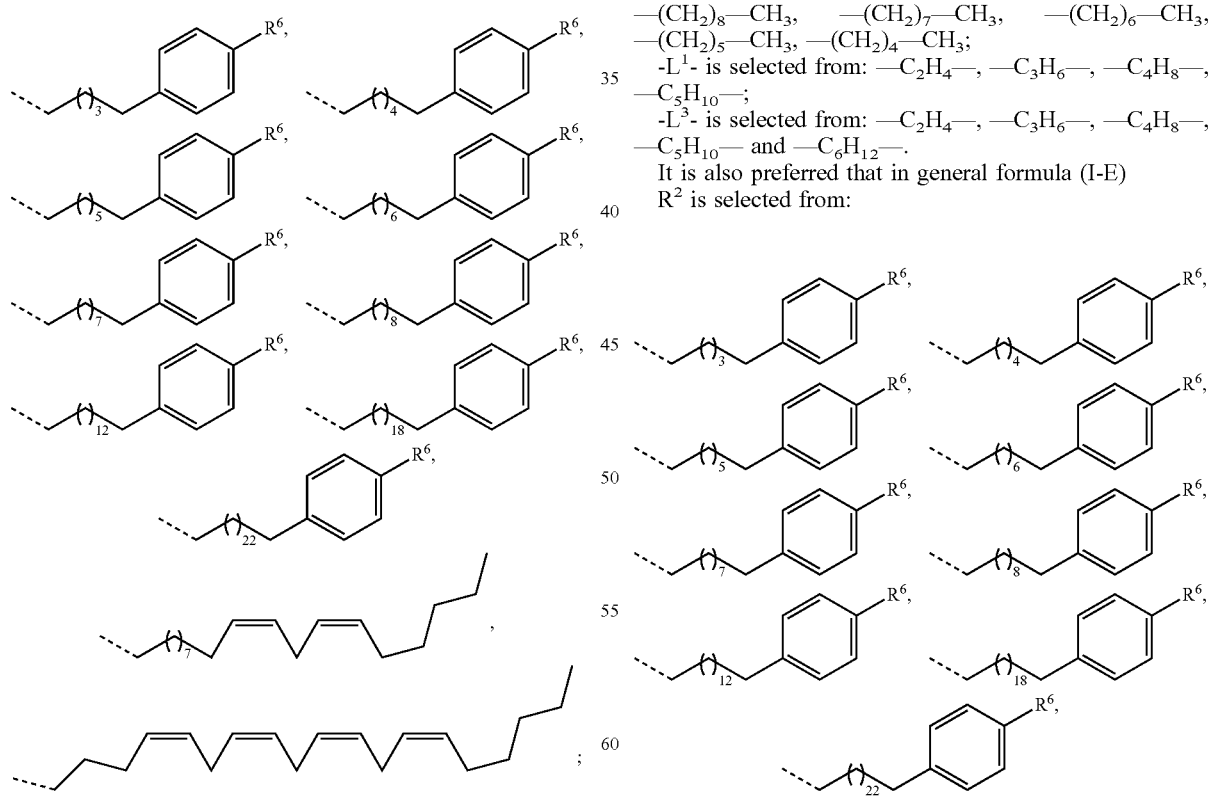

R$^6$ is selected from: —H, —CH$_3$, —F, —Cl, —OCH$_3$ and —CF$_3$;

R$^5$ is selected from —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$, —(CH$_2$)$_7$—CH$_3$, —(CH$_2$)$_6$—CH$_3$, —(CH$_2$)$_5$—CH$_3$, —(CH$_2$)$_4$—CH$_3$, —(CH$_2$)$_2$-Ph, —(CH$_2$)$_3$-Ph, —(CH$_2$)$_4$-Ph, —(CH$_2$)$_5$-Ph, —(CH$_2$)$_6$-Ph, —(CH$_2$)$_7$-Ph, —(CH$_2$)$_8$-Ph, —(CH$_2$)$_9$-Ph;

-L$^1$- and -L$^3$- are independently of each other selected from: —CH$_2$—, —C$_2$H$_4$—, —C$_3$H$_6$—, —C$_4$H$_8$—, —C$_5$H$_{10}$— and —C$_6$H$_{12}$—.

In general formula (I-E), preferably n2 represents 2,

R$^2$ is selected from —(CH$_2$)$_{24}$—CH$_3$, —(CH$_2$)$_{23}$—CH$_3$, —(CH$_2$)$_{22}$—CH$_3$, —(CH$_2$)$_{21}$—CH$_3$, —(CH$_2$)$_{20}$—CH$_3$, —(CH$_2$)$_{19}$—CH$_3$, —(CH$_2$)$_{18}$—CH$_3$, —(CH$_2$)$_{17}$—CH$_3$, —(CH$_2$)$_{16}$—CH$_3$, —(CH$_2$)$_{15}$—CH$_3$, —(CH$_2$)$_{14}$—CH$_3$, —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$;

R$^5$ is selected from —(CH$_2$)$_{13}$—CH$_3$, —(CH$_2$)$_{12}$—CH$_3$, —(CH$_2$)$_{11}$—CH$_3$, —(CH$_2$)$_{10}$—CH$_3$, —(CH$_2$)$_9$—CH$_3$, —(CH$_2$)$_8$—CH$_3$, —(CH$_2$)$_7$—CH$_3$, —(CH$_2$)$_6$—CH$_3$, —(CH$_2$)$_5$—CH$_3$, —(CH$_2$)$_4$—CH$_3$;

-L$^1$- is selected from: —C$_2$H$_4$—, —C$_3$H$_6$—, —C$_4$H$_8$—, —C$_5$H$_{10}$—;

-L$^3$- is selected from: —C$_2$H$_4$—, —C$_3$H$_6$—, —C$_4$H$_8$—, —C$_5$H$_{10}$— and —C$_6$H$_{12}$—.

It is also preferred that in general formula (I-E)

R$^2$ is selected from:

 ; 5

$R^6$ is selected from: —H, —$CH_3$, —F, —Cl, —$OCH_3$ and —$CF_3$; and $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_9$—$CH_3$, —$(CH_2)_8$—$CH_3$, —$(CH_2)_7$—$CH_3$, —$(CH_2)_6$—$CH_3$, —$(CH_2)_5$—$CH_3$, —$(CH_2)_4$—$CH_3$, A conjugate of general formula (I-E), wherein $R^5$ is selected from —$(CH_2)_2$-Ph, —$(CH_2)_3$-Ph, —$(CH_2)_4$-Ph, —$(CH_2)_5$-Ph, —$(CH_2)_6$-Ph, —$(CH_2)_7$-Ph, —$(CH_2)_8$-Ph, —$(CH_2)_9$-Ph is also preferred.

Preferably the conjugate of the present invention is selected from:

23
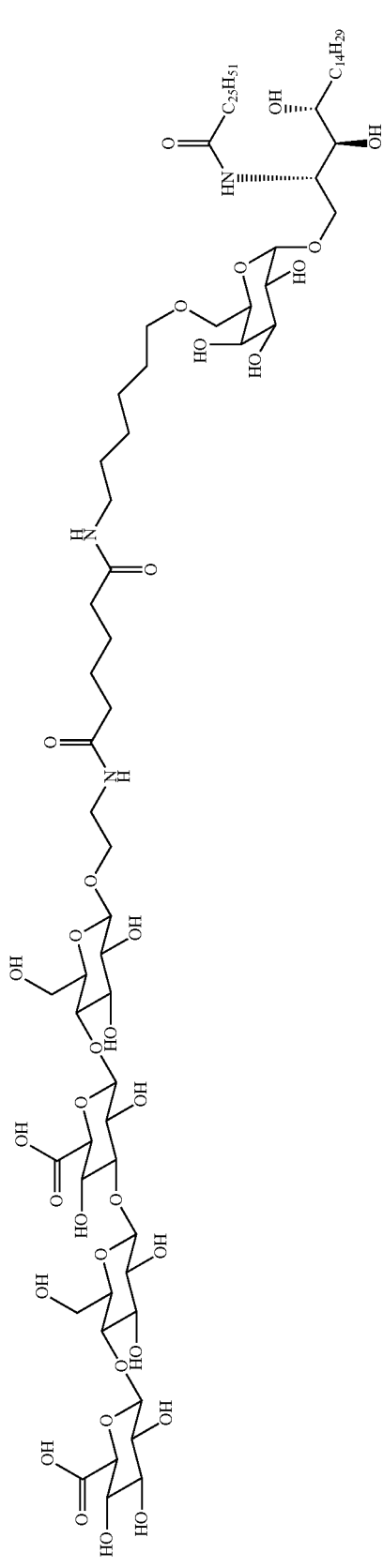
24
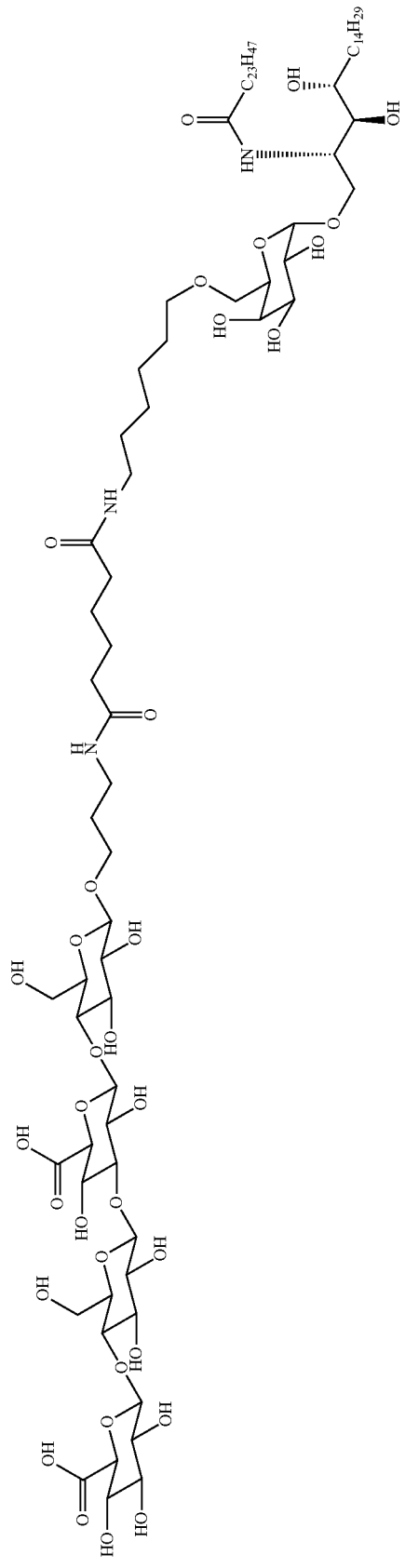

-continued
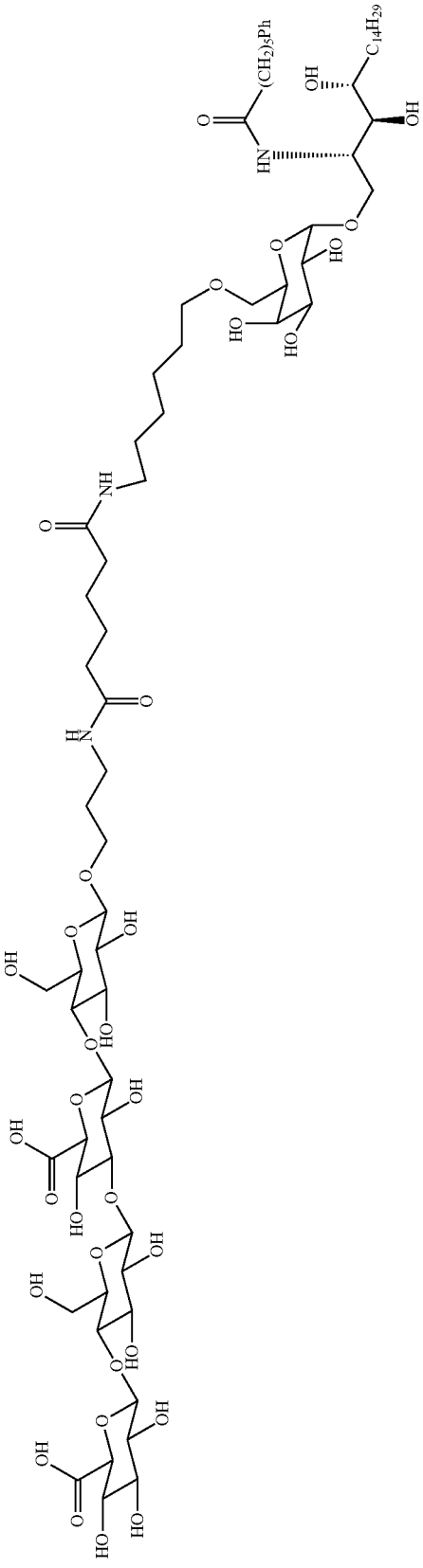
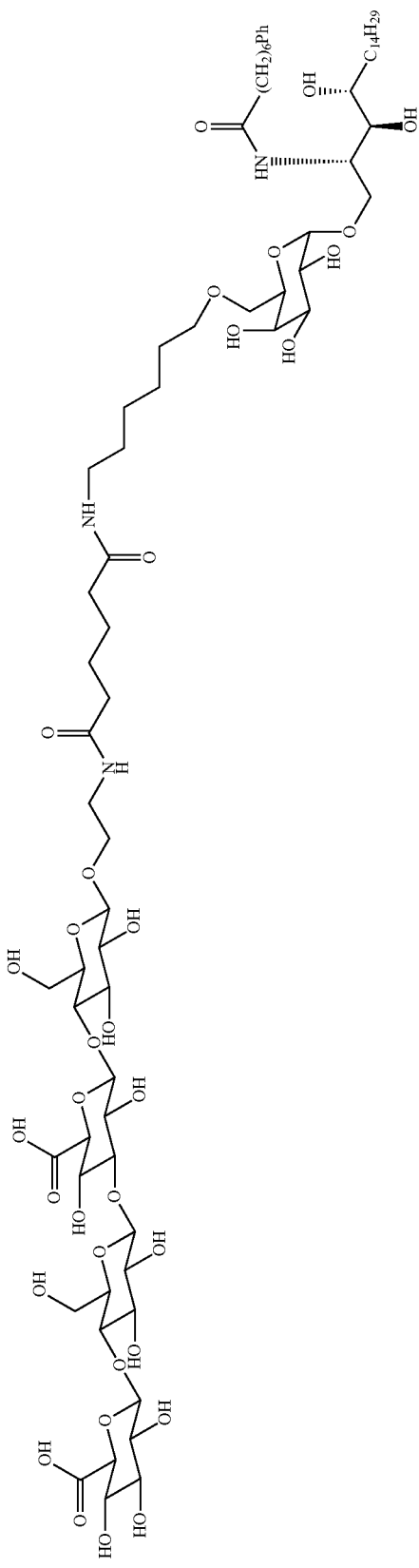

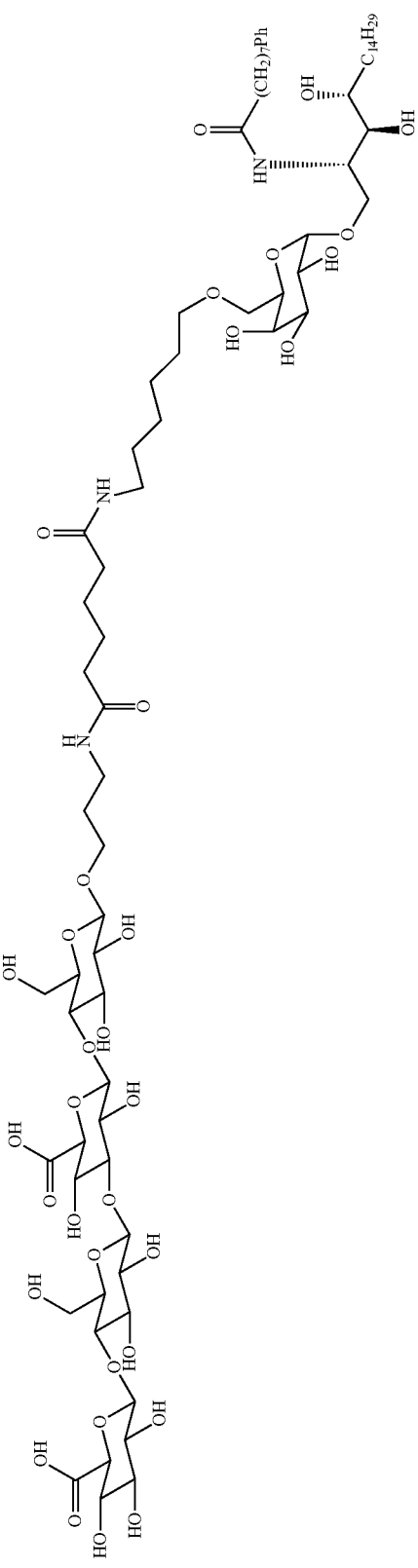
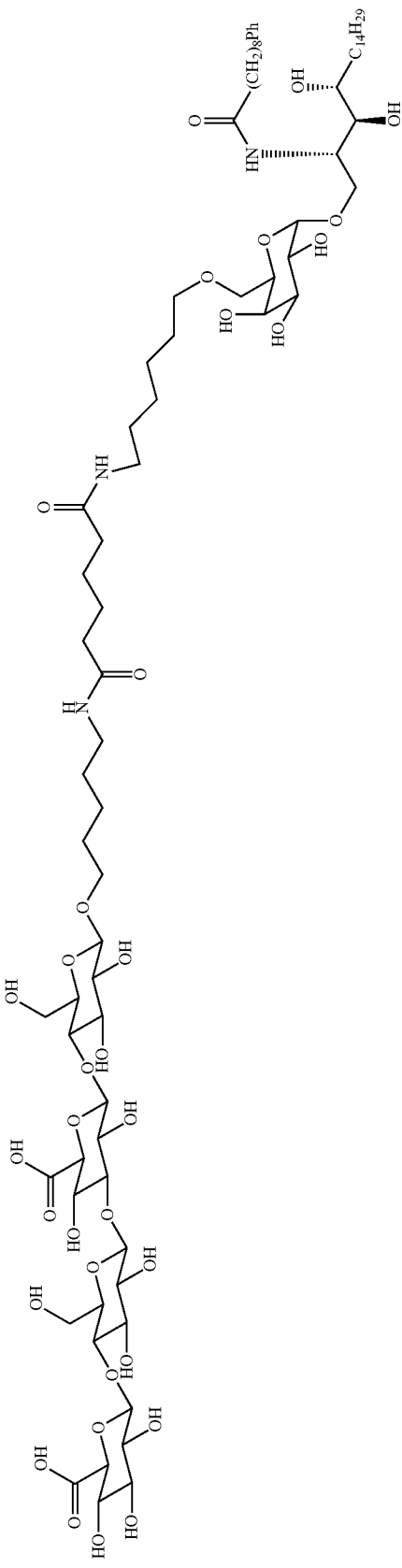

-continued
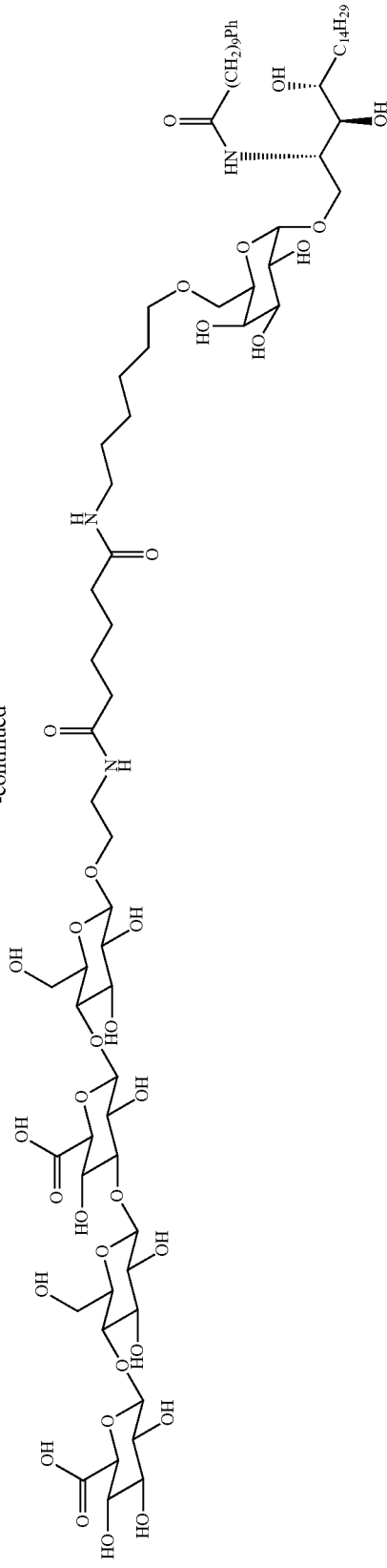
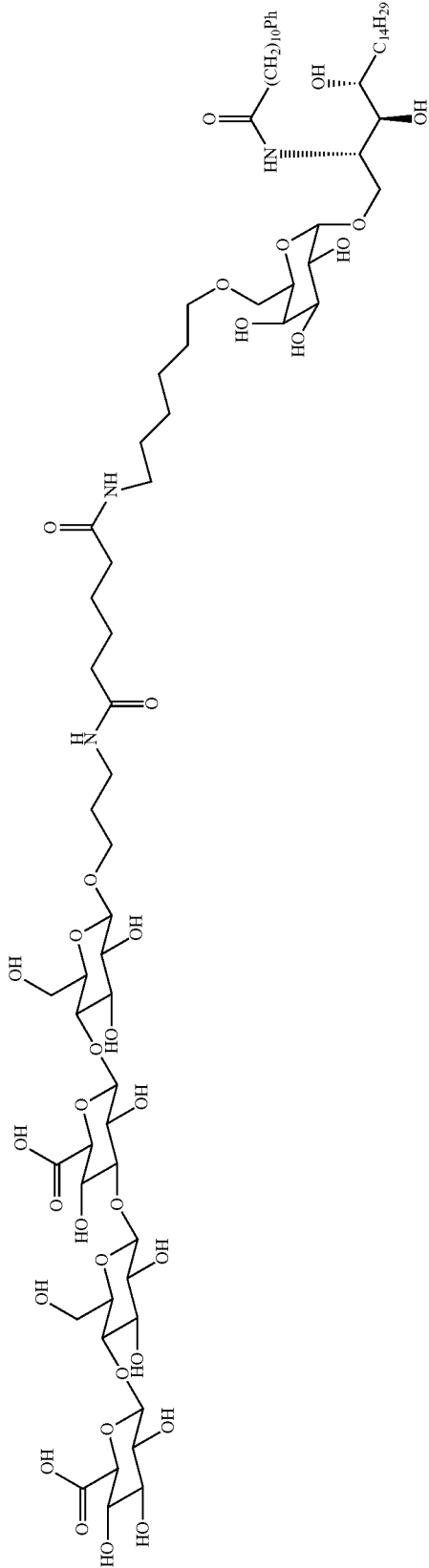

-continued
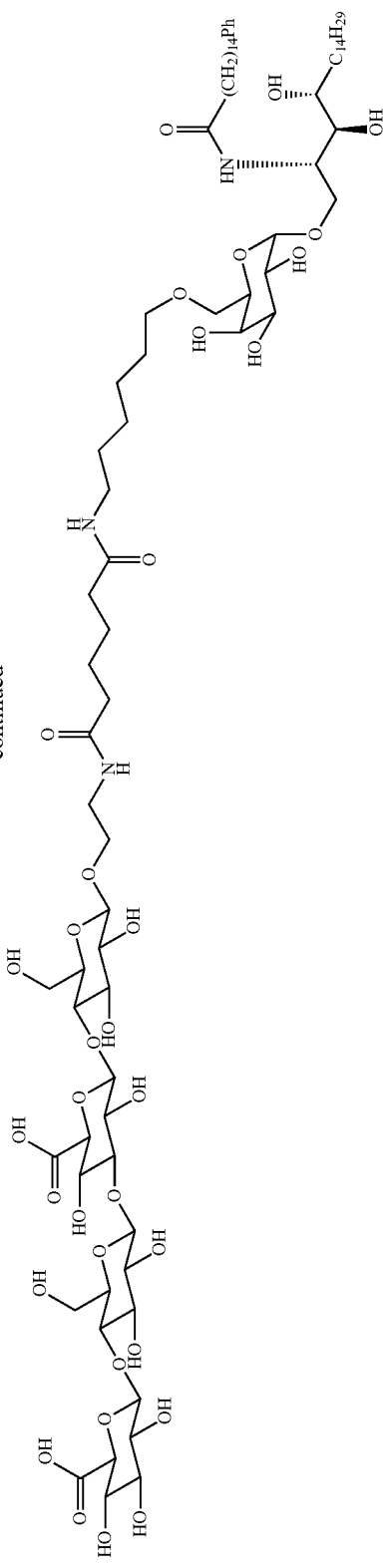
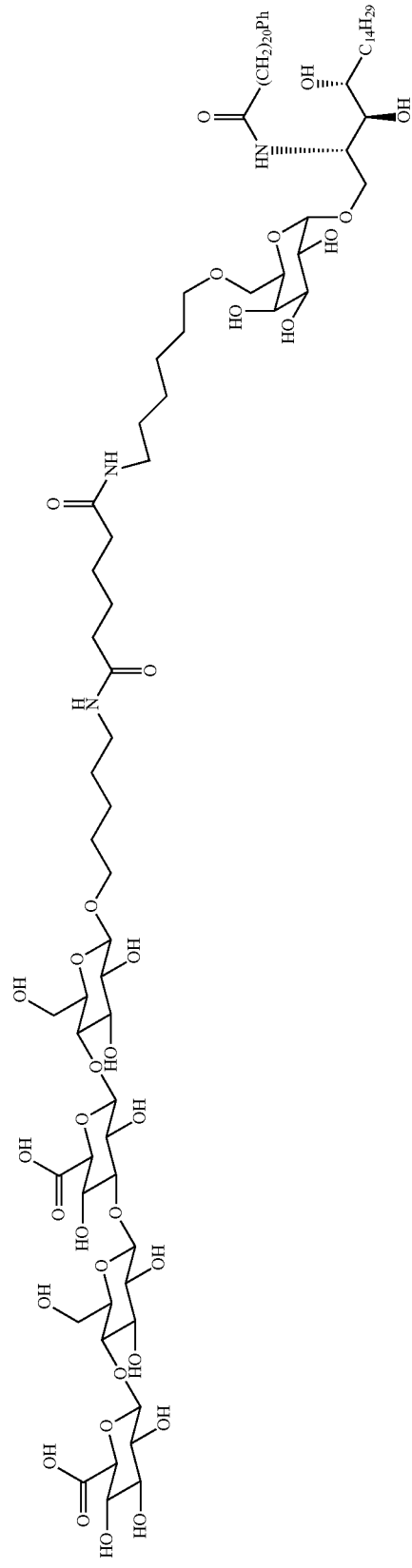

-continued
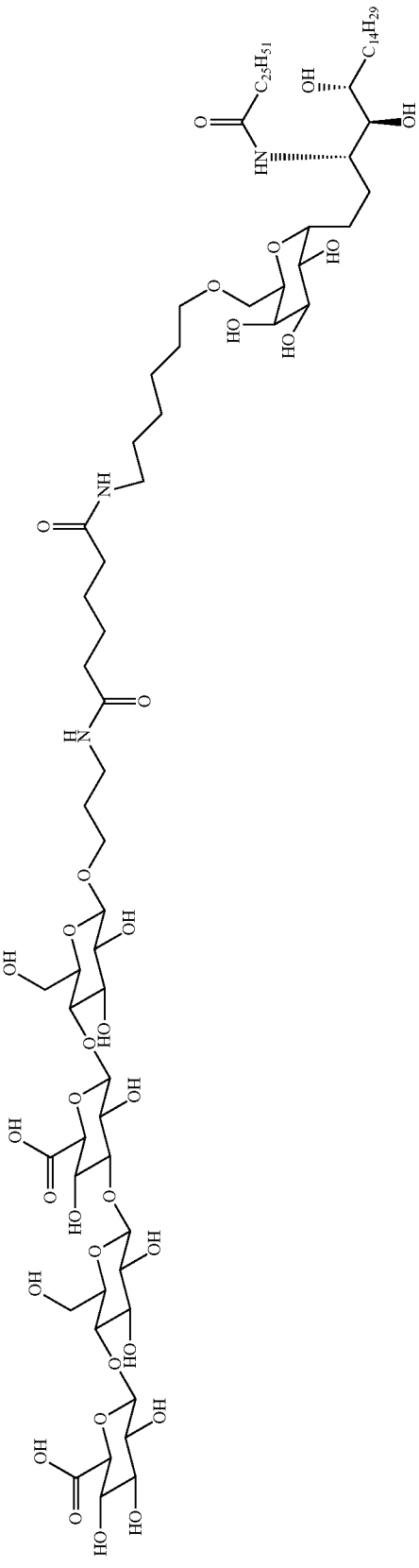
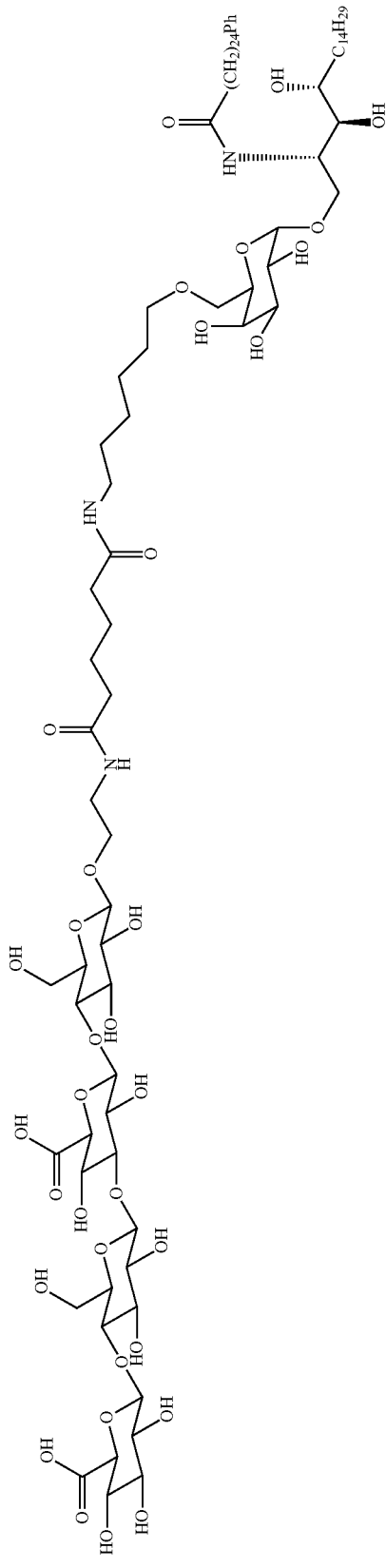

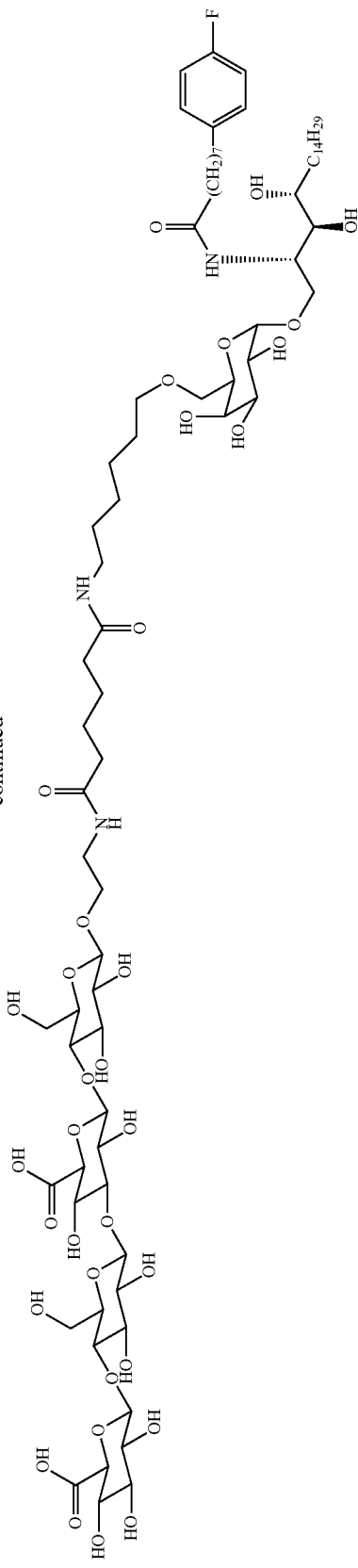
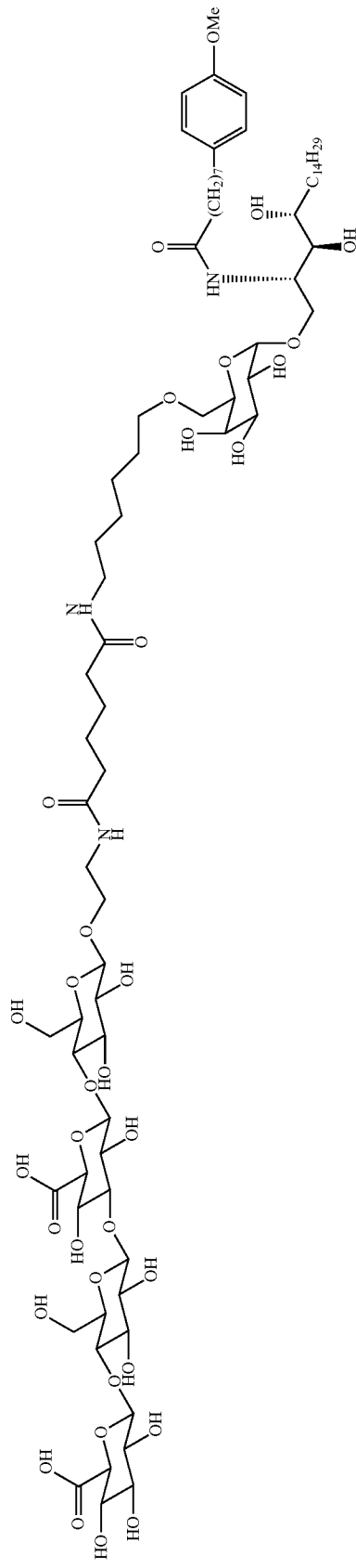

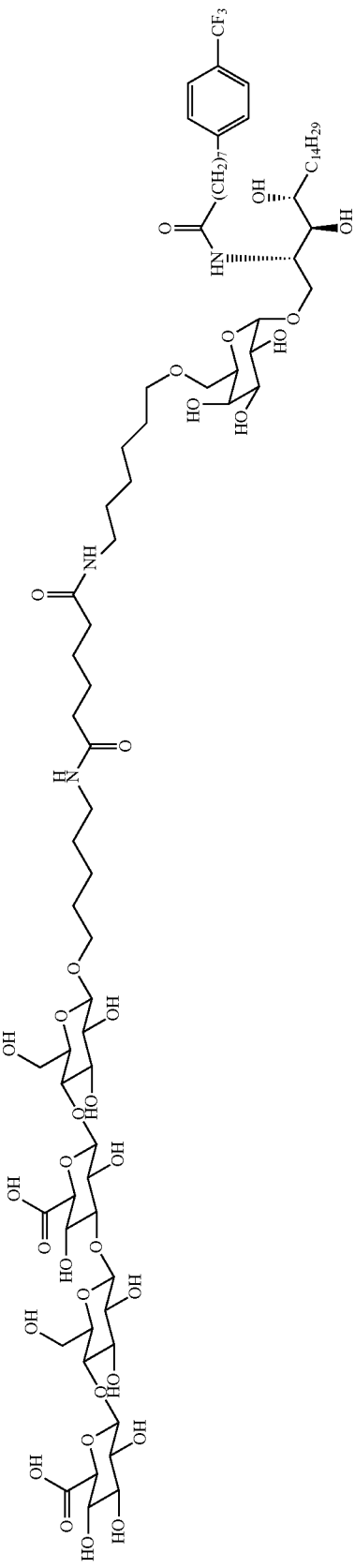
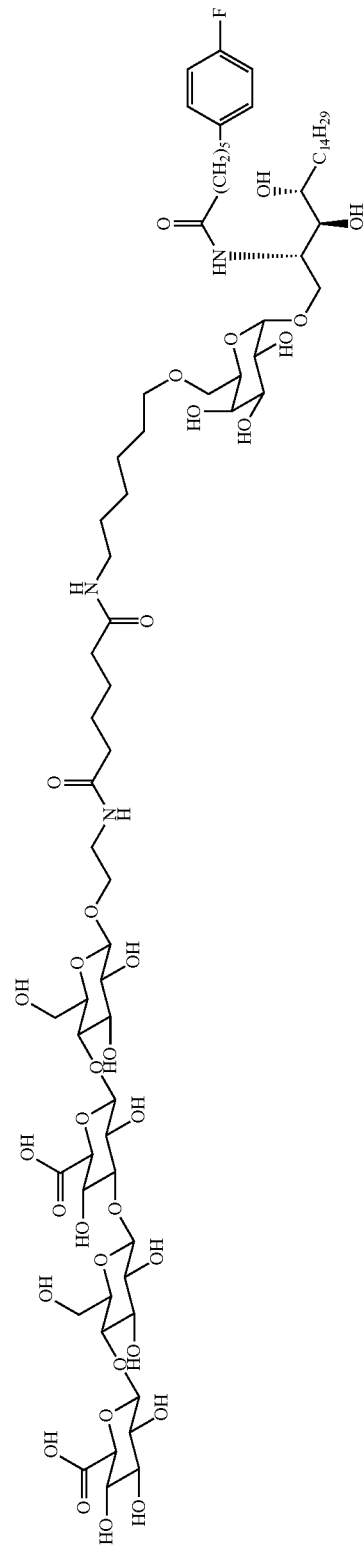

-continued
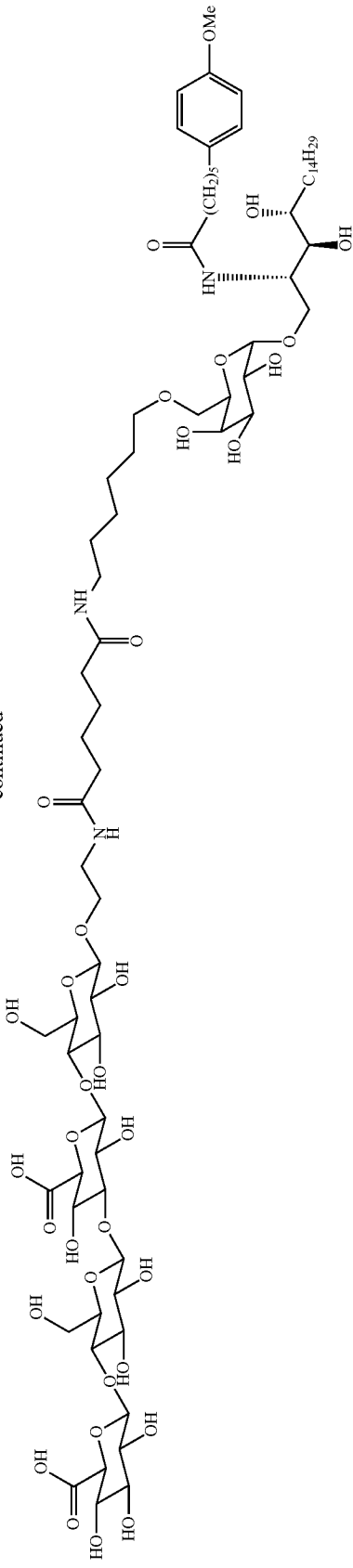
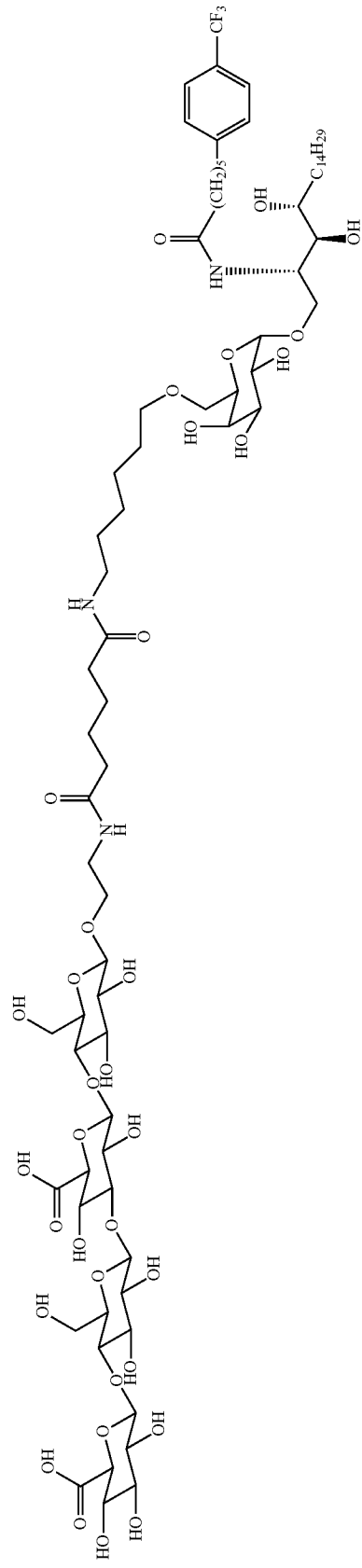

-continued
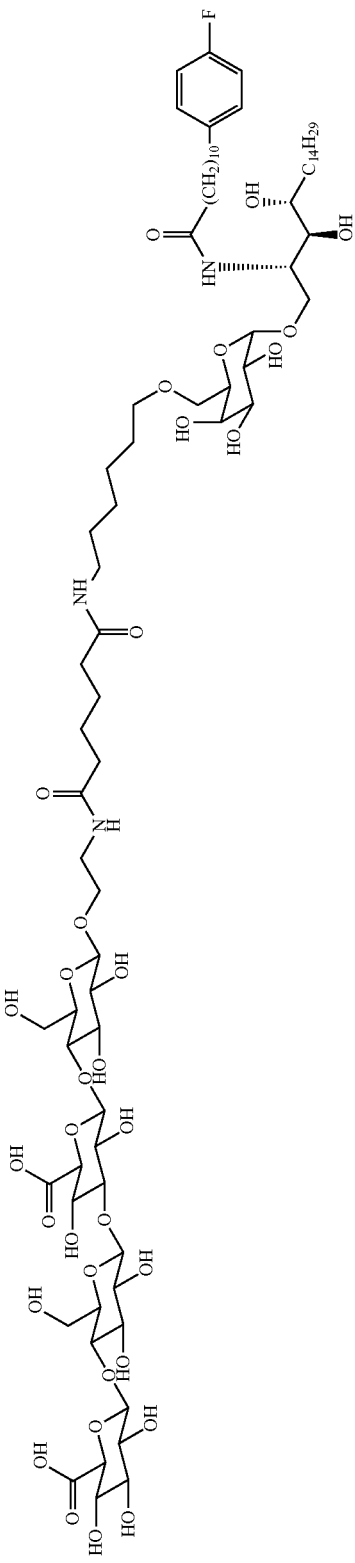
41
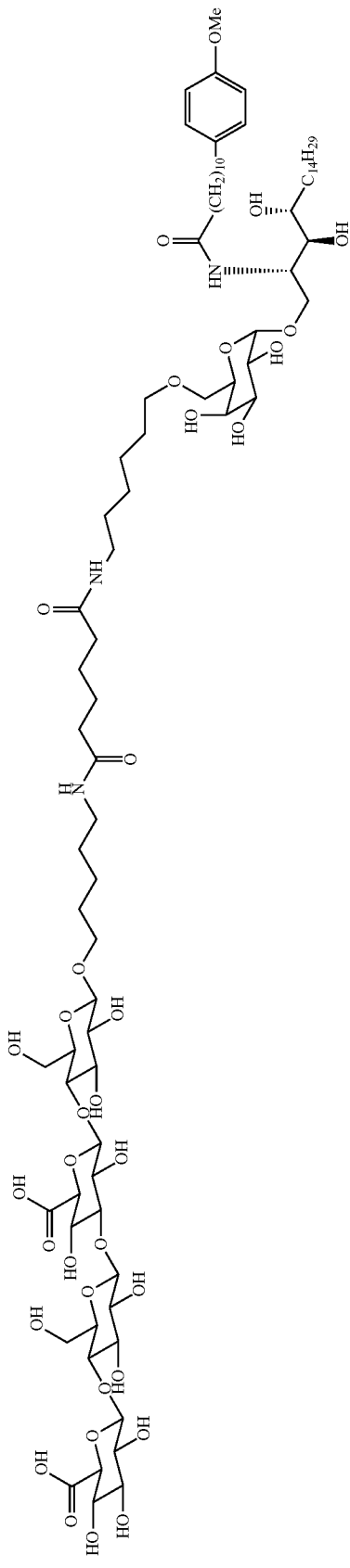
42

-continued
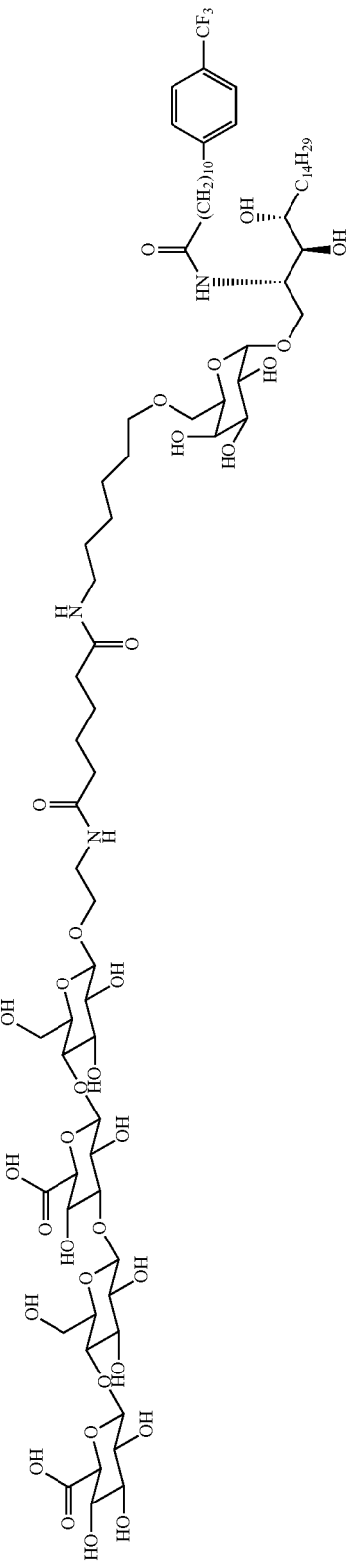
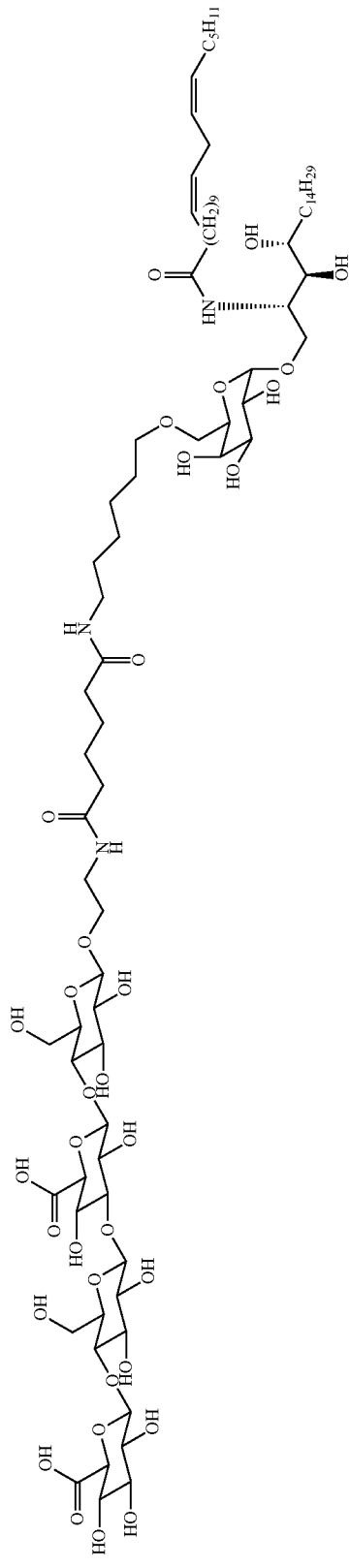

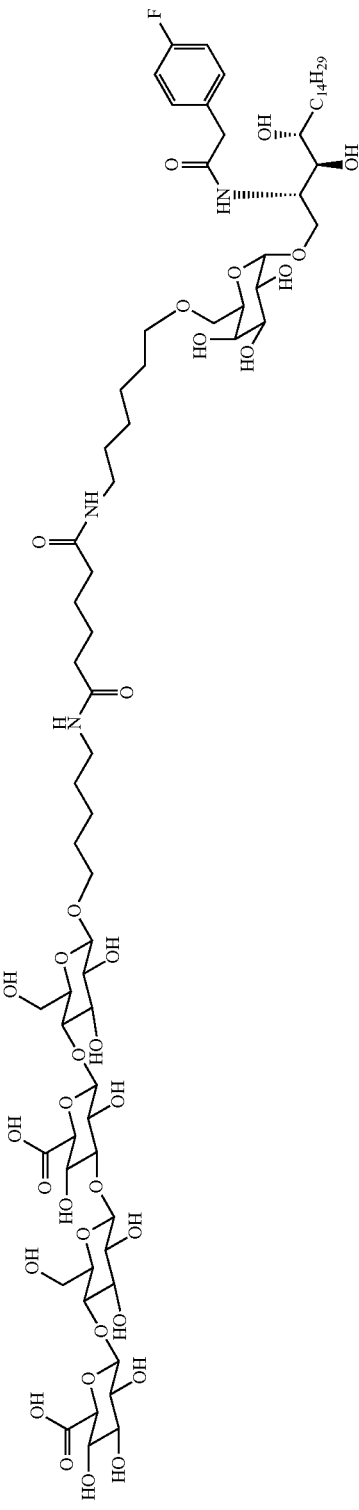
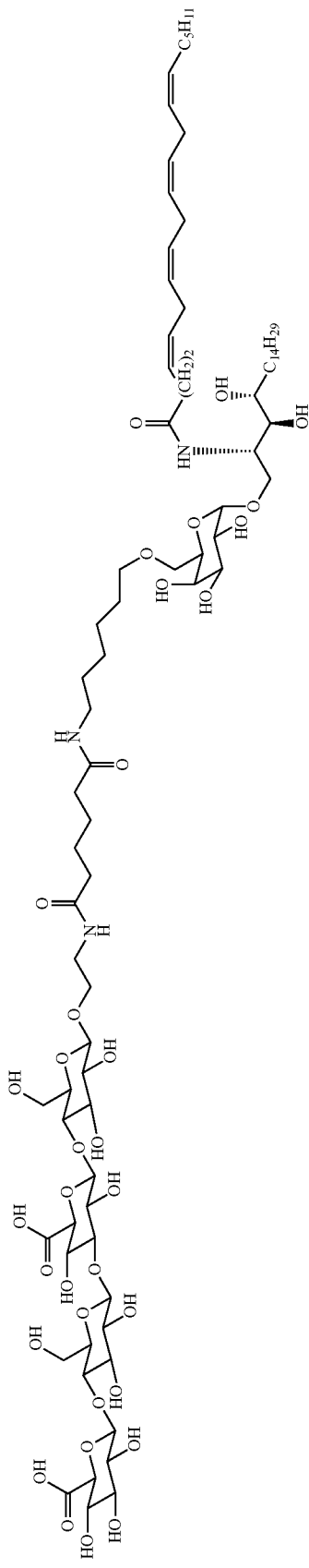

-continued
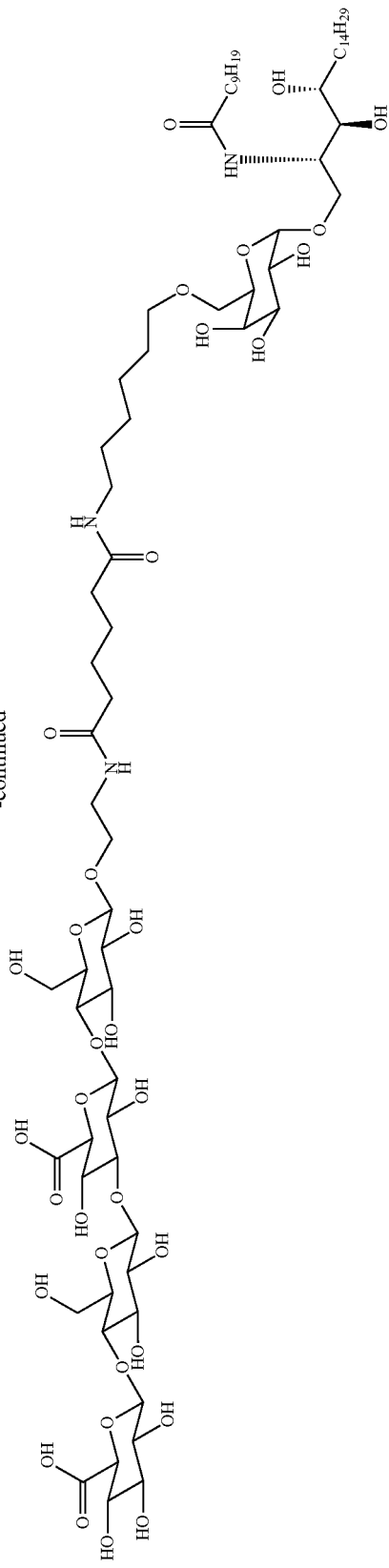
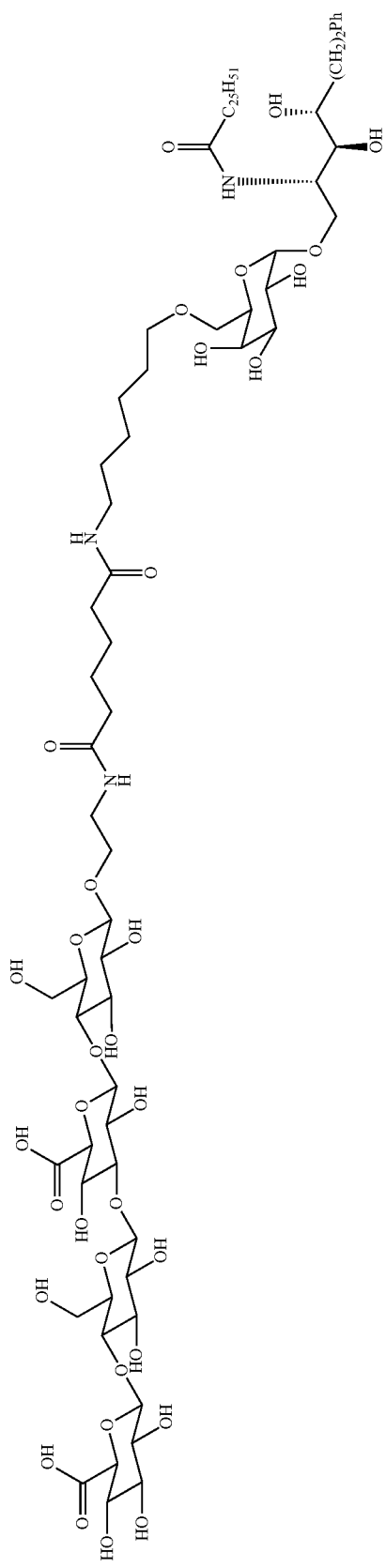

-continued
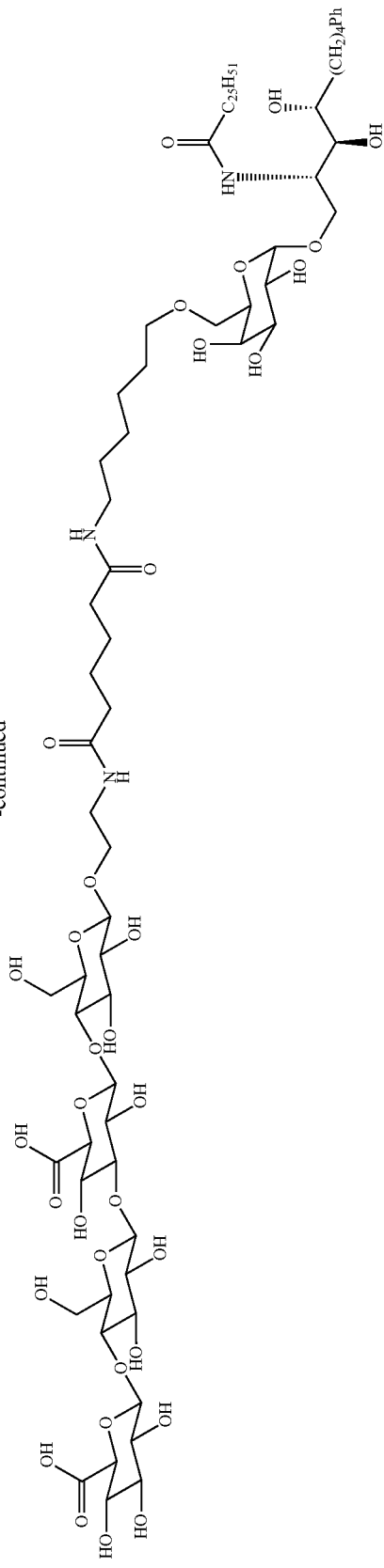
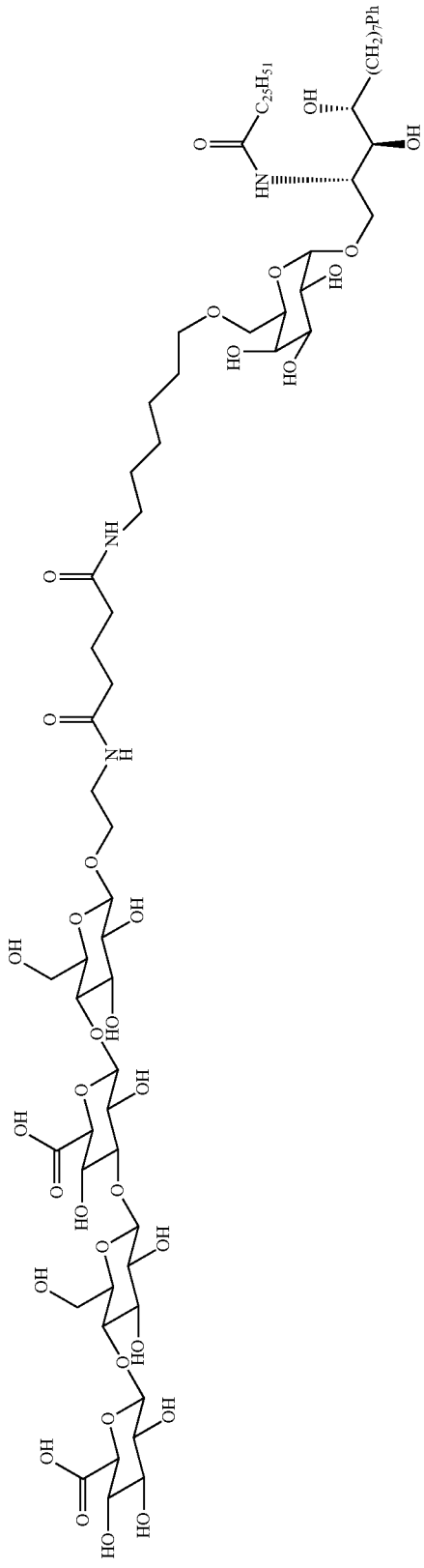

-continued
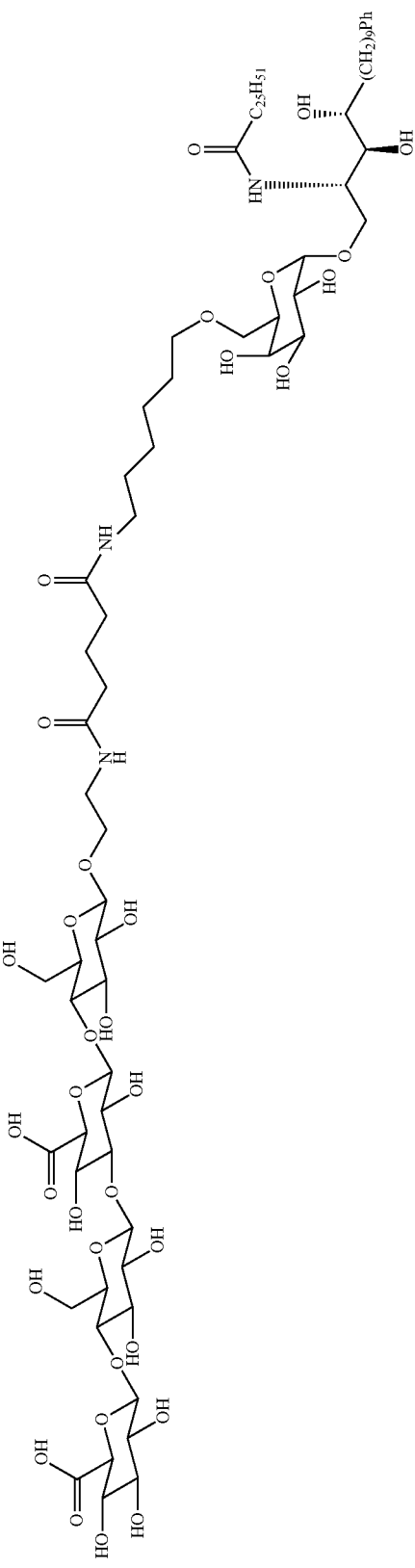
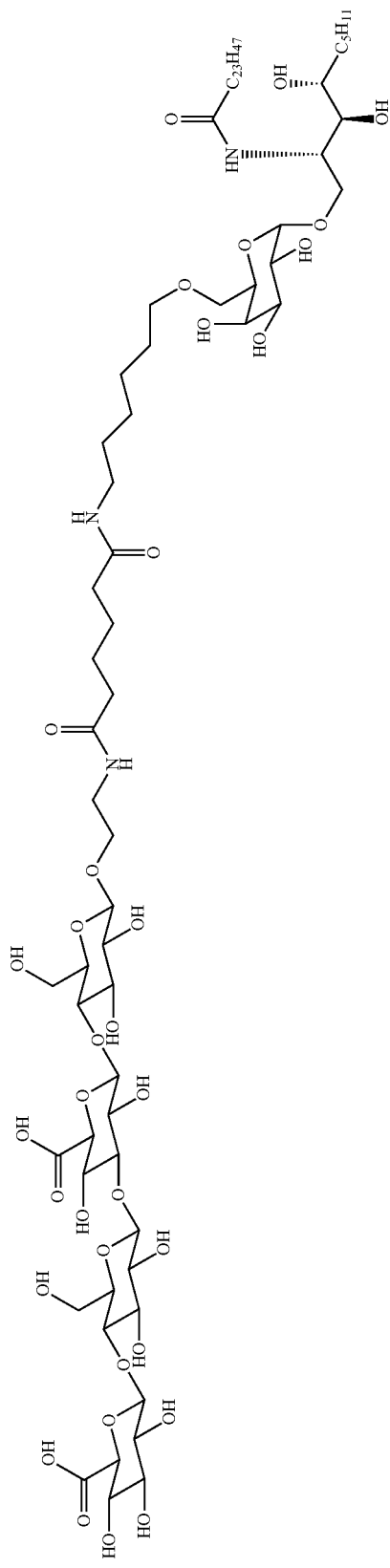

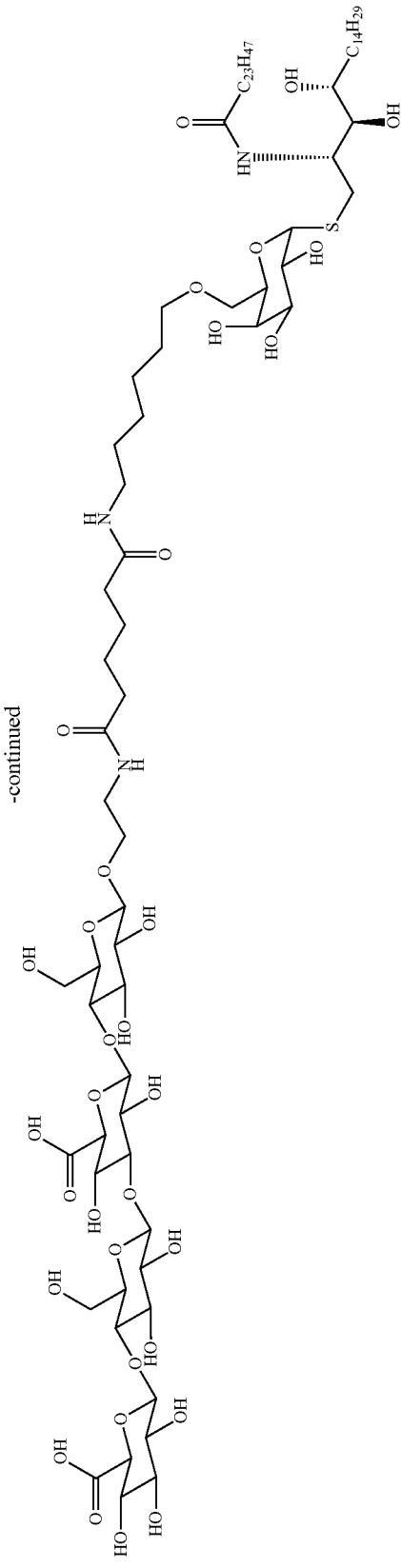
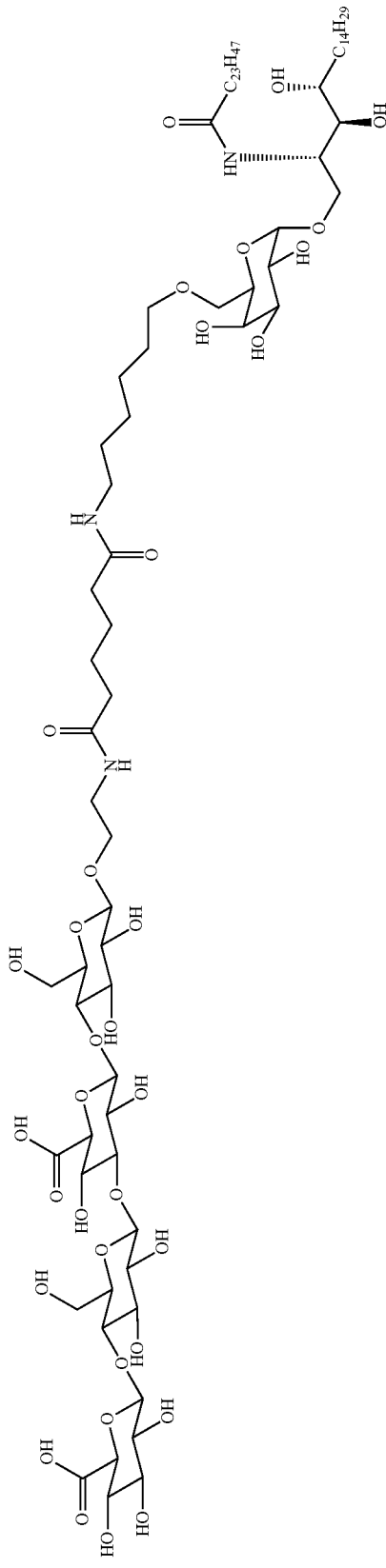

Another aspect of the present invention relates to the use of the inventive conjugates as drugs, i.e. as pharmaceutically active agents applicable in medicine.

Surprisingly, it was found that the novel conjugates of the present invention are also suitable to raise a protective immune response in human and/or animal host and therefore, are suitable for protection against diseases associated with *Streptococcus pneumoniae*, and especially *Streptococcus pneumoniae* type 3. Thus, the inventive conjugates disclosed herein are useful for prevention or treatment of diseases associated with *Streptococcus pneumoniae* type 3. Such diseases include, but are not restricted to pneumonia, meningitis, otitis media, bacteremia and acute exacerbation of chronic bronchitis, sinusitis, arthritis and conjunctivitis. Moreover, it was found that the treatment of an animal with the novel conjugate of the current invention lead to the formation of immunoglobuline IgG-isotypes, which prove the development of memory B-cells in the living organism. The presence of memory B-cells demonstrates immunological memory. Thus, it has been shown that the conjugates of the current invention are capable to induce a long term protection in an animal host against *Streptococcus pneumoniae* type 3. The described vaccination is moreover independent on further adjuvants, does not need any protein-carrier and refrigeration of the vaccine.

Therefore, conjugates according to the present invention are suitable for the use as a pharmaceutically active agent applicable in medicine, especially for use in vaccination against diseases caused or associated with *Streptococcus pneumoniae* type 3.

Another aspect of the present invention is directed to pharmaceutical compositions comprising at least one conjugate of the present invention as active ingredient, together with at least one pharmaceutically acceptable carrier, excipient and/or diluent. The pharmaceutical compositions of the present invention can be prepared in a conventional solid or liquid carrier or diluent at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural carbohydrates, corn sweeteners, natural and synthetic gums such as acacia, sodium alginate, carboxymethylcellulose, polyethylene glycol and waxes. Among suitable lubricants, there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The conjugates according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticizers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include carbohydrates such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances, which bind or "glue" together powder particles and make them cohesive by forming granules, thus serving as the "adhesive" in the formulation. Binders add cohesive strength already available in the diluent or bulking agent. Suitable binders include carbohydrates such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The mentioned pharmaceutical formulations, or more specifically vaccines are characterized in that they comprise a fully defined synthetic conjugate of general formula I.

The conjugates of the invention of the general formula I are present in said vaccine formulation in the range of 10 to 1000 µg/g. In a preferred embodiment of the invention the conjugates of general formula I are present in said vaccine formulation in the range of 10 to 1000 ng/g. In a more preferred embodiment of the invention the conjugates of general formula I are present in said vaccine formulation in the range of 100 to 1000 pg/g.

The mentioned vaccine formulation displays an extraordinary stability at room temperature due to the modular constitution of the compounds of the present invention, wherein said vaccine formulation may be maintained at a temperature of at least 25° C. for a period of at least 3 months prior to reconstitution. The temperature-stability of the herein described vaccine formulations constitutes a particular advantage of the present invention over the vaccines directed against Streptococcus pneumoniae type 3, which were described up to present. In a preferred embodiment of the invention the said period is comprises 6 months or at least 12 months.

When applied in vivo the conjugates of the present invention were found of being capable of effectively and continuously immunizing against Streptococcus pneumoniae type 3. This is rather advantageous, since thereby the conjugates of the present invention can stimulate the generation of antibodies of high titers and long lasting resistance in in vivo conditions, and moreover they exhibit a long-term stability at room temperature. Therefore, the conjugates of the present invention are particular heat stable and thus no refrigeration is required.

It is proved that the inventive conjugate of the general formula (I) form liposomes effectively as shown in FIG. 1 and in the Example D1.1. In order to form liposomes, the compound of general formula (I) is preferably mixed with additives such as DSPC (1,2-distearoyl-sn-glycero-3-phosphocholine). In the present invention, it is proved that the inventive compound of the general formula (I) has an amphiphlic character and thus enable to form nano-sized liposomes. The diameter of said liposomes is in the range between 200 nm and 250 nm. The formation of such nano-sized liposomes in an aqueous media is advantageous, since the pharmaceutical composition is stable over time and usually shows better bioavailability. Such liposome formation is a technical advantage for vaccine formulation.

A yet another aspect of the present invention refers to a method of inducing an immune response in a human and/or animal host against Streptococcus pneumoniae type 3 comprising administering to the human and/or animal host a therapeutically effective amount of the conjugate of general formula (I).

Chemical Synthesis

The conjugates of general formula I can be generated starting from carbohydrate II, which presents a linker $L^1$ having a terminal amino group, and glycosphingolipid III presenting at the C-6 position of the glycoside moiety a linker $L^3$ with a terminal amino group.

Scheme 1: Retrosynthetic analysis of the conjugates of general formula I.

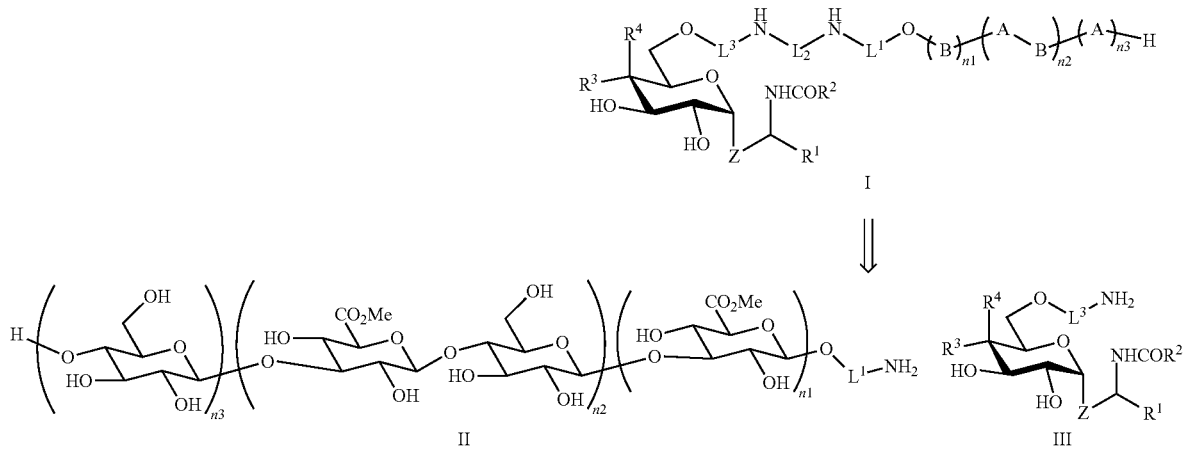

Synthesis of *Streptococcus pneumoniae* Type 3 Capsular Polysaccharide Related Carbohydrate.

The synthetic carbohydrates of general formula II, which are related to the capsular polysaccharide of *Streptococcus pneumoniae* type 3, can be accessed via a sequence of protecting group manipulation reactions and glycosylation reactions starting from glucose building blocks 2 and 3 and amino alcohol 4 (see Scheme 2).

said protecting groups are compatible with the conditions used during subsequent assembly and deprotection procedures.

Thus, starting from amino alcohol 4, fully protected saccharides 8, 9, 10, and 11, which are precursors of carbohydrates of general formula II can be assembled as shown in Scheme 3. More precisely, fully protected saccharide 8 that can be converted in few steps to carbohydrates of Scheme 2: Retrosynthetic scheme of carbohydrates of general formula II: n1 = 0 or 1; n2 = integer from 1 to 10; n3 = 0 or 1.

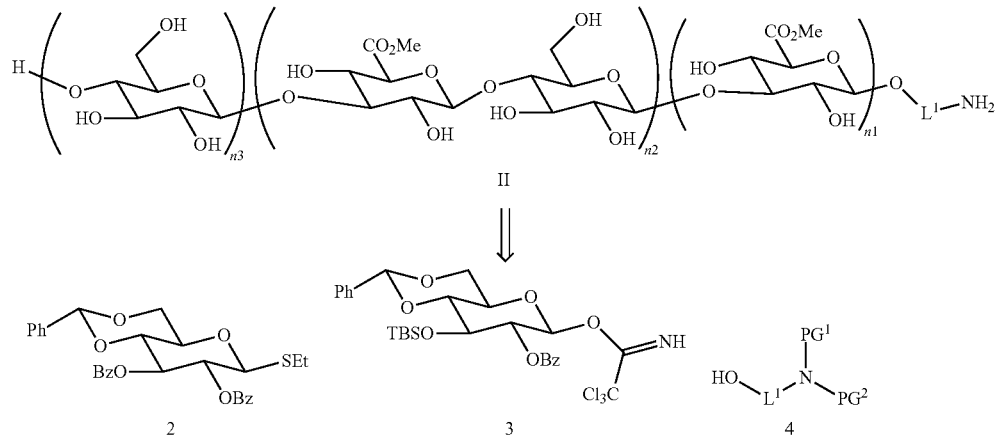

The synthetic carbohydrates of general formula II used in the present invention are functionalized at the reducing end with a linker $L^1$ having a terminal amino group, which allows for conjugation to the glycosphingolipid. Thioglycoside 2 has a benzoyl participating protecting group at the C-2 position to ensure the formation of the β-glycosidic linkage and a benzylidene acetal at the C-4 and C-6 positions, which can be regioselectively opened to free the C-4 hydroxyl for subsequent glycosylation. Glucose imidate 3 is equipped with a tert-butyl(dimethyl)silyl ether at the C-3 position and with a benzoate ester at the C-2 position to favour the formation of the β-glycosidic linkage. The amino group in amino alcohol 4 was masked with benzyl and benzyloxycarbonyl protecting groups, so as not to interfere as a nucleophile during the glycosylation reactions.

However, the person skilled in the art could use other suitable protecting groups for amine protection, as long as general formula II, with n1 equal to 1, n2 defined as above and n3 equal to 0 can be assembled following synthetic pathway A. Firstly, amino alcohol 4 and glucose imidate 3 are coupled using TMSOTf as activator to provide a monosaccharide intermediate (step a), which is further submitted to deprotection reaction by treatment with HF/pyridine to give compound 7 (step b) that represents the nucleophile for the following coupling reaction. The coupling reaction (step a) could be mediated by other activators known by the person skilled in the art, including $BF_3 \cdot OEt_2$, PPTS, $LiClO_4$ and $Cu(OTf)_2$. Moreover, the selective cleavage of the tert-butyl(dimethylsilyl)ether during the deprotection reaction (step b) could be accomplished using TBAF, HF·pyridine, $(Me_2N)_3S^+ F_2SiMe_3^-$ and many others reagents. After appending the first monosaccharide to the linker, target molecule 8 can be constructed by simple repetition of the reaction sequence comprising steps c and b. To accelerate the synthetic procedure, disaccharide building block 5 employed as elongation unit during the assembly, was prepared as described in Scheme 4.

First thioglucoside 2 was subjected to regioselective reductive opening by treatment with TES in presence of TFA to give alcohol 6, which was further coupled to imidate 3 in presence of TMSOTf to provide elongating unit 5.

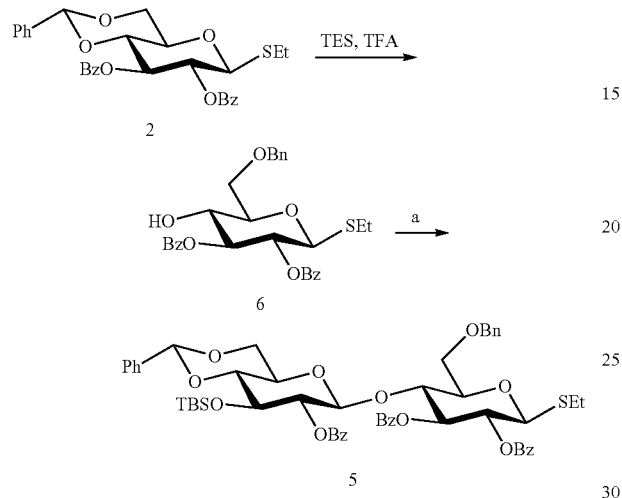

Scheme 4: Synthesis of elongating unit 5: a. 3, TMSOTf.

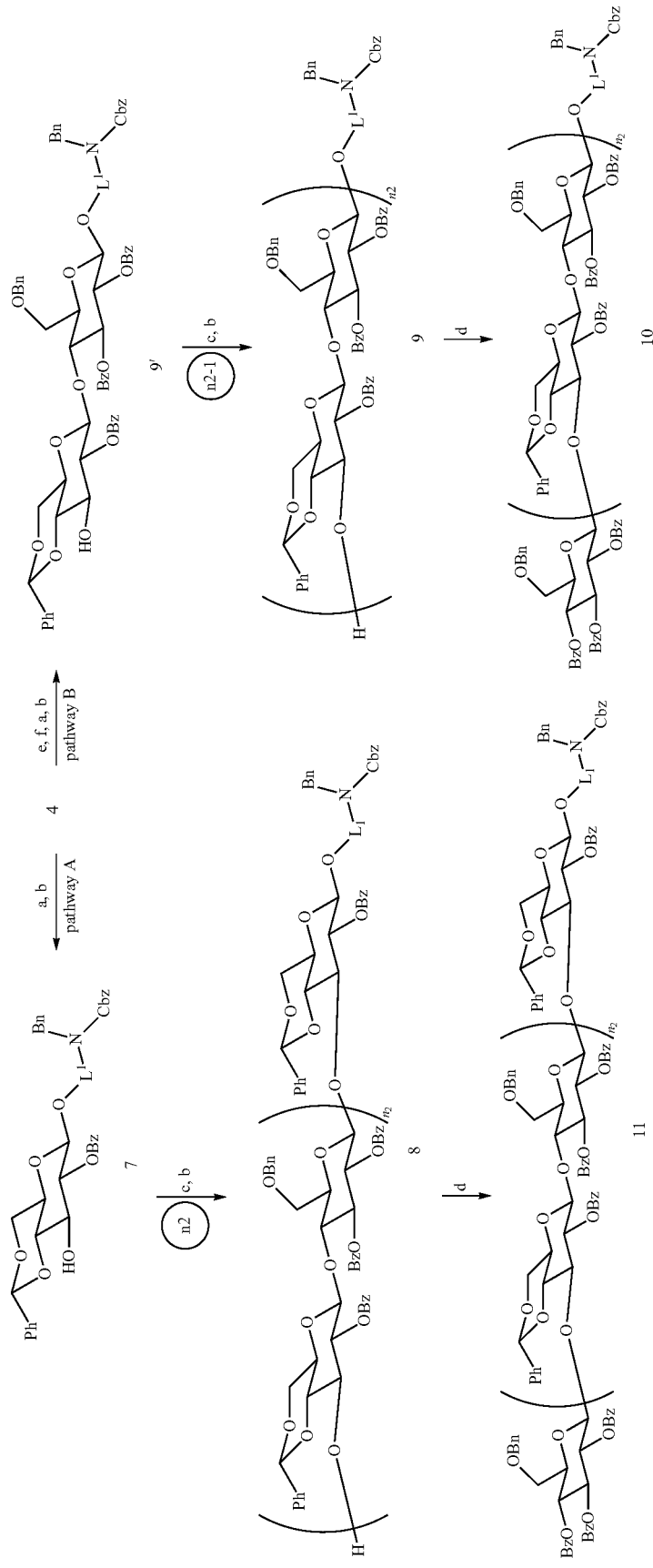
Scheme 3: Assembly of the carbohydrates related to the capsular polysaccharide of SP-3: a. 3, TMSOTf; b. HF, pyridiene; c. 5, NIS, TfOH; d. 12, NIS/TfOH; e. 2. NIS/TfOH; f. Et₃SiH, TFA With disaccharide 5 in hand, the reactions sequence comprising steps c and b was repeated till the desired length of the fully protected carbohydrate 8 (n2 times) was achieved. Each reactions sequence consists of a coupling reaction, followed by a deprotection reaction, thus introducing a [→3-β-D-Glcp-(1→4)-β-D-Glcp-(1→] repeating unit at the non reducing end of the growing saccharide leading after n2 repetitions to fully protected saccharide 8. The coupling reaction (step c) involves treatment of the growing saccharide with elongating unit 5 in presence of NIS/TfOH. Other activating systems, including IDPC, NBS—LiClO$_4$, Ph$_2$SO/Tf$_2$O, BSP-Tf$_2$O can be used as alternative to NIS/TfOH for mediating the glycosidic coupling.

In a similar way, fully protected saccharide 9, which is the precursor of synthetic carbohydrates of general formula II with n1 and n3 equal to 0 and n2 as previously defined can be accessed following pathway B. Specifically, building block 2 is reacted with amino alcohol 4 in presence of NIS/TfOH (step e) to give the corresponding β-glucoside on which the benzylidene acetal is regioselectively opened (step f) to provide the nucleophile for the next glycosylation reaction. Said nucleophile is subjected to glycosylation reaction (step a), followed by removal of the TBS protecting group (step b) to afford disaccharide 9'. By applying to the disaccharide 9', the n2-1 times repetition of the reactions sequence comprising step c and b, the target carbohydrate 9 can be assessed.

The precursors of carbohydrates of general formula II with n3 equal to 1 were obtained starting from fully protected carbohydrates 8 and 9. In this scope, building block 12 was prepared according to Scheme 5, to provide the sugar moiety at the non-reducing end of carbohydrates 10 and 11.

Scheme 5: Synthesis of glucose building block 12.

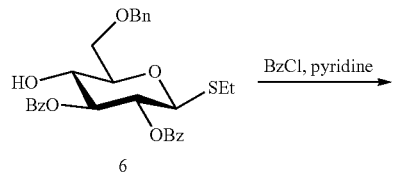

6

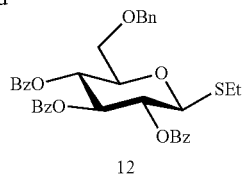

12

Finally, fully protected carbohydrates 8 and 9 were treated with thioglucoside 12 in presence of NIS/TfOH to provide fully protected carbohydrates 11 and 10.

Prior to the oxidation reaction, which is necessary for installing the carboxylic groups on the carbohydrates related to the SP3 capsular polysaccharide, the free hydroxyl groups on the glucose moiety at the non-reducing end of saccharides 8 and 9 were protected as a benzoate ester by treatment with benzoyl chloride in presence of pyridine.

To complete the synthesis, the fully protected saccharides accessed as described above were converted to the carbohydrates of general formula II (see Scheme 6). Firstly, the benzylidene acetals were cleaved by treatment with p-TSA and ethanethiol to free the primary hydroxyls prior to oxidation to the corresponding carboxylic acids. Then, the oxidation reaction using BAIB and TEMPO as oxidative agents was performed. The benzoate esters on the oxidized carbohydrates were further cleaved by applying Zemplen conditions, and the resulting intermediates were submitted to esterification and hydrogenolysis on Pd/C to give synthetic carbohydrates of general formula II.

Scheme 6: Synthesis of carbohydrates of general formula II: n1 = 0 or 1; n2 = integer from 1 to 10; n3 = 0 or 1.

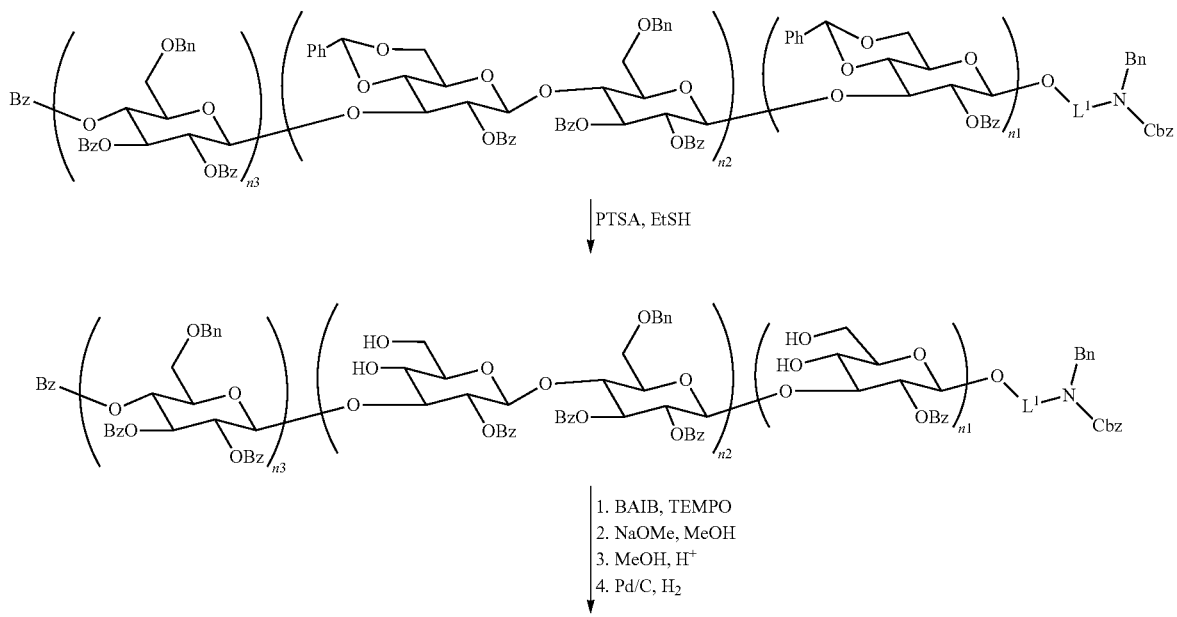

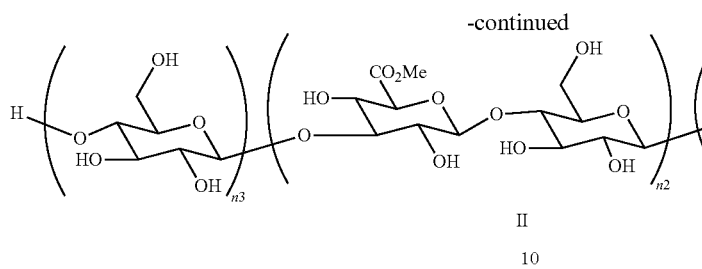
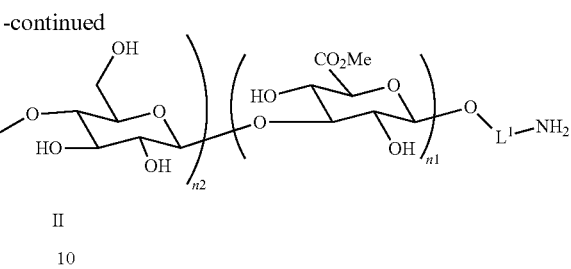

II
10

Synthesis of the Glycosphingolipid III

The glycosphingolipids of general formula III, suitable for obtaining conjugates of general formula I can be accessed through a variety of synthetic pathways (U.S. Pat. No. 7,771,726 B2; WO 2006027685 A2; X. Li et al. *PNAS* 2010, 107, 29, 13010-13015).

For instance, the glycosphingolipids according to the present invention with Z being —OCH$_2$— and R$^1$ being

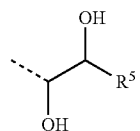

can be synthesized according to the synthetic pathway described below.

Commercially available L-Boc serine was chosen as starting material and converted in three steps to aldehyde 13 (see Scheme 7). The residue R$^5$ was introduced on the molecule by applying Wittig reaction. Hence, triphenylphosphonium ylide 14, which was prepared from the corresponding bromide R$^5$CH$_2$Br, was reacted with aldehyde 13 in presence of n-butyl lithium to provide exclusively Z-alkene 15. Conveniently, a variety of bromides of general formula R$^5$CH$_2$Br are commercially available or can be easily accessed by the person skilled in the art. Cleavage of the isopropylidene moiety with p-TSA, followed by Sharpless dihydroxylation and subsequent removal of the tert-butyloxycarbonyl protecting group in presence of trifluoroacetic acid provided triol 16. At this level, the residue R$^1$ was entirely introduced on the molecule. In the next step, the residue R$^2$ was appended by simple amide bond formation. Treatment of the activated ester 17 with amine 16 gave amide 18, which was converted in two steps to ceramide 19 ready for conjugation to the glucose or galactose sugar moiety.

Scheme 7: Synthesis of ceramide 19 ready for conjugation.

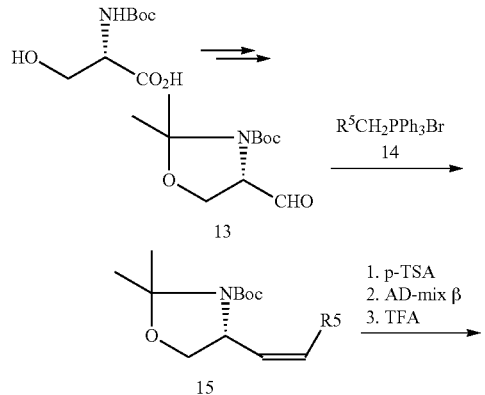

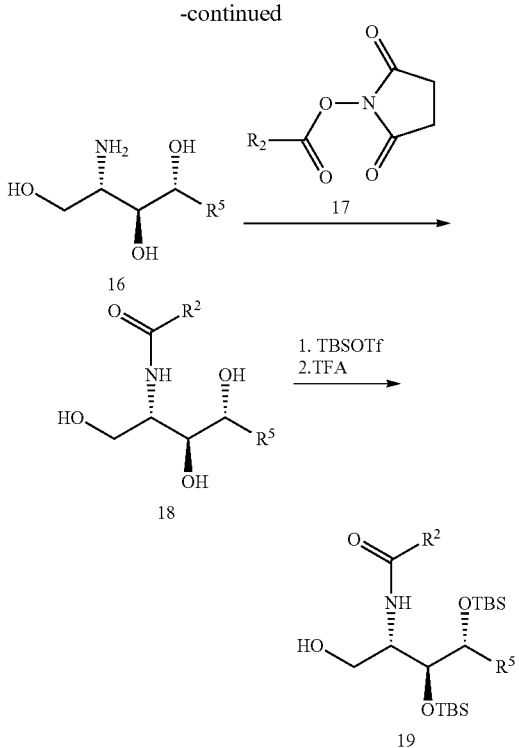

Glucose building block 29 and galactose building block 30 ready for conjugation with the ceramide 19 were synthesized starting from D-glucose 20, and D-galactose 21, respectively. Standard protecting group chemistry depicted on Scheme 8 provides suitably protected glucose 24 and galactose 25 with free alcohol at C6 position. The introduction of the linker L$^3$ at the C6 position was achieved at this level via Williamson's etherification with azide 26 of general formula TsO-L$^3$-N$_3$. A variety of azides of general formula TsO-L$^3$-N$_3$ can be prepared following routes described in the literature and known to the person skilled in the art. Scheme 9 describes such a synthetic route, which provides azide 26 in 3 steps starting from diol 31 that can be commercially available or accessed via modification of commercially available material.

Scheme 8: Synthesis of glycosyl imidates 29 and 30.

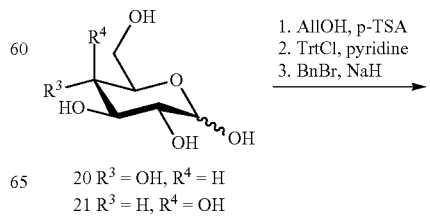

20 R$^3$ = OH, R$^4$ = H
21 R$^3$ = H, R$^4$ = OH

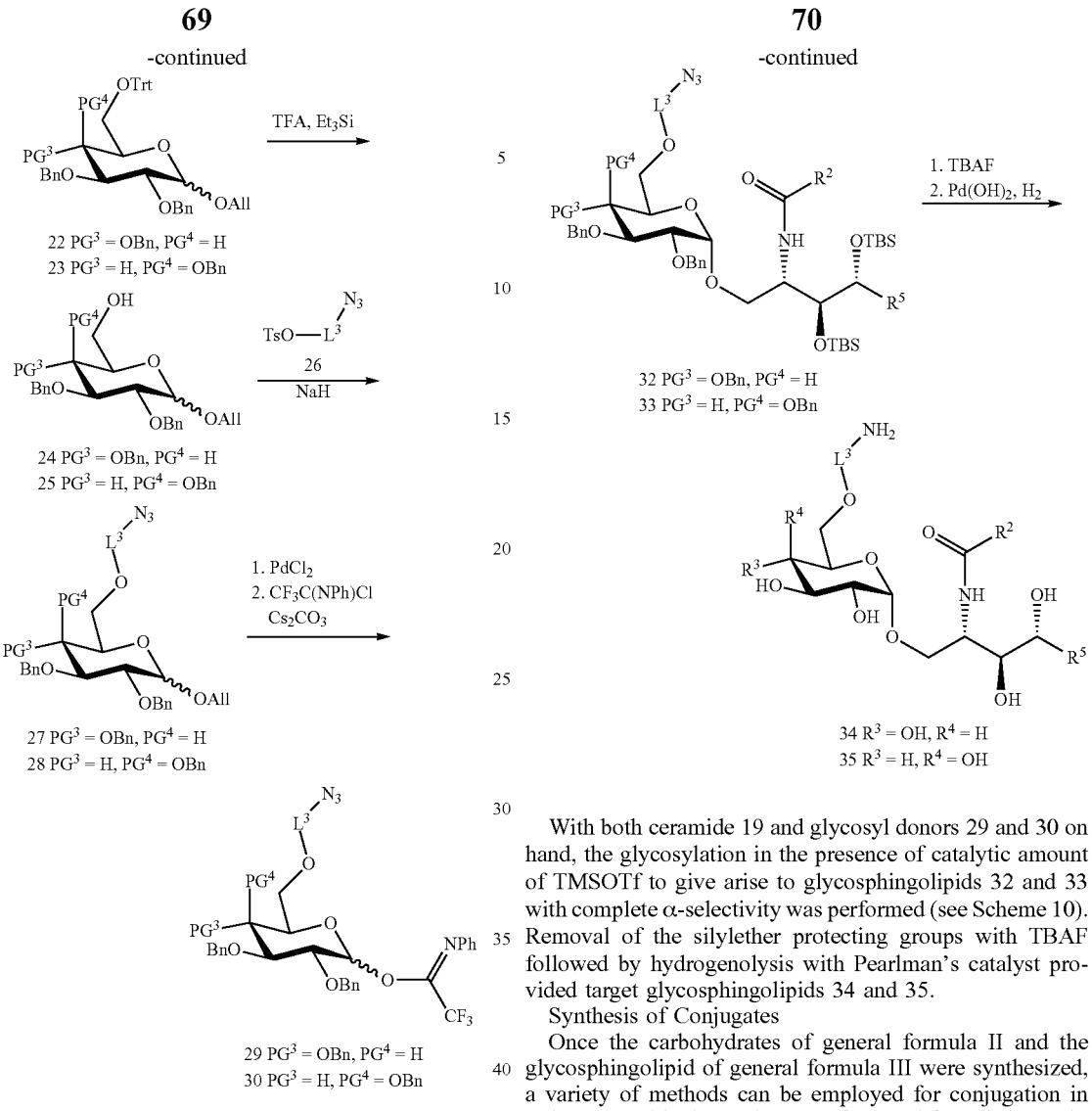

Building blocks 27 and 29 equipped at C6 with linker L³ having a terminal azido group were further subjected to isomerization of the anomeric allyl protecting group and hydrolysis to give intermediate lactols, which were converted to the glycosyl imidates 29 and 30 by reaction with 2,2,2-trifluoro-N-phenylacetimidoyl chloride in presence of cesium carbonate.

Scheme 9: Synthesis of azide 26.

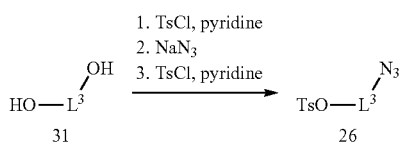

Scheme 10: Synthesis of glycosphingolipids 34 and 35.

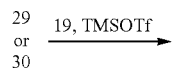

With both ceramide 19 and glycosyl donors 29 and 30 on hand, the glycosylation in the presence of catalytic amount of TMSOTf to give arise to glycosphingolipids 32 and 33 with complete α-selectivity was performed (see Scheme 10). Removal of the silylether protecting groups with TBAF followed by hydrogenolysis with Pearlman's catalyst provided target glycosphingolipids 34 and 35.

Synthesis of Conjugates

Once the carbohydrates of general formula II and the glycosphingolipid of general formula III were synthesized, a variety of methods can be employed for conjugation in order to provide the conjugates of general formula I. Methods for peptide bond formation based on the treatment of a carboxylic acid, which is pre-activated with an activating agent such as CDI, DCC, DIC or EDC, with an amine can be successfully applied for conjugating the carbohydrates of general formula II and the glycosphingolipid of general formula III. Additionally, schemes 11 and 12 sum up other conjugation methods; however the methods that can be used for connecting carbohydrate II and glycosphingolipid III, or for conjugating carbohydrate II to glycosphingolipid III are not restricted to the methods disclosed below.

For example, scheme 11 describes how carbohydrate II can be connected to glycosphingolipid III via a symmetric linker L² of general formula —C(O)—W—C(O)—. First glycosphingolipid III, which is functionalized at C6 of the galactose or glucose sugar moiety with a linker L³ presenting a terminal amino group is reacted with a activated diester 36 to provide activated monoester 37. In this case, the diester presents a 4-nitrophenol activating moiety. However, other activating moieties such as 2,4,5-trichlorophenyl, pentachlorophenyl, pentafluorophenyl, succinimido, 4-oxo-3,4-dihydrobenzo-triazin-3-yl, and sulfated moieties thereof can be considered as alternative for 4-nitrophenol activating moiety. The reaction is performed in slightly alkaline conditions (pH from 7.2 to 9) in a mixture of solvents containing 5-10% water-soluble solvent, such as DMF, pyridine or DMSO.

Once activated monoester 37 was obtained, the next step is the coupling with the carbohydrate of general formula II, which takes place in presence of pyridine to give target conjugate 38.

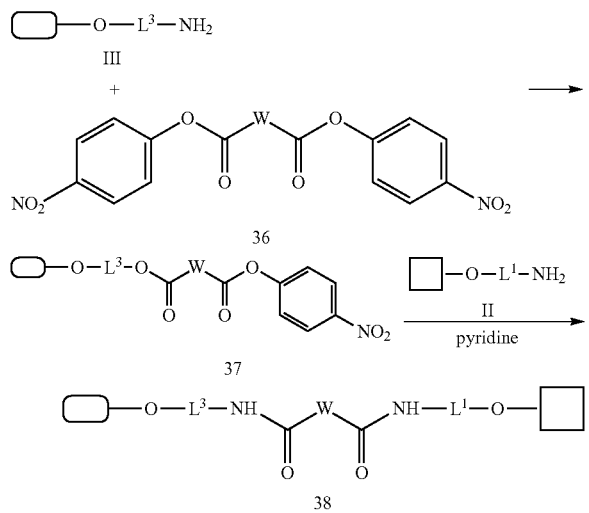

wherein

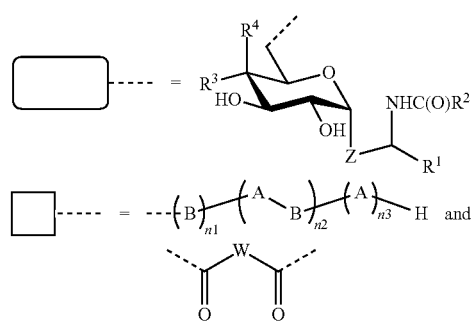

can be selected, but it is not restricted to one of the following fragments

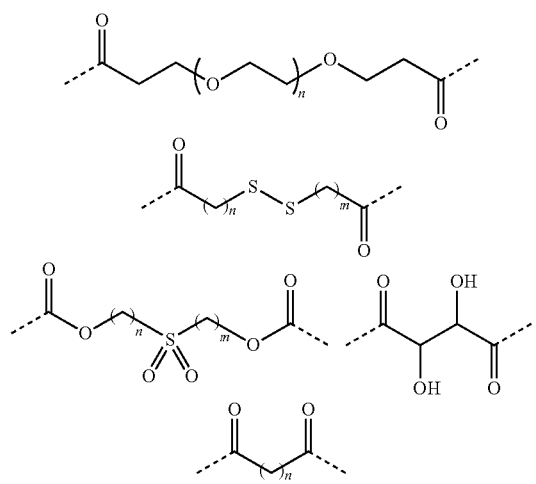

Scheme 11: Synthesis of Conjugate 38.

In case linker $L^2$ is asymmetric, a synthetic pathway such as the one presented by Scheme 12 could be followed. First, glycosphingolipid III is reacted with N-succinimide activated ester 39, to provide in presence of a base amide 40 equipped with a masked thiol group. In a similar manner, carbohydrate II is treated with activated ester 41 leading to amide 42 presenting a terminal maleimide. Cleavage of the acetate group in presence of ammonium hydroxide freed the primary thiol on compound 40 to provide an intermediate, which reacted with the terminal maleimide on compound 42 to give conjugate 43.

Scheme 12: Synthesis of conjugate 43.

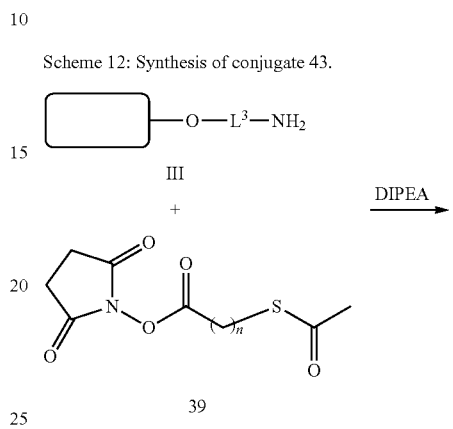

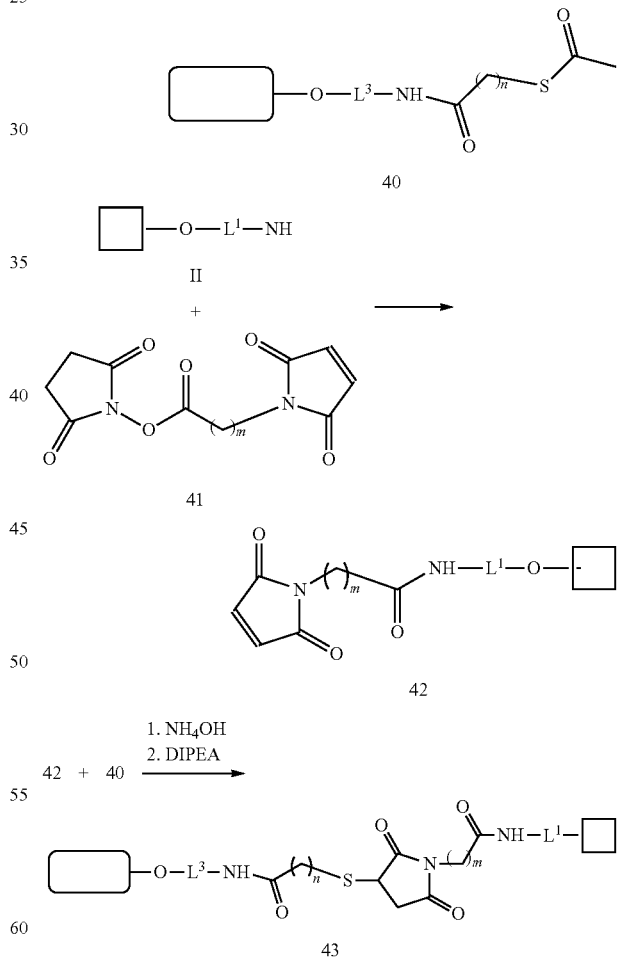

Obviously, the terminal maleimide could be installed on the glycosphingolipid of general formula III and the terminal thiol group could be installed on the carbohydrate of general formula II to generate conjugate 44.

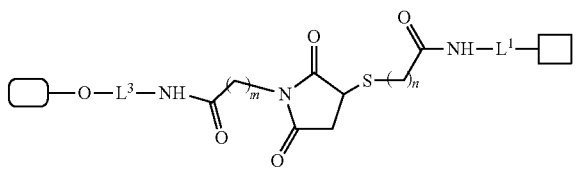

The terminal thiol generated from intermediate 40 could be also involved in a thiol-ene reaction with the appropriate alkene partner to provide conjugates of general formula I having a symmetric linker $L^2$ such as

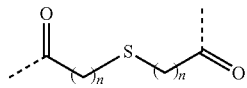

or an asymmetric one

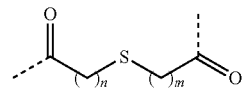

Figure 1:
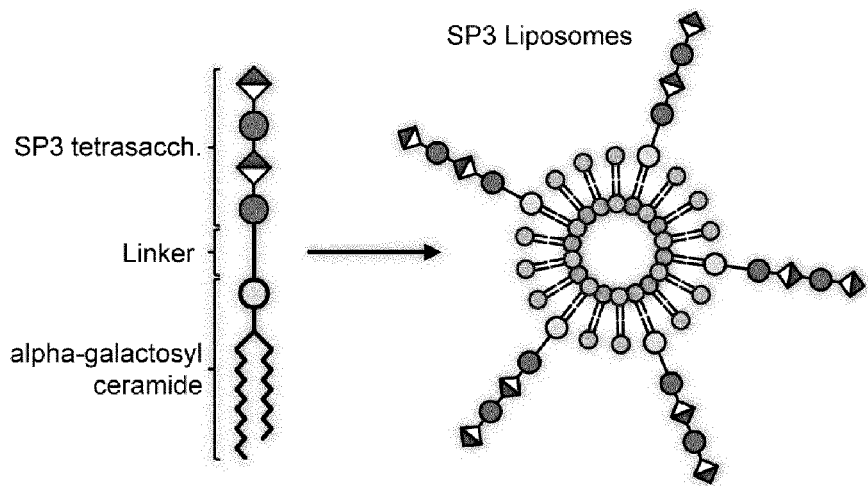
FIG. 1. Schematic representation of the liposome containing the conjugate 43* according to the present invention.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Chemical Synthesis
Abbreviations:
NIS: N-iodosuccinimide;
TfOH: triflic acid;
hr: hour;
DCM: dichloromethane;
TLC: thin layer chromatography;
MW: microwave
rt: room temperature;
RM: reaction mixture;
EtOAc: ethyl acetate;
MS: molecular sieves;
TMS: trimethylsilyl;
Tempo: 2,2,6,6-tetramethyl-1-piperidinyloxy, free radical;
BAIB: bis(acetoxy)iodobenzene;
HOBt: 1-Hydroxybenzotriazole.

General Information for Chemical Synthesis

Commercial reagents were used without further purification except where noted. Solvents were dried and redistilled prior to use in the usual way. All reactions were performed in oven-dried glassware under an inert atmosphere unless noted otherwise. Analytical thin layer chromatography (TLC) was performed on Kieselgel 60 F254 aluminium plates precoated with a 0.25 mm thickness of silica gel. The TLC plates were visualized with UV light and by staining with Hanessian solution (ceric sulfate and ammonium molybdate in aqueous sulfuric acid) or sulfuric acid-ethanol solution. Column chromatography was performed on Fluka Kieselgel 60 (230-400 mesh). Optical rotations (OR) were measured with a Schmidt & Haensch UniPol L1000 polarimeter at a concentration (c) expressed in g/100 mL. $^1$H and $^{13}$C NMR spectra were measured with a Varian 400-MR or Varian 600 spectrometer with $Me_4Si$ as the internal standard. NMR chemical shifts ($\delta$) were recorded in ppm and coupling constants (J) were reported in Hz. High-resolution mass spectra (HRMS) were recorded with an Agilent 6210 ESI-TOF mass spectrometer at the Freie Universitat Berlin, Mass Spectrometry Core Facility.

A. Synthesis of *Streptococcus pneumoniae* Type 3 Capsular Polysaccharide Related Carbohydrate Example A.1: Synthesis of (2R,4aR,6R,7R,8S,8aR)-6-(2-(benzyl((benzyloxy)carbonyl)amino)ethoxy)-2-phenylhexahydropyrano[3,2-d][1,3]dioxine-7,8-diyldibenzoate (1*)

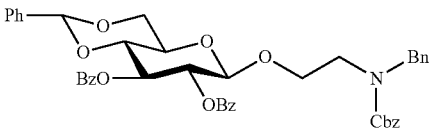

(2R,4aR,6S,7R,8S,8aR)-6-(ethylthio)-2-phenylhexahydropyrano[3,2-d][1,3]dioxine-7,8-diyldibenzoate (6.0 g, 11.53 mmol) and benzyl benzyl(2-hydroxyethyl)carbamate dried azeotropically using toluene in rotary evaporator (3.93 g, 13.83 mmol) were taken in dry DCM (100 mL) and added 5 g of microwave-dried 4 Å MS to it and stirred at rt for 15 min and then cooled to −10° C. After addition of NIS (3.83 g, 17.29 mmol) and TfOH (0.15 mL, 1.73 mmol), the reaction mixture under stirring was warmed from −10° C. to −5° C. during 1 hr. RM was then quenched with 10% aq. Na₂S₂O₃ solution (50 mL) and then extracted with EtOAc (25 ml×3). Combined organic layer was then washed with brine (10 ml), dried over anhydrous Na₂SO₄, filtered and concentrated in vacuum to get pale yellow oily compound. Crude product was purified on silica gel column chromatography using 20-30% EtOAc in hexanes to provide desired product 1* as pale yellow colored transparent gummy liquid (7.60 g, 89%).

¹H NMR (400 MHz, CDCl₃) δ 7.97 (dd, J=8.4, 1.2 Hz, 4H), 7.59-6.90 (m, 21H), 5.91-5.71 (m, 1H), 5.62-5.41 (m, 2H), 5.22-4.95 (m, 2H), 4.80 (d, J=7.7 Hz, 0.5H), 4.67 (d, J=7.7 Hz, 0.5H), 4.56-4.22 (m, 3H), 4.10-3.52 (m, 5H), 3.50-3.33 (m, 2H). ¹³C NMR (101 MHz, CDCl₃) δ 165.7, 165.4, 156.35, 156.2, 137.9, 136.9, 133.4, 133.2, 129.9, 129.5, 129.3, 129.1, 128.7, 128.5, 128.4, 128.3, 128.1, 127.8, 127.4, 127.2, 126.2, 101.9, 101.6, 78.9, 72.6, 72.1, 69.1, 68.7, 67.4, 67.2, 66.7, 51.7, 46.9, 45.8.

Example A.2: Synthesis of (2R,3R,4S,5R,6R)-2-(2-(benzyl((benzyloxy)carbonyl)amino)ethoxy)-6-((benzyloxy)methyl)-5-hydroxytetrahydro-2H-pyran-3,4-diyldibenzoate (2*)

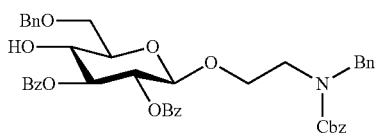

Glucose 1* (7.50 g, 10.08 mmol) was taken in DCM (75 mL) under argon with activated 3 Å MS for 10 min before cooling to 0° C. Triethylsilane (12.88 mL, 81.0 mmol), followed by TFA (4.66 mL, 60.5 mmol) were added dropwise and the RM was stirred at rt for 16 h before quenching with water (100 mL). The RM was extracted with DCM (30 mL×3), and the combined organic layers were washed thoroughly with water (20 mL×3), brine (20 mL), dried over anhydrous Na₂SO₄, filtered, evaporated in vacuum to get colorless gummy solid. The crude product was purified by silica column chromatography using 30%-100% EtOAc in hexanes to provide after evaporation in vacuum target compound as colorless oil (6.1 g, 81%).

¹H NMR (400 MHz, CDCl₃) δ 8.04-7.84 (m, 4H), 7.60-6.87 (m, 21H), 5.55-5.36 (m, 2H), 5.22-4.90 (m, 2H), 4.77-4.53 (m, 3H), 4.51-4.30 (m, 2H), 4.06-3.93 (m, 2H), 3.87-3.53 (m, 4H), 3.46-3.20 (m, 3H). ¹³C NMR (101 MHz, CDCl₃) δ 167.3, 165.5, 138.0, 137.7, 133.6, 130.1, 129.9, 128.6, 128.5, 128.1, 127.9, 127.8, 127.4, 101.3, 101.2, 76.7, 74.7, 73.9, 71.6, 71.5, 71.2, 70.0, 69.0, 67.4, 67.2, 51.7, 46.8, 45.8.

Example A.3: Synthesis of (2R,3R,4S,5R,6R)-5-(((2R,4aR,6S,7R,8S,8aR)-7-(benzoyloxy)-8-((tert-butyldimethylsilyl)oxy)-2-phenylhexahydropyrano[3,2-d][1,3]dioxin-6-yl)oxy)-2-(2-(benzyl((benzyloxy)carbonyl)amino)ethoxy)-6-((benzyloxy)methyl)tetrahydro-2H-pyran-3,4-diyldibenzoate (3*)

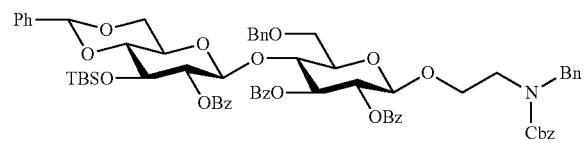

(2R,3R,4S,5R,6R)-2-(2-(benzyl((benzyloxy)carbonyl)amino)ethoxy)-6-((benzyloxy)methyl)-5-hydroxytetrahydro-2H-pyran-3,4-diyldibenzoate (2.0 g, 2.68 mmol) was taken in DCM (30 mL) with activated 4 Å acid washed MS and stirred at rt for 30 min before cooling to 0° C. TMSOTf (0.49 μL, 0.27 mmol) was then added followed by the (2R,4aR,6S,7R,8S,8aR)-8-((tert-butyldimethylsilyl)oxy)-2-phenyl-6-(2,2,2-trichloro-1-iminoethoxy)hexahydropyrano[3,2-d][1,3]dioxin-7-yl benzoate (2.20 g, 3.89 mmol) in DCM (5 mL) over 5 min and the reaction mixture was stirred for 30 min at 0° C. The RM was quenched with Et₃N (1 mL), filtered and the solvents removed under vacuum. The crude product was purified by flash chromatography using EtOAc in hexanes to get product 3* (3.2 g, 98%).

¹H NMR (400 MHz, cdcl₃) δ 8.13-6.88 (m, 35H), 5.67-5.52 (m, 1H), 5.46-5.31 (m, 1H), 5.20 (s, 1H), 5.16-4.89 (m, 3H), 4.68 (t, J=11.2 Hz, 1H), 4.55 (d, J=8.1 Hz, 1.5H), 4.47-4.24 (m, 3.5H), 4.20-3.89 (m, 1.5H), 3.89-3.19 (m, 9.5H), 3.13 (td, J=9.7, 4.9 Hz, 1H), 2.63 (t, J=10.2 Hz, 1H), 0.63 (s, 9H), −0.12 (s, 3H), −0.19 (s, 3H). ¹³C NMR (101 MHz, CDCl₃) δ 165.4, 165.36, 164.7, 138.2, 137.1, 133.4, 133.2, 129.94, 129.9, 129.2, 128.7, 128.6, 128.5, 128.4, 128.2, 128.0, 127.8, 127.3, 126.4, 101.7, 101.2, 101.1, 81.2, 75.5, 75.1, 74.6, 73.7, 73.4, 73.0, 68.9, 68.0, 67.3, 66.1, 51.7, 46.9, 25.6, 18.0, −4.1, −4.8.

Example A.4: Synthesis of (2R,3R,4S,5R,6R)-5-(((2R,4aR,6S,7R,8S,8aS)-7-(benzoyloxy)-8-hydroxy-2-phenylhexahydropyrano[3,2-d][1,3]dioxin-6-yl)oxy)-2-(2-(benzyl((benzyloxy)carbonyl)amino)ethoxy)-6-((benzyloxy)methyl)tetrahydro-2H-pyran-3,4-diyldibenzoate (4*)

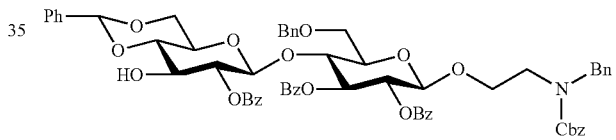

(2R,3R,4S,5R,6R)-5-(((2R,4aR,6S,7R,8S,8aR)-7-(benzoyloxy)-8-((tert-butyl dimethylsilyl)oxy)-2-phenylhexahydropyrano[3,2-d][1,3]dioxin-6-yl)oxy)-2-(2-(benzyl((benzyloxy)carbonyl)amino)ethoxy)-6-((benzyloxy)methyl)tetrahydro-2H-pyran-3,4-diyldibenzoate (1.6 g, 1.317 mmol) was taken in pyridine (10 mL) at 0° C. and treated with HF-pyridine (3.56 mL, 39.5 mmol). The mixture was stirred at rt for 24 h. RM was washed with water and extracted with DCM (20 mL×3). Combined organic layers were then washed with diluted HCl (50 mL×2), saturated NaHCO₃ solution (50 mL), brine (10 mL), dried over Na₂SO₄, filtered and concentrated in vacuum to get crude product, which after purification using silica column chromatography using 35-40% EtOAc in hexanes yielded target compound as white colored foam (1.3 g, 90%).

¹H NMR (400 MHz, CDCl₃) δ 8.15-6.92 (m, 1H), 5.65-5.51 (m, 1H), 5.44-5.30 (m, 1H), 5.23 (s, 1H), 5.11-5.04 (m, 3H), 4.77-4.49 (m, 3H), 4.49-4.24 (m, 4H), 4.25-3.91 (m, 2H), 3.91-3.59 (m, 4H), 3.57-3.00 (m, 7H), 2.68 (t, J=10.3 Hz, 1H). ¹³C NMR (101 MHz, CDCl₃) δ 165.4, 165.3, 156.4, 156.2, 138.2, 136.9, 133.6, 133.2, 130.3, 130.0, 129.9, 129.4, 128.7, 128.7, 128.5, 128.5, 128.4, 128.1, 128.1, 127.8, 127.4, 126.4, 101.8, 101.2, 101.1, 80.6, 75.9, 74.9, 74.7, 73.7, 73.5, 72.6, 72.0, 71.9, 68.9, 67.9, 67.4, 67.2, 66.0, 51.7, 46.9, 45.9.

Example A.5: Synthesis of (2S,3R,4S,5R,6R)-2-(((2R,4aR,6S,7R,8S,8aR)-7-(benzoyloxy)-6-(((2R,3R,4S,5R,6R)-4,5-bis(benzoyloxy)-6-(2-(benzyl((benzyloxy)carbonyl)amino)ethoxy)-2-((benzyloxy)methyl)tetrahydro-2H-pyran-3-yl)oxy)-2-phenylhexahydropyrano[3,2-d][1,3]dioxin-8-yl)oxy)-5-(((2R,4aR,6S,7R,8S,8aR)-7-(benzoyloxy)-8-((tert-butyldimethylsilyl)oxy)-2-phenylhexahydropyrano[3,2-d][1,3]dioxin-6-yl)oxy)-6-((benzyloxy)methyl)tetrahydro-2H-pyran-3,4-diyldibenzoate (5*)

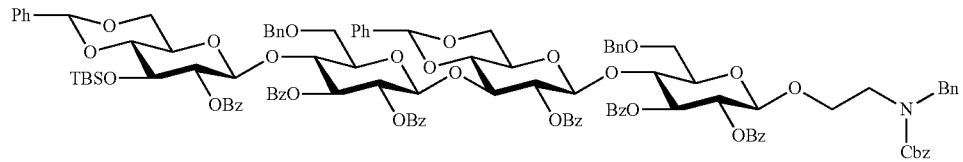

Acceptor 4* (1.0 g, 0.91 mmol), (2S,3R,4S,5R,6R)-5-(((2R,4aR,6S,7R,8S,8aR)-7-(benzoyloxy)-8-((tert-butyldimethylsilyl)oxy)-2-phenylhexahydropyrano[3,2-d][1,3]dioxin-6-yl)oxy)-6-((benzyloxy)methyl)-2-(ethylthio)tetrahydro-2H-pyran-3,4-diyldbenzoate (12*) (1.08 g, 1.091 mmol) and 20 g of dried 4 Å MS were taken in DCM (30 mL), stirred at rt for 15 min and then cooled to −10° C. NIS (0.245 g, 1.09 mmol) and TfOH (0.016 mL, 0.18 mmol) were then added and the reaction mixture was for 1 h stirred at −5° C. (2S,3R,4S,5R,6R)-5-(((2R,4aR,6S,7R,8S,8aR)-7-(benzoyloxy)-8-((tert-butyldimethylsilyl)oxy)-2-phenylhexahydropyrano[3,2-d][1,3]dioxin-6-yl)oxy)-6-((benzyloxy)methyl)-2-(ethylthio)tetrahydro-2H-pyran-3,4-diyl dibenzoate (0.45 g, 0.454 mmol, 0.5 equiv.) and NIS (0.102 mg, 0.454 mmol, 0.5 equiv.) were added again to the reaction mixture and stirred at −5° C. for 1 h, then warmed to 5° C. After filtration through a Celite® bed, the RM was quenched with 10% Na$_2$S$_2$O$_3$ solution (25 mL) and then extracted with DCM (15 ml×3). Combined organic layers were then washed with sat. NaHCO$_3$ solution (15 mL), brine (10 ml), dried over anhydrous Na$_2$SO$_4$, filtered and concentrated in vacuum to get white colored fluffy solid compound. Crude product was purified by silica column chromatography using 30-35% EtOAc in hexanes to get target 5* as fluffy white solid (1.0 g, 54%).

$^1$H NMR (400 MHz, CDCl$_3$) δ 8.05-6.87 (m, 60H), 5.57-5.40 (m, 1H), 5.39-5.24 (m, 2H), 5.21-4.86 (m, 7H), 4.60 (d, J=7.9 Hz, 1H), 4.54-4.15 (m, 9H), 4.07-3.85 (m, 3H), 3.81-3.70 (m, 3H), 3.60 (dd, J=10.6, 4.8 Hz, 1H), 3.52 (dd, J=10.6, 4.9 Hz, 1H), 3.47-3.14 (m, 9H), 3.13-2.96 (m, 3H), 2.64 (t, J=10.4 Hz, 1H), 2.55 (t, J=10.3 Hz, 1H), 0.58 (s, 9H), −0.18 (s, 3H), −0.26 (s, 3H). $^{13}$C NMR (101 MHz, CDCl$_3$) δ 165.4, 165.1, 164.9, 164.5, 164.0, 156.4, 156.2, 138.4, 138.1, 137.1, 137.0, 133.2, 133.0, 132.6, 130.3, 130.1, 130.0, 129.96, 129.9, 129.8, 129.4, 129.1, 128.6, 128.5, 128.51, 128.4, 128.3, 128.2, 128.15, 128.1, 128.06, 128.0, 127.8, 127.3, 126.4, 126.1, 101.7, 101.5, 101.2, 101.18, 101.0, 100.2, 81.1, 79.5, 77.4, 75.9, 75.6, 75.1, 74.4, 73.7, 73.5, 73.4, 73.2, 72.4, 68.8, 67.9, 67.3, 66.2, 66.0, 51.7, 46.9, 45.9, 21.2, 17.9, −4.1, −4.9.

Example A.6: Synthesis of (2S,3R,4S,5R,6R)-2-(((2R,4aR,6S,7R,8S,8aR)-7-(benzoyloxy)-6-(((2R,3R,4S,5R,6R)-4,5-bis(benzoyloxy)-6-(2-(benzyl((benzyloxy)carbonyl)amino)ethoxy)-2-((benzyloxy)methyl)tetrahydro-2H-pyran-3-yl)oxy)-2-phenylhexahydropyrano[3,2-d][1,3]dioxin-8-yl)oxy)-5-(((2R,4aR,6S,7R,8S,8aS)-7-(benzoyloxy)-8-hydroxy-2-phenylhexahydropyrano[3,2-d][1,3]dioxin-6-yl)oxy)-6-((benzyloxy)methyl)tetrahydro-2H-pyran-3,4-diyldibenzoate (6*)

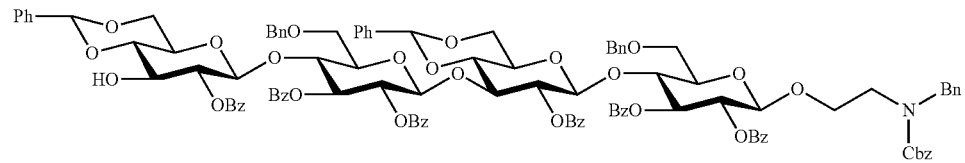

Tetrasaccharide 5* (1.0 g, 0.493 mmol) was taken in pyridine (10 mL) at 0° C. and added HF-pyridine (1.33 mL, 14.78 mmol) to it and stirred at rt for 36 hrs. The RM was washed with water and extracted with DCM (20 mL×3). Combined organic layers were then washed with cold diluted HCl (50 mL×2), saturated NaHCO$_3$ solution (50 mL), brine (10 mL), dried over Na$_2$SO$_4$, filtered and concentrated in vacuum to get crude product, which after purification on silica column chromatography using 50% EtOAc in hexanes yielded target compound as a white colored foam (0.71 g, 75%).

$^1$H NMR (400 MHz, CDCl$_3$) δ 8.07-6.94 (m, 60H), 5.56-5.41 (m, 1H), 5.37-5.23 (m, 2H), 5.22-5.14 (m, 2H), 5.13-5.02 (m, 2H), 5.02-4.91 (m, 3H), 4.60 (dd, J=7.9, 3.5 Hz, 2H), 4.56-4.48 (m, 1H), 4.46 (d, J=7.9 Hz, 1H), 4.43-4.24 (m, 4H), 4.20 (d, J=12.1 Hz, 2H), 4.09-3.88 (m, 3H), 3.85-3.70 (m, 3H), 3.61 (dd, J=10.6, 4.7 Hz, 1H), 3.54-3.31 (m, 5H), 3.31-3.15 (m, 5H), 3.16-2.97 (m, 3H), 2.65 (t, J=10.4 Hz, 1H), 2.56 (t, J=10.4 Hz, 1H), 2.38 (d, J=3.5 Hz, 1H). $^{13}$C NMR (101 MHz, CDCl$_3$) δ 165.3, 165.2, 165.0, 164.9, 164.7, 163.9, 138.2, 137.9, 136.8, 136.8, 133.4, 133.0, 132.5, 130.0, 129.9, 129.8, 129.7, 129.6, 129.5, 129.2, 129.0, 128.5, 128.4, 128.35, 128.3, 128.1, 128.0, 127.97, 127.9, 127.8, 127.7, 127.2, 126.2, 126.0, 101.6, 101.3, 101.0, 100.9, 100.8, 100.0, 80.4, 79.3, 78.3, 77.2, 76.6, 76.0, 75.5, 74.8, 74.3, 73.6, 73.2, 72.3, 72.1, 68.7, 67.6, 67.2, 66.1, 65.7, 51.5, 46.7, 45.7.

Example A.7: Synthesis of (2S,3R,4S,5R,6R)-2-(((2R,4aR,6S,7R,8S,8aR)-7-(benzoyloxy)-6-(((2R,3R,4S,5R,6R)-4,5-bis(benzoyloxy)-6-(2-(benzyl((benzyloxy)carbonyl)amino)ethoxy)-2-((benzyloxy)methyl)tetrahydro-2H-pyran-3-yl)oxy)-2-phenylhexahydropyrano[3,2-d][1,3]dioxin-8-yl)oxy)-6-((benzyloxy)methyl)-5-(((2R,4aR,6S,7R,8S,8aR)-7,8-bis(benzoyloxy)-2-phenylhexahydropyrano[3,2-d][1,3]dioxin-6-yl)oxy)tetrahydro-2H-pyran-3,4-diyldibenzoate (7*)

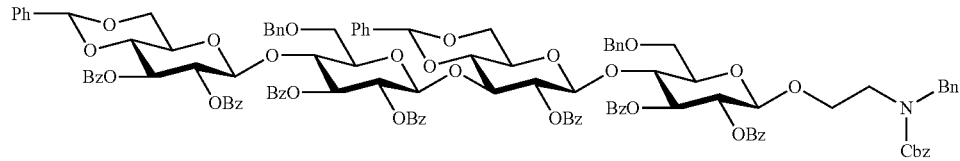

Tetrasaccharide 6* (0.65 g, 0.339 mmol) was taken in pyridine (5 mL), treated with BzCl (0.79 mL, 0.679 mmol) and stirred at rt for 16 hrs. The RM was diluted with water and extracted with DCM (20 mL×3). Combined organics were washed with cold diluted HCl (10 mL×2), saturated NaHCO$_3$ (10 mL×2), water (10 mL), brine (20 mL), dried over Na$_2$SO$_4$, filtered, and concentrated in vacuum to get crude product, which was then triturated using cold MeOH (5 mL×3) to get target 7* as white solid (0.65 g, 95%).

$^1$H NMR (400 MHz, CDCl$_3$) δ 8.10-6.92 (m, 65H), 5.55-5.41 (m, 2H), 5.40-5.15 (m, 4H), 5.13-4.96 (m, 4H), 4.93 (s, 1H), 4.67 (d, J=7.9 Hz, 1H), 4.61 (d, J=7.9 Hz, 1H), 4.55-4.47 (m, 1H), 4.45 (d, J=7.9 Hz, 1H), 4.43-4.16 (m, 6H), 4.10-3.86 (m, 3H), 3.84-3.72 (m, 1H), 3.65-3.34 (m, 6H), 3.33-3.15 (m, 6H), 3.11-3.06 (m, 3H), 2.67-2.59 (m, 2H). $^{13}$C NMR (101 MHz, CDCl$_3$) δ 165.6, 165.4, 165.2, 165.1, 164.8, 164.0, 156.3, 156.2, 138.1, 138.1, 138.0, 137.0, 136.8, 133.4, 133.1, 132.7, 130.2, 129.9, 129.9, 129.8, 129.8, 129.7, 129.5, 129.3, 129.3, 129.2, 129.1, 128.6, 128.6, 128.6, 128.5, 128.4, 128.35, 128.3, 128.2, 128.16, 128.1, 127.8, 127.3, 126.2, 126.1, 125.4, 101.5, 101.3, 101.2, 101.0, 100.1, 79.5, 78.4, 77.4, 76.3, 75.6, 74.3, 73.7, 73.5, 73.4, 73.1, 72.3, 72.3, 72.3, 68.8, 68.0, 67.8, 67.1, 66.24, 66.2, 51.7, 46.9, 45.8.

Example A.8: Synthesis of (2S,3R,4S,5R,6R)-2-(((2S,3R,4S,5R,6R)-3-(benzoyloxy)-2-(((2R,3R,4S,5R,6R)-4,5-bis(benzoyloxy)-6-(2-(benzyl((benzyloxy)carbonyl)amino)ethoxy)-2-((benzyloxy)methyl)tetrahydro-2H-pyran-3-yl)oxy)-5-hydroxy-6-(hydroxymethyl)tetrahydro-2H-pyran-4-yl)oxy)-6-((benzyloxy)methyl)-5-(((2S,3R,4S,5R,6R)-3,4-bis(benzoyloxy)-5-hydroxy-6-(hydroxymethyl)tetrahydro-2H-pyran-2-yl)oxy)tetrahydro-2H-pyran-3,4-diyldibenzoate (8*)

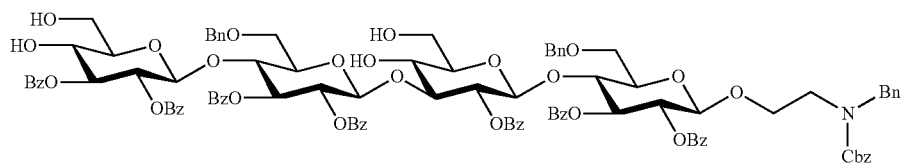

Tetrasaccharide 7* (0.54 g, 0.267 mmol) was taken in DCM (5 mL) at rt, treated with PTSA (10 mg, 0.053 mmol) and EtSH (0.297 mL, 4.01 mmol), and stirred for 4 hrs. The RM was quenched with Et$_3$N (1 mL), evaporated in vacuum and purified using 60% EtOAc in hexanes to get target 8* as white colored solid product (0.46 g, 93%).

$^1$H NMR (400 MHz, CDCl$_3$) δ 8.02-7.81 (m, 10H), 7.59-6.91 (m, 45H), 5.52 (t, J=9.2 Hz, 1H), 5.47-5.15 (m, 5H), 5.12-4.90 (m, 3H), 4.62 (d, J=7.6 Hz, 1H), 4.61-4.57 (m, 1H), 4.52 (d, J=7.7 Hz, 1H), 4.47-4.36 (m, 3H), 4.34-4.18 (m, 4H), 4.13-3.99 (m, 2H), 3.95-3.73 (m, 2H), 3.69 (td, J=9.1, 4.3 Hz, 1H), 3.61-3.50 (m, 3H), 3.27 (m, 1H), 3.11-2.95 (m, 3H), 2.89 (d, J=4.3 Hz, 1H). $^{13}$C NMR (101 MHz, CDCl$_3$) δ 167.4, 165.36, 165.23, 165.2, 165.2, 164.9, 163.8, 156.3, 156.2, 138.1, 137.3, 133.7, 133.6, 133.3, 133.0, 132.7, 130.1, 130.0, 129.9, 129.8, 129.7, 129.6, 129.51, 129.5, 129.2, 129.0, 128.9, 128.8, 128.7, 128.69, 128.6, 128.5, 128.4, 128.3, 128.13, 128.1, 127.8, 127.3, 127.2, 101.3, 101.1, 100.8, 100.3, 85.1, 77.4, 77.0, 76.0, 75.8, 74.8, 74.7, 74.4, 73.8, 73.6, 73.3, 72.2, 71.7, 71.7, 69.4, 69.3, 68.9, 67.6, 67.1, 62.5, 61.6, 51.7, 46.9, 45.9. MALDI-TOF: calculated for C$_{104}$H$_{99}$NNaO$_{30}$ [M+H]$^+$, 1864.61, found 1864.77.

Example A.9: Synthesis of (2S,3S,4S,5R,6R)-4,5-bis(benzoyloxy)-6-(((2R,3R,4S,5R,6S)-4,5-bis(benzoyloxy)-6-(((2R,3R,4S,5S,6S)-3-(benzoyloxy)-2-(((2R,3R,4S,5R,6R)-4,5-bis(benzoyloxy)-6-(2-(benzyl((benzyloxy)carbonyl)amino)ethoxy)-2-((benzyloxy)methyl)tetrahydro-2H-pyran-3-yl)oxy)-6-carboxy-5-hydroxytetrahydro-2H-pyran-4-yl)oxy)-2-((benzyloxy)methyl)tetrahydro-2H-pyran-3-yl)oxy)-3-hydroxytetrahydro-2H-pyran-2-carboxylic acid (9*)

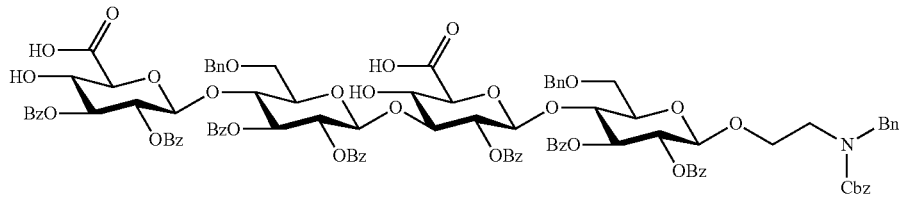

Tetrasaccharide 8* (0.125 g, 0.068 mmol) was taken in a mixture DCM/water (7 ml, 5:2) and cooled to 0° C. After addition of tempo (2.1 mg, 0.014 mmol), followed by BAIB (0.109 g, 0.339 mmol), the RM was stirred at 0° C. for 20 min and slowly warmed up to rt and further stirred at rt for 2 h (total 3 h). The RM was diluted with DCM (5 mL) and water (5 mL), and the layers were separated. The aqueous layer was extracted with DCM (5 mL×4). The combined organic layers were dried over $Na_2SO_4$, filtered, concentrated in vacuum to provide the crude product, which was then purified on silica column using 10-15% acetone in DCM+1-2% AcOH to yield after evaporation desired product 9* as a yellowish solid (0.09 g, 71%).

$^1$H NMR (400 MHz, $CD_3OD$) δ 8.00-6.52 (m, 55H), 5.61-5.29 (m, 3H), 5.27-5.05 (m, 3H), 4.99 (d, J=9.8 Hz, 1H), 4.94 (d, J=8.0 Hz, 1H), 4.88-4.83 (m, 2H), 4.76 (d, J=7.9 Hz, 1H), 4.53 (d, J=8.0 Hz, 1.5H), 4.43 (dd, J=12.1, 4.8 Hz, 1H), 4.37 (d, J=7.8 Hz, 0.5H), 4.33-4.02 (m, 7H), 3.87-3.39 (m, 11H), 3.26-3.03 (m, 4H). $^{13}$C NMR (101 MHz, $CD_3OD$) δ 170.4, 170.35, 167.2, 167.18, 166.9, 166.7, 166.5, 166.4, 165.7, 158.0, 157.7, 139.2, 138.8, 138.6, 134.8, 134.5, 134.4, 134.1, 134.0, 131.4, 130.8, 130.8, 130.7, 130.6, 130.5, 130.3, 130.1, 129.8, 129.7, 129.53, 129.5, 129.4, 129.3, 129.2, 129.1, 128.8, 128.6, 128.2, 102.2, 101.9, 101.8, 101.7, 84.2, 77.6, 76.7, 76.4, 75.4, 74.6, 74.4, 73.7, 73.5, 73.3, 71.5, 71.1, 69.5, 69.4, 68.5, 68.31, 68.3, 52.6, 52.5, 47.10. MALDI-TOF: calculated for $C_{104}H_{95}NO_{32}$ [M+H]$^+$, 1892.57, found 1892.71.

Example A.10: Synthesis of (2S,3S,4S,5R,6R)-6-(((2R,3S,4R,5R,6R)-6-(2-(benzyl((benzyloxy)carbonyl)amino)ethoxy)-2-((benzyloxy)methyl)-4,5-dihydroxytetrahydro-2H-pyran-3-yl)oxy)-4-(((2S,3R,4R,5S,6R)-6-((benzyloxy)methyl)-5-(((2R,3R,4S,5S,6S)-6-carboxy-3,4,5-trihydroxytetrahydro-2H-pyran-2-yl)oxy)-3,4-dihydroxytetrahydro-2H-pyran-2-yl)oxy)-3,5-dihydroxytetrahydro-2H-pyran-2-carboxylic acid (10*)

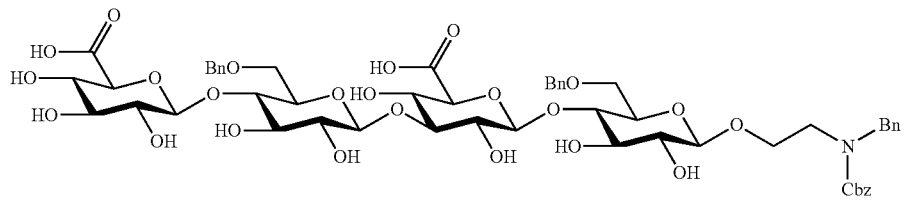

Tetrasaccharide 9* (0.09 g, 0.48 mmol) was taken in MeOH (5 mL), treated with 0.5 M solution NaOMe in methanol (4.81 mL, 2.405 mmol) and stirred at rt for 24 hrs. The RM was then neutralized with Amberlite® 120H$^+$ resin to give a clear solution, which was filtered through a cotton plug, washed thoroughly with MeOH and evaporated in vacuum to give a yellowish gum. The yellowish gum was taken in diethyl $Et_2O$ and triturated to provide a pale yellowish solid. The ether layer was then decanted (3×3 ml). The pale yellowish solid was triturated with DCM to give a white solid, which was then dried under vacuum to yield target 10* as white powder (0.05 g, 91%). $^1$H NMR (400 MHz, $CD_3OD$) δ 7.49-7.06 (m, 20H), 5.14 (d, J=9.5 Hz, 2H), 4.68-4.51 (m, 6H), 4.47-4.37 (m, 3H), 4.27-4.17 (m, 1H), 3.96-3.34 (m, 23H), 3.30-3.19 (m, 2H). LCMS (ESI): calculated for $C_{55}H_{66}NO_{25}$ [M−H]$^+$, 1140.39, found 1140.2.

Example A.11: Synthesis of (2S,3S,4S,5R,6R)-6-(((2R,3S,4R,5R,6R)-6-(2-aminoethoxy)-4,5-dihydroxy-2-(hydroxymethyl)tetrahydro-2H-pyran-3-yl)oxy)-4-(((2S,3R,4R,5S,6R)-5-(((2R,3R,4S,5S,6S)-6-carboxy-3,4,5-trihydroxytetrahydro-2H-pyran-2-yl)oxy)-3,4-dihydroxy-6-(hydroxymethyl)tetrahydro-2H-pyran-2-yl)oxy)-3,5-dihydroxytetrahydro-2H-pyran-2-carboxylic acid (11*)

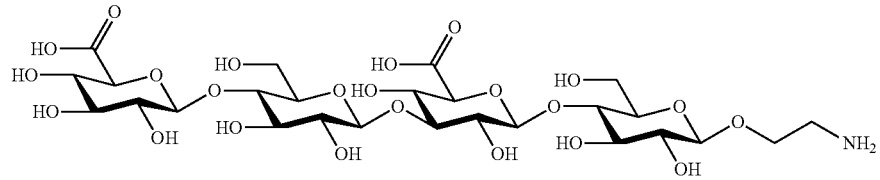

A mixture of tetrasaccharide 10* (50 mg) and 10% Pd/C (100 mg) in MeOH (2 mL) was stirred at rt under hydrogen for 18 h. The RM was then filtered through PTFE hydrophobic filters and washed thoroughly with methanol, water-methanol, and later with NH₄OH in methanol. Evaporation of the filtrate and drying under vacuum provided target 11* as white glassy film (23 mg, 71%).

$^1$H NMR (400 MHz, D$_2$O) δ 4.84 (d, J=8.0 Hz, 1H), 4.56 (d, J=8.0 Hz, 2H), 4.53 (d, J=7.9 Hz, 1H), 4.14 (dt, J=11.5, 4.9 Hz, 1H), 4.04-3.92 (m, 3H), 3.89-3.75 (m, 5H), 3.72-3.49 (m, 10H), 3.43-3.34 (m, 3H), 3.29 (t, J=5.1 Hz, 2H). $^{13}$C NMR (101 MHz, D$_2$O) δ 175.4, 175.2, 102.3, 102.2, 102.0, 101.8, 82.7, 78.9, 78.6, 75.7, 75.2, 74.8, 74.7, 74.1, 73.1, 72.9, 72.7, 71.6, 70.1, 65.7, 60.0 39.3. HRMS (ESI): calculated for $C_{26}H_{44}NO_{23}$ [M+H]$^+$, 738.23, found 738.27.

Tetrasaccharides 11*a-11*c were synthesized by applying the procedures described in examples A.1 to A.11 to benzyl benzyl(3-hydroxypropyl)carbamate, benzyl benzyl(4-hydroxybuthyl)carbamate and benzyl benzyl(5-hydroxypentyl)carbamate.

11*a

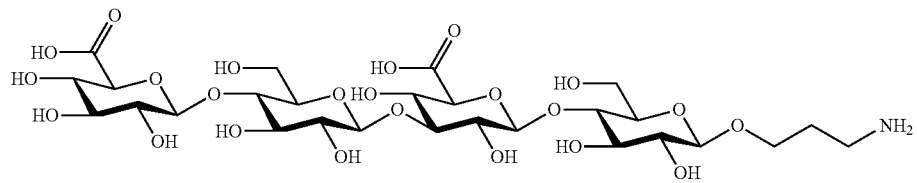

HRMS (ESI): calculated for $C_{27}H_{45}NO_{23}$ [M+H]$^+$, 752.23, found 752.21.

11*b

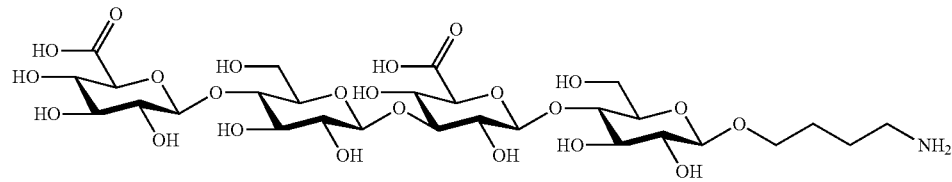

HRMS (ESI): calculated for $C_{28}H_{47}NO_{23}$ [M+H]$^+$, 766.25, found 766.21.

11*c

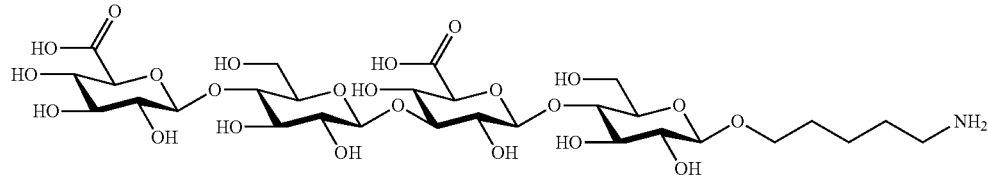

HRMS (ESI): calculated for $C_{29}H_{49}NO_{23}$ [M+H]$^+$, 780.26, found 780.24.

Example A.12: Synthesis of (2S,3R,5R,6R)-5-(((4aR,6S,7R,8S,8aR)-7-(benzoyloxy)-8-((tert-butyldimethylsilyl)oxy)-2-phenylhexahydropyranophenyl hexahydropyrano[3,2-d][1,3]dioxin-6-yl)oxy)-6-((benzyloxy)methyl)-2-(ethylthio)tetrahydro-2H-pyran-3,4-diyldibenzoate (12*)

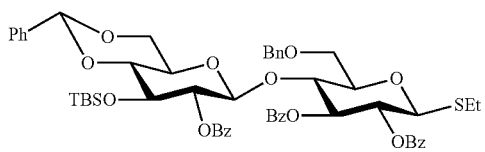

A mixture of (2S,3R,4S,5R,6R)-6-((benzyloxy)methyl)-2-(ethylthio)-5-hydroxytetrahydro-2H-pyran-3,4-diyl dibenzoate (4.00 g, 7.654 mmol, 1.0 eq.) and (4a R,6R,7R,8a R)-8-((tert-butyldimethylsilyl)oxy)-2-phenyl-6-(2,2,2-trichloro-1-iminoethoxy)hexahydropyrano[3,2-d][1,3]dioxin-7-yl benzoate (6.28 g, 9.95 mmol, 1.3 eq.) in DCM (140 mL) was stirred under an Ar atmosphere for 30 min. The reaction mixture was cooled (−20° C.) and TMSOTf (0.16 mL, 0.880 mmol, 0.115 eq.) was added. After stirring for 45 min, the reaction mixture was quenched by the addition of Et$_3$N (1.0 mL). The organic solution was concentrated under vacuo. The resulting dark yellow oil was purified by flash chromatography over silica gel (EtOAc/hexanes, 1/3, v/v) to give (2S,3R,5R,6R)-5-(((4aR,6S,7R,8S,8aR)-7-(benzoyloxy)-8-((tert-butyldimethylsilyl)oxy)-2-phenylhexahydro pyranophenylhexahydropyrano[3,2-d][1,3]dioxin-6-yl)oxy)-6-((benzyloxy)methyl)-2-(ethylthio) tetrahydro-2H-pyran-3,4-diyl dibenzoate 12* (6 g, 79%) as a colorless solid:

R$_f$=0.5 (EtOAc/hexanes, 3/7, v/v). $^1$H NMR (400 MHz, CDCl$_3$) δ −0.19 (s, 3H), −0.11 (s, 3H), 0.63 (s, 9H), 1.20 (t, J=7.4 Hz, 3H), 2.67 (m, 2H), 3.15 (td, J=9.7 Hz, 4.9 Hz, 2H), 3.28 (t, J=9.2 Hz, 1H), 3.53-3.37 (m, 1H), 3.74-3.55 (m, 1H), 3.79 (t, J=9.0 Hz, 1H), 4.19 (t, J=9.5 Hz, 1H), 4.37 (d, J=12.2 Hz, 1H), 4.57 (d, J=10.0 Hz, 1H), 4.59 (dd, J=15.1, 9.0 Hz, 2H), 4.67 (d, J=12.2 Hz, 1H), 5.12 (dd, J=8.9, 8.2 Hz, 1H), 5.21 (s, 1H), 5.41 (t, J=9.8 Hz, 1H), 5.63 (t, J=9.3 Hz, 1H), 7.29-7.72 (m, 19H), 7.88-8.03 (m, 6H). $^{13}$C NMR (101 MHz, CDCl$_3$) δ 165.27, 165.07, 164.45, 138.16, 137.00, 133.14, 133.10, 132.97, 130.21, 129.79, 129.77, 129.75, 129.34, 128.99, 128.51, 128.38, 128.28, 128.22, 128.05, 128.02, 127.99, 126.21, 101.57, 101.06, 83.39, 81.05, 78.70, 77.43, 77.11, 76.80, 75.41, 74.93, 74.52, 73.49, 72.90, 70.59, 67.86, 67.45, 65.97, 25.43, 24.08, 17.80, 14.85, −4.20, −4.97.

B. Synthesis of the Glycosphingolipid

Example B.1: Synthesis of (S)-3-(tert-Butoxycarbonyl)-N-methoxy-2,2, N-trimethyloxazolidine-4-carboxamide (13*)

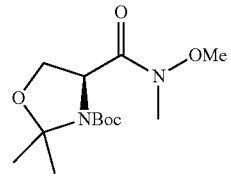 [SMILES: CON(C)C(=O)[C@@H]1COC(C)(C)N1C(=O)OC(C)(C)C]

To a solution of L-Boc-serine (12.33 g, 60.1 mmol) in DCM (240 mL) were added N,O-dimethylhydroxylamine hydrochloride (6.04 g, 61.9 mmol) and N-methylmorpholine (6.8 mL, 61.9 mmol) at 0° C. To this solution was added N-(3-dimethylaminopropyl)-N'-ethylcarbodiimide hydrochloride (11.86 g, 61.9 mmol) portionwise over a period of 20 min. and the solution was stirred for another 1 h. Then, aqueous HCl solution (1.0 M, 30 mL) was added and the aqueous layer was extracted with CH$_2$Cl$_2$ (2×100 mL). The combined organic layers were washed with saturated aqueous NaHCO$_3$ solution (30 mL) and the aqueous layer was again extracted with CH$_2$Cl$_2$ (100 mL). The combined organic layers were dried over MgSO$_4$ and the solvent was removed in vacuo to obtain the corresponding Weinreb amide (14.07 g, 94%) as white solid.

R$_f$=0.3 (EtOAc);
$^1$H NMR (250 MHz, CDCl$_3$) δ 5.60 (d, J=6.0 Hz, 1H), 4.77 (br s, 1H), 1.42 (s, 9H), 3.80 (d, J=3.3 Hz, 2H), 3.76 (s, 3H), 3.21 (s, 3H), 2.66 (br s, 1H).

The crude product was dissolved in acetone (180 mL) to which 2,2-dimethoxypropane (57 mL) and BF$_3$.Et$_2$O (0.5 mL) were added. The orange solution was stirred for 90 min. at r.t. and then quenched with Et$_3$N (1.2 mL) and solvents removed in vacuo. The crude product was purified by flash column chromatography on silica gel (gradient EtOAc/cyclohexane=1:2→1:1) to yield isopropylidene-protected Weinreb amide 13* (15.32 g, 89% over two steps) as a white solid. The NMR spectra consist of two sets of signals due to the presence of rotamers.

[α]$_D^{r.t.}$=−30.9 (c=1, CHCl$_3$); R$_f$=0.45 (Hexanes/EtOAc=1:1); IR (film) ν$_{max}$ 2976, 2938, 1702, 1682, 1364, 1167, 1098, 998, 848, 768, 716; $^1$H NMR (250 MHz, CDCl$_3$) δ 4.77 (dd, J=9.8, 2.8 Hz, 1H), 4.70 (dd, 7.5, 3.8, Hz, 1H), 4.18 (dd, J=7.5, 4.0 Hz, 1H), 4.15 (dd, J=7.8, 3.8 Hz, 1H), 3.95 (dd, J=9.3, 3.0 Hz, 1H), 3.91 (dd, J=9.0, 3.5 Hz), 3.72 (s, 3H), 3.68 (s, 3H), 3.19 (s, 6H), 1.68 (s, 3H), 1.66 (s, 3H), 1.54 (s, 3H), 1.50 (s, 3H), 1.47 (s, 9H), 1.39 (s, 9H); $^{13}$C NMR (101 MHz, CDCl$_3$) δ 171.4, 170.7, 152.2, 151.4, 95.1, 94.5, 80.6, 80.0, 66.2, 66.0, 61.3, 61.3, 57.9, 57.8, 28.5, 28.4, 25.8, 25.5, 24.8, 24.6; HR ESI Calcd for C$_{13}$H$_{24}$N$_2$O$_5$ [M+Na$^+$]: 311.1577 found: 311.1582.

Example B.2: Synthesis of tert-Butyl (S)-4-formyl-2,2-dimethyloxazolidine-3-carboxylate (14*)

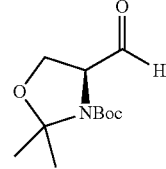 [SMILES: CC(C)(C)OC(=O)N1[C@H](C=O)COC1(C)C]

To a solution of Weinreb amide 13* (8.00 g, 27.7 mmol) in THF (100 mL) at 0° C. were added LiAlH$_4$ (1.0 M in THF, 13.9 mL, 13.9 mmol) dropwise and the solution was stirred for 1 h at 0° C. After 1 h, the solution was cooled to −10° C. and KHSO$_4$ (1M, 70 mL) was added carefully and the solution was diluted with Et$_2$O (170 mL). The mixture was allowed to warm to r.t. and stirred for 30 min. The organic layer was separated, dried over MgSO$_4$, filtered and the solvent was removed in vacuo to yield Garner's aldehyde 14* as a pale yellow oil (6.24 g, >95% purity by $^1$H NMR). The NMR spectra consist of two sets of signals due to the presence of rotamers. $^1$H NMR (250 MHz, CDCl$_3$) δ 9.58 (d, J=0.8 Hz, 1H), 9.52 (d, J=2.5 Hz, 1H), 4.32 (m, 1H), 4.16 (m, 1H), 4.06 (m, 4H), 1.53-1.63 (m, 12H), 1.49 (s, 9H), 1.40 (s, 9H). All spectral data in good accordance with reported data (*Synthesis* 1998, 1707). The crude product was used in the subsequent reaction without further purification.

Example B.3: Synthesis of (4R,1'Z)-3-(tert-Butoxycarbonyl)-2,2-dimethyl-4-(1'-hexadecenyl)oxazolidine (15*)

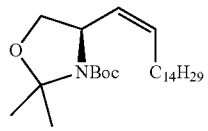

n-BuLi (1.6 M in hexane, 25.2 mL, 40.3 mmol) was added dropwise to pentadecyl-triphenylphosphonium bromide 16* (24.03 g, 43.4 mmol) in anhydrous THF (220 mL) at −78° C. The resulting orange solution was allowed to warm to 0° C. and stirred for another 30 min. The solution was then cooled to −78° C. and Garner's aldehyde 14* (6.23 g, 27.2 mmol) in anhydrous THF (30 mL) was added slowly. After being stirred for 2 h at r.t., the reaction was diluted with sat. aq. NH$_4$Cl solution (35 mL) and the layers were separated. The aqueous layer was extracted with CH$_2$Cl$_2$ (3×35 mL) and the combined organic extracts were washed with saturated aqueous NaCl solution (50 mL), dried over MgSO$_4$ and concentrated in vacuo. Purification by flash column chromatography on silica (EtOAc/Hexanes=1:2) gel gave (Z)-olefin 15* as a pale yellow oil (11.27 g, 78%).

[α]$_D^{r.t.}$=+45.2 (c=1, CHCl$_3$); R$_f$=0.40 (EtOAc/Hexanes=1:2); IR (film) v$_{max}$ 2923, 2854, 1699, 1457, 1382, 1251, 1175, 1093, 1056, 850, 768 cm$^{-1}$; $^1$H NMR (250 MHz, CDCl$_3$) δ 5.27-5.40 (m, 2H), 4.58 (br s, 1H), 4.02 (dd, J=6.3, 8.8 Hz, 1H), 3.61 (dd, J=3.3, 8.5 Hz, 1H), 1.96 (br s, 2H), 1.23-1.56 (m, 39H), 0.85 (t, J=7 Hz, 3H); $^{13}$C NMR (101 MHz, CDCl$_3$) δ 152.1, 130.9, 130.4, 94.1, 79.8, 69.2, 54.7, 32.1, 29.9, 29.8, 29.8, 29.8, 29.7, 29.6, 29.5, 29.4, 28.6, 28.6, 27.6, 22.8, 14.2; HR ESI Calcd for C$_{26}$H$_{49}$NO$_3$ [M+Na+]: 446.3605 found: 446.3614. All spectral data were in good accordance with reported data (*Synthesis* 2004, 847).

The desired (Z)-olefin can easily be distinguished from the undesired (E)-olefin by-product, when considering the olefinic protons in the $^1$H NMR spectrum: Z-15* $^1$H NMR (250 MHz, CDCl$_3$) δ 4.05 (dd, J=6.3, 8.6 Hz, I H), 3.64 (dd, J=3.3, 8.6 Hz, 1H) cf. E-15* $^1$H NMR (250 MHz, CDCl$_3$) δ4.01 (dd, J=6.1, 8.7 Hz, 1H), 3.71 (dd, J=2.1, 8.7 Hz, 1H).

Example B.4: Synthesis of pentadecyltriphenylphosphonium bromide (16*)

A solution of 1-bromopentadecane (30.0 g, 103 mmol) and triphenylphosphine (27.02 g, 103 mmol) in MeCN (200 mL) was refluxed at 80° C. for five days. After removal of the solvent in vacuo, Et$_2$O (30 mL) was added and the resulting white precipitate was filtered off, washed with Et$_2$O and dried on high vacuum for 24 h to give pentadecyltriphenylphosphonium bromide (16*) (49.66 g, 87%) as a white powder.

Example B.5: Synthesis of (2R,3Z)-2-(tert-Butoxycarbonyl)amino-3-octadecen-1-ol (17*)

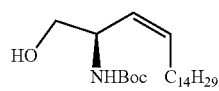

Para-Toluensulfonic acid (371 mg, 1.95 mmol) was added to a stirred solution of (Z)-olefin 15* (5.00 g, 12.2 mmol) in MeOH/water (50 mL total, ratio=9:1 v/v) and the mixture was stirred for 68 h. The reaction mixture was concentrated in vacuo to yield a white solid, which was re-dissolved in CH$_2$Cl$_2$ (100 mL). The solution was washed with brine (30 mL), dried over MgSO$_4$ and the solvent was removed in vacuo. Purification by flash column chromatography on silica gel (gradient cyclohexane/EtOAc=4:1→2:1) afforded alcohol 17* as a white solid (2.71 g, 59%). All spectral data were in good accordance with reported data (*Synthesis* 2004, 847).

Example B.6: Synthesis of (2S,3S,4R)-2-(tert-Butoxycarbonyl)amino-1,3,4-octadecanetriol (18*)

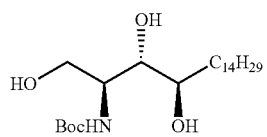

Alcohol 17* (1.50 g, 3.91 mmol) was dissolved in t-BuOH/water (38 mL total, ratio 1:1) and methanesulfonamide (371 mg, 3.91 mmol) was added. The reaction mixture was cooled to 0° C. and AD-mix-β (5.48 g) was added. The resulting mixture was stirred at 0° C. for 41 h and another 7 h at r.t., then it was quenched by the addition of solid Na$_2$SO$_3$ (6.0 g) and left to stir for 30 min. Extraction with EtOAc (3×40 mL) followed. The organic extracts were washed with NaOH (1 M, 20 mL), water (20 mL) and saturated aqueous NaCl solution (20 mL), dried over MgSO$_4$ and solvents were removed in vacuo. Purification by flash column chromatography on silica gel (gradient EtOAc/cyclohexane=1:1→2:1) provided triol 18* as a white solid (1.05 g, 64%). All spectral data were in good accordance with reported data (*Synthesis* 2004, 847).

Example B.7: Synthesis of (2S,3S,4R)-2-aminooctadecane-1,3,4-triol (19*)

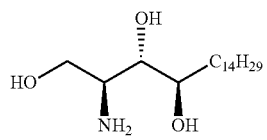

Triol 18* (60 mg, 0.14 mmol) was dissolved in TFA/H$_2$O (20:1, 0.6 mL) and stirred at r.t. for 30 min. The solution was diluted with CH$_2$Cl$_2$ (1.5 mL) and then carefully neutralized (to pH ~8) with saturated aqueous NaHCO$_3$ solution (10 mL) upon which precipitation of a white solid occurred. The white solid removed by filtration, washed with water (3×10 mL) and dried under reduced pressure. Recrystallization from MeCN yielded phytosphingosine 19* as a white powder (38 mg, 82%). All spectral data were in good accordance with reported data (*Synthesis* 2004, 847).

Example B.8: Synthesis of hexacosanoic N-hydroxysuccinimidyl ester (20*)

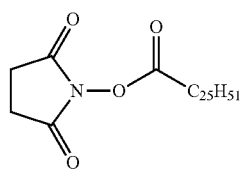

To a solution of hexacosanoic acid (121 mg, 0.304 mmol) in CH$_2$Cl$_2$ (4 mL) were added 1-ethyl-3-(3-dimethylaminopropyl)carbodiimide (0.058 mL, 0.33 mmol) and N-hydroxysuccinimide (42 mg, 0.37 mmol). The reaction mixture was heated to 40° C., stirred for 3 h and then quenched with water (4 mL). The solution was diluted with Et$_2$O (8 mL) and the two layers were separated. The aqueous phase was extracted with Et$_2$O (8 mL) and the combined organic layers were washed with saturated aqueous NaCl solution (5 mL), dried over MgSO$_4$ and filtered. After removal of the solvent in vacuo, N-hydroxysuccinimidyl ester 20* was obtained as a white solid (85 mg, 57%).

Example B.9: Synthesis of N-((2S,3S,4R)-1,3,4-trihydroxyoctadecan-2-yl)heptacosanamide (21*)

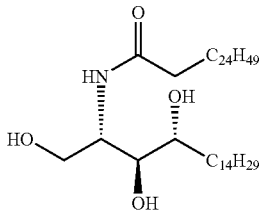

To a solution of phytosphingosine 19* (15 mg, 0.047 mmol) in anhydrous THF (1 mL) was added succinimidyl ester 20* (34 mg, 0.071 mmol) and Et$_3$N (24 μL, 0.14 mmol). The solution was heated to 50° C. and stirred for 20 h. EtOAc (5 mL) was added and the resulting suspension was centrifuged (30 min., 3000 rpm). The white precipitate was removed by filtration and dried under reduced pressure to yield amide 21* (29 mg, 88%).

Example B.10: Synthesis of (2S,3S,4R)-1,3,4-Tri-t-butyl-dimethylsilyloxy-2-hexacosanoylamino-1-octadecane (22*)

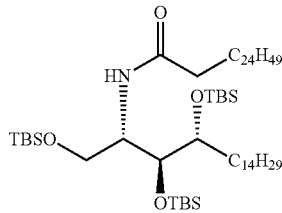

To a stirred suspension of amide 21* (25 mg, 0.036 mmol) in CH$_2$Cl$_2$ (1.2 mL) was added TBSOTf (43 μL, 0.18 mmol) and 2,6-lutidine (65 μL, 0.054 mmol) at 0° C. The reaction mixture was stirred at r.t. for 2 h. The reaction was quenched with MeOH (0.2 mL). The mixture was diluted with Et$_2$O (2 mL) and washed with saturated aqueous NaHCO$_3$ solution (1 mL) and saturated aqueous NaCl solution (1 mL). The organic layer was dried over MgSO$_4$, filtered and concentrated under reduced pressure. The residue was purified by flash column chromatography on silica gel (cyclohexane/Et$_2$O=15:1) to give TBS protected ceramide 22* as a colorless oil (27 mg, 71%). All spectral data were in good accordance with reported data (*Synthesis* 2004, 847).

Example B.11: Synthesis of (2S,3S,4R)-3,4-Bis-tert-butyldimethylsilyloxy-2-hexacosanoylamino-4-octadecanol (23*)

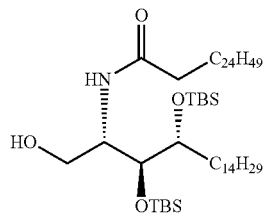

To a solution of ceramide 22* (90 mg, 0.087 mmol) in THF (2 mL) was added TFA (40 μL, 0.519 mmol) in water (0.5 mL, 27.8 mmol) at −10° C. The reaction mixture was left to warm to 10° C. over a period of 2 h. Then, the reaction mixture was quenched by the addition of saturated aqueous NaHCO$_3$ solution until neutral pH was reached. The resulting mixture was diluted with Et$_2$O (10 mL), washed with water (10 mL), saturated aqueous NaHCO$_3$ (10 mL), saturated aqueous NaCl solution (10 mL), and dried over MgSO$_4$. The solvent was removed in vacuo and the crude product was purified by flash column chromatography on silica gel (gradient EtOAc/cyclohexane=10:1→5:1) to yield alcohol 23* (68 mg, 85%) as a colorless oil.

$[α]_D^{r.t.}$=−11.6 (c=1, CHCl$_3$); R$_f$=0.3 (cyclohexane/EtOAc=4:1); IR (film) $ν_{max}$ 3285, 2920, 2851, 1645, 1465, 1253, 1034, 835, 776, 721, 680 cm$^{-1}$; $^1$H NMR (400 MHz, CDCl$_3$) δ 6.27 (d, J=7.8 Hz, 1H), 4.21 (dd, J=11.3, 3.0 Hz, 1H), 4.06 (td, J=6.5, 3.2 Hz, 1H), 3.91 (t, J=2.8 Hz, 1H), 3.76 (td, J=6.4, 2.6 Hz, 1H), 3.59 (dd, J=11.3, 3.7 Hz, 1H), 3.15 (dd, J=9.0, 3.3 Hz, 1H), 2.20-2.16 (m, 2H), 1.67-1.47 (m, 6H), 1.45-1.16 (m, 68H), 0.92 (s, 9H), 0.90 (s, 9H), 0.87 (t, J=6.9 Hz, 6H), 0.11 (s, 6H), 0.08 (s, 6H); $^{13}$C NMR (126 MHz, CDCl$_3$) δ 172.62, 77.42, 76.36, 63.62, 51.3, 36.93, 34.42, 31.92, 29.80, 29.70, 29.63, 29.53, 29.48, 29.37, 26.00, 25.94, 25.81, 25.60, 22.69, 18.14, 18.12, 14.13, −3.76, −4.08, −4.53, −4.91; HR ESI Calcd for C$_{56}$H$_{117}$NO$_4$Si$_2$ [M+Na$^+$]: 924.8594 found: 924.8604.

Alcohols 23*a-23*o were synthesized according to the procedure described at example 15-23 starting from common aldehyde 14*:

| Comp. | Structure | HRMS |
|---|---|---|
| 23*a | ![structure] | C$_{35}$H$_{75}$NO$_4$Si$_2$<br>Calc.: 631.1544 [M + H$^+$]<br>Found: 631.1521 |

-continued

| Comp. | Structure | HRMS |
|---|---|---|
| 23*b | 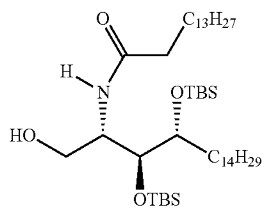 | $C_{45}H_{95}NO_4Si_2$<br>Calc.: 771.4206 [M + H$^+$]<br>Found: 771.4181 |
| 23*c | 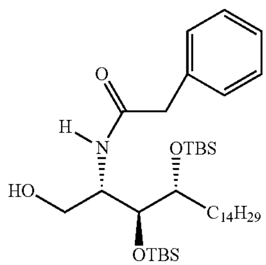 | $C_{38}H_{73}NO_4Si_2$<br>Calc.: 665.1707 [M + H$^+$]<br>Found: 665.1733 |
| 23*d | 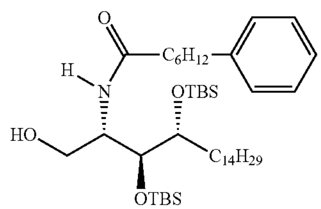 | $C_{43}H_{83}NO_4Si_2$<br>Calc.: 735.3038 [M + H$^+$]<br>Found: 735.3001 |
| 23*e | 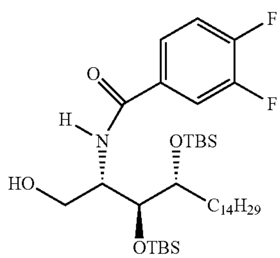 | $C_{37}H_{69}F_2NO_4Si_2$<br>Calc.: 687.1250 [M + H$^+$]<br>Found: 687.1212 |
| 23*f | 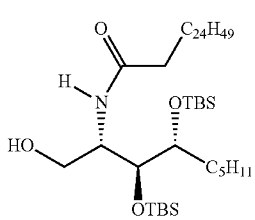 | $C_{47}H_{99}NO_4Si_2$<br>Calc.: 799.4738 [M + H$^+$]<br>Found: 799.4791 |
| 23*g | 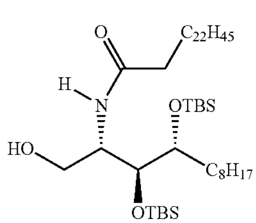 | $C_{48}H_{101}NO_4Si_2$<br>Calc.: 813.5004 [M + H$^+$]<br>Found: 813.4962 |

| Comp. | Structure | HRMS |
|---|---|---|
| 23*h | 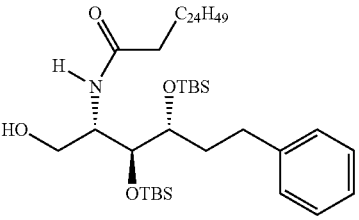 | $C_{50}H_{97}NO_4Si_2$<br>Calc.: 833.4901 [M + H$^+$]<br>Found: 833.4913 |
| 23*i | 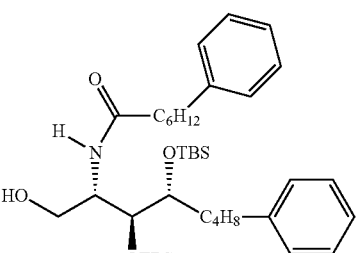 | $C_{39}H_{67}NO_4Si_2$<br>Calc.: 671.1338 [M + H$^+$]<br>Found: 671.1306 |
| 23*j | 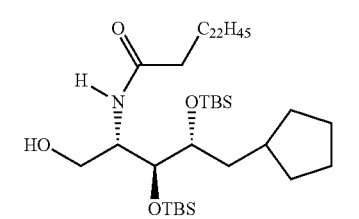 | $C_{46}H_{95}NO_4Si_2$<br>Calc.: 783.4313 [M + H$^+$]<br>Found: 783.4281 |
| 23*k | 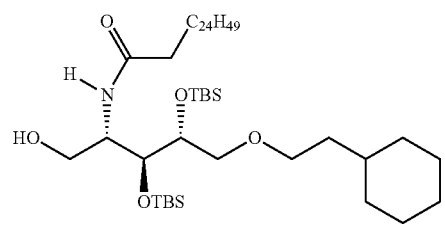 | $C_{51}H_{105}NO_5Si_2$<br>Calc.: 869.5638 [M + H$^+$]<br>Found: 869.5604 |
| 23*l | 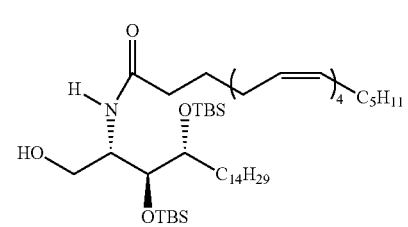 | $C_{50}H_{97}NO_4Si_2$<br>Calc.: 833.4901 [M + H$^+$]<br>Found: 833.4887 |
| 23*m | 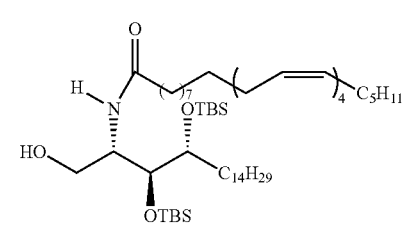 | $C_{56}H_{109}NO_4Si_2$<br>Calc.: 917.6498 [M + H$^+$]<br>Found: 917.6528 |
| 23*n | 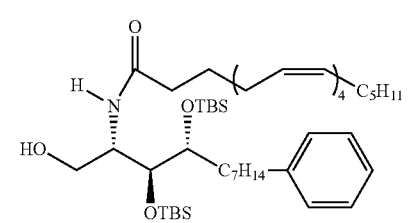 | $C_{49}H_{87}NO_4Si_2$<br>Calc.: 811.4000 [M + H$^+$]<br>Found: 811.4063 |

| Comp. | Structure | HRMS |
|---|---|---|
| 23*o | 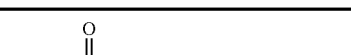 | $C_{57}H_{103}NO_4Si_2$<br>Calc.: 923.6129 [M + H$^+$]<br>Found: 923.6097 |

Example B.12: Synthesis of 6-hydroxyhexyl 4-methylbenzenesulfonate (24*)

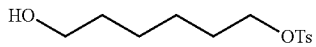

To a solution of hexane-1,6-diol (10.0 g, 85 mmol) in DCM (200 mL) was added 4-methylbenzene-1-sulfonyl chloride (17.8 g, 93 mmol) dissolved in pyridine (100 mL) at 5° C. dropwise over 15 min. The reaction mixture was warmed to r.t. over the period of 5 h. Solvents were removed in vacuo and the crude was purified by silica flash column chromatography (gradient hexanes/EtOAc=1:0→1:1) to afford monotosylated hexanediol 24* (6.5 g, 28%) as a colorless oil.

$R_f$=0.55 (Hexanes/EtOAc=1:1); IR (film) $v_{max}$ 3381, 2935, 2862, 1598, 1461, 1352, 1172, 959, 921, 813, 661 cm$^{-1}$; $^1$H NMR (400 MHz, CDCl$_3$) δ 7.76-7.71 (m, 2H), 7.29 (dt, J=4.3, 1.2 Hz, 2H), 3.97 (t, J=6.5 Hz, 2H), 3.55 (t, J=6.5 Hz, 2H), 2.40 (s, 3H), 1.65-1.56 (m, 2H), 1.55 (s, 1H), 1.52-1.41 (m, 2H), 1.36-1.18 (m, 4H); $^{13}$C NMR (101 MHz, CDCl$_3$) δ 144.7, 133.1, 129.8, 127.8, 70.5, 62.6, 32.4, 28.7, 25.1, 25.0, 21.6; HR ESI Calcd for $C_{13}H_{20}O_4S$ [M+Na$^+$]: 295.0975 found: 295.0968.

Example B.13: Synthesis of 6-azidohexan-1-ol (25*)

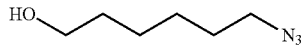

6-Hydroxyhexyl 4-methylbenzenesulfonate 24* (4.3 g, 15.79 mmol) was dissolved in DMF (23 mL) and sodium azide (1.75 g, 26.8 mmol) was added. The mixture was heated to 55° C. and after 16 h it was cooled to r.t. and diluted with water (150 mL). The mixture was extracted three times with CH$_2$Cl$_2$ and washed with saturated aqueous NaCl solution. The organic layer was dried over MgSO$_4$ and solvents were removed in vacuo. The crude product was purified by silica flash column chromatography on silica gel (gradient hexanes/EtOAc=1:0→1:1) to afford 6-azidohexan-1-ol 25* (2.2 g, 97%) as a colorless oil.

$R_f$=0.50 (Hexanes/EtOAc=2:1); IR (film) $v_{max}$ 3329, 2935, 2891, 2090, 1256, 1349, 1258, 1055, 910, 731 cm$^{-1}$; $^1$H NMR (400 MHz, CDCl$_3$) δ 3.63 (t, J=6.5 Hz, 2H), 3.25 (t, J=6.9 Hz, 2H), 1.64-1.51 (m, 4H), 1.43-1.32 (m, 4H); $^{13}$C NMR (101 MHz, CDCl$_3$) δ 62.8, 51.5, 32.6, 28.9, 26.6, 25.4; HR ESI Calcd for $C_6H_{13}N_3O$ [M+Na$^+$]: 166.0951 found: 166.0945.

Example B.14: Synthesis of 6-azidohexyl 4-methylbenzenesulfonate (26*)

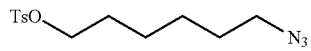

To a solution of 6-azidohexan-1-ol 25* (2.7 g, 18.9 mmol) in pyridine (70 mL) was added 4-methylbenzene-1-sulfonyl chloride (4.0 g, 21.0 mmol). The reaction mixture was left to stir for 5 h at r.t. after which the solvent was removed in vacuo and the crude product was dissolved in CH$_2$Cl$_2$, washed with water and dried over MgSO$_4$. Solvents were removed in vacuo and the crude product was purified by silica flash column chromatography on silica gel (gradient hexanes/EtOAc=1:0→1:1) to afford azide 26* (5.0 g, 89%) as a colourless oil.

$R_f$=0.50 (Hexanes/EtOAc=3:1); IR (film) $v_{max}$ 2938, 2863, 2092, 1598, 1455, 1356, 1258, 1174, 1097, 956, 919, 813, 724, 662 cm$^{-1}$; $^1$H NMR (400 MHz, CDCl$_3$) δ; 7.85-7.67 (m, 2H), 7.33 (dd, J=8.5, 0.6 Hz, 2H), 4.01 (t, J=6.4 Hz, 2H), 3.21 (t, J=6.9 Hz, 2H), 2.43 (s, 3H), 1.71-1.57 (m, 2H), 1.52 (dd, J=9.1, 4.9 Hz, 2H), 1.38-1.12 (m, 4H); $^{13}$C NMR (101 MHz, CDCl$_3$) δ 144.8, 133.2, 129.9, 127.9, 70.4, 51.3, 28.7, 28.7, 26.1, 25.0, 21.7; HR ESI Calcd for $C_{13}H_{19}N_3O_3S$ [M+Na$^+$]: 320.1045 found: 320.1057.

Azides 26*a-26*f were synthesized following the procedure described in examples 24-26 starting from the corresponding commercially available diols.

| comp. | structure | HRMS |
|---|---|---|
| 26*a | TsO~(~~O~)$_3$~N$_3$ | $C_{15}H_{23}N_3SO_6$<br>Calc.: 374.4344 [M + H$^+$]<br>Found: 374.4388 |
| 26*b | TsO-CH$_2$CH$_2$-C$_6$H$_4$-CH$_2$CH$_2$-N$_3$ | $C_{17}H_{19}N_3SO_3$<br>Calc.: 346.4259 [M + H$^+$]<br>Found: 346.4212 |

-continued

| comp. | structure | HRMS |
|---|---|---|
| 26*c | TsO~~~N₃ (with methyl branch) | C₁₁H₁₅N₃SO₃<br>Calc.: 270.3297 [M + H⁺]<br>Found: 270.3229 |
| 26*d | TsO-(CH₂)₆-N₃ | C₁₉H₃₁N₃SO₃<br>Calc.: 382.5426 [M + H⁺]<br>Found: 382.5461 |
| 26*e | TsO~S~~S~N₃ (with methyl branch) | C₁₅H₂₃N₃S₃O₃<br>Calc.: 390.5683 [M + H⁺]<br>Found: 390.5662 |
| 26*f | TsO~S~S~N₃ | C₉H₁₁N₃S₃O₃<br>Calc.: 306.4086 [M + H⁺]<br>Found: 306.4041 |

Example B.15: Synthesis of allyl 6-O-trityl-α-D-galactopyranoside (27*)

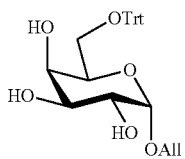

1-O-Allyl-galactoside (*Org. Lett.* 2002, 4, 489) (4 g, 18.2 mmol) was dissolved in pyridine (18 mL). To the solution was added trityl chloride (6.58 g, 23.6 mmol) and the mixture was stirred at r.t. for 18 h after which the solvent was removed in vacuo. The crude product was purified by flash column chromatography on silica gel (CH₂Cl₂/MeOH=10:1) to yield pyranoside 27* (7.0 g, 83%) as colorless oil.

[α]$_D^{r.t.}$=+60.0 (c=1, CHCl₃); R$_f$=0.8 (CH₂Cl₂/MeOH=5:1); IR (film) ν$_{max}$ 3402, 2929, 1491, 1449, 1218, 1152, 1070, 1032, 746, 703 cm⁻¹; ¹H NMR (400 MHz, CDCl₃) δ 7.51-7.18 (m, 15H), 5.99-5.88 (m, 1H), 5.25 (ddq, J=35.9, 10.4, 1.4 Hz, 2H), 4.95 (d, J=3.8 Hz, 1H), 4.25 (ddt, J=12.8, 5.4, 1.4 Hz, 1H), 4.05 (ddt, J=12.8, 6.3, 1.3 Hz, 1H), 3.96 (s, 1H), 3.89 (t, J=5.8 Hz, 1H), 3.81 (d, J=5.7 Hz, 1H), 3.75 (d, J=9.8 Hz, 1H), 3.47 (s, 1H), 3.43 (dd, J=9.8, 6.1 Hz, 1H), 3.32 (dd, J=9.8, 5.3 Hz, 1H), 2.86 (d, J=2.1 Hz, 1H), 2.71 (d, J=8.1 Hz, 1H); ¹³C NMR (75 MHz, CDCl₃) δ 143.8, 133.7, 128.6, 127.8, 127.1, 117.8, 97.5, 86.9, 71.2, 69.8, 69.5, 69.5, 68.5, 63.3; HR ESI Calcd for C₂₅H₂₅O₅ [M+Na⁺]: 485.1935 found: 485.1941.

Example B.16: Synthesis of allyl 2,3,4-tri-O-benzyl-6-O-trityl-α-D-galactopyranoside (28*)

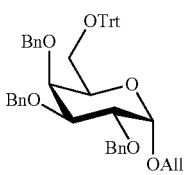

To a solution of allyl 6-O-trityl-α/β-D-galactopyranoside 27* (3.7 g, 8.0 mmol) in DMF (32 mL) was added sodium hydride (60% in mineral oil, 1.50 g, 36.0 mmol) portionwise at r.t. After 1 h benzyl bromide (4.2 mL, 35.2 mmol) was added. The reaction mixture was left to stir for 48 h after which it was quenched by the addition of MeOH (5 mL). The mixture was diluted with Et₂O and extracted twice from saturated aqueous NaHCO₃. The combined organic layer was washed with water (3×100 mL) and saturated aqueous NaCl solution and dried over MgSO₄. The solvent was removed in vacuo and the crude product was over a plug of silica gel (hexanes/EtOAc=2:1, silica gel was neutralized with 1% NEt₃) to yield the benzyl ether 28* (5.5 g) as a pale yellow oil which was used in the subsequent step without further purification.

Example B.17: Synthesis of allyl 6-(6'-azidohexyl)-2,3,4-tri-O-benzyl-α-D-galactopyranoside (29*)

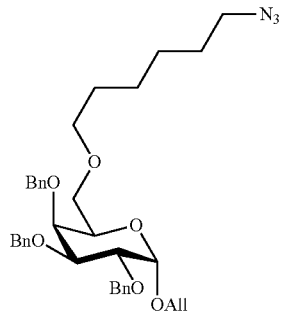

A solution of allyl 2,3,4-tri-O-benzyl-6-O-trityl-α-D-galactopyranoside 28* (5.00 g, 6.82 mmol) and triethyl silane (5.45 mL, 34.1 mmol) in CH₂Cl₂ (68 mL) was cooled to 0° C. To the stirred solution was added trifluoroacetic acid (2.6 mL, 34.1 mmol) dropwise. The mixture was quenched after 15 min. with saturated aqueous NaHCO₃ solution and extracted with CH₂Cl₂. The crude product was filtered over a plug of silica gel. All silane and trityl residues were removed with 10:1 hexanes/EtOAc and the product was eluted with EtOAc to yield allyl 2,3,4-tri-O-benzyl-α-D-galactopyranoside (3.0 g) as a pale yellow oil, which was used without further purification in the subsequent reaction.

To a solution of allyl 2,3,4-tri-O-benzyl-α-D-galactopyranoside (1.0 g, 2.04 mmol) in DMF (10 mL) was added sodium hydride (60% in mineral oil, 0.12 g, 3.1 mmol) at 0° C. After 15 min, the mixture was warmed to r.t. and stirred for another 1 h. Then, 6-azidohexyl 4-methylbenzenesulfonate 26* (0.9 g, 3.1 mmol) was added and the reaction mixture was stirred at r.t. for a further 8 h after which the mixture was quenched by the addition of MeOH (2 mL). After dilution with DCM, saturated aqueous NH$_4$Cl solution was added and the mixture was extracted with DCM. The combined organic layer was washed with water and saturated aqueous NaCl solution. The organic layer was dried over MgSO$_4$, the solvent was removed in vacuo and the crude product was purified by flash column chromatography on silica gel (gradient hexanes/EtOAc=1:0→1:1) to yield azide 29* (1.0 g, 68% over three steps) as a colorless oil. [α]$_D$$^{r.t.}$=+25.4 (c=1, CHCl$_3$); R$_f$=0.65 (Hexanes/EtOAc=4:1); IR (film) ν$_{max}$ 2933, 2863, 2094, 1497, 1454, 1358, 1177, 1098, 1059, 926, 816, 736, 697 cm$^{-1}$; $^1$H NMR (400 MHz, CDCl$_3$) δ 7.94-7.16 (m, 15H), 5.95 (dddd, J=17.1, 10.3, 6.6, 5.2 Hz, 1H), 5.31 (dq, J=17.2, 1.6 Hz, 1H), 5.21 (ddd, J=10.3, 2.8, 1.1 Hz, 1H), 5.01-4.58 (m, 7H), 4.17 (ddt, J=13.0, 5.2, 1.4 Hz, 1H), 4.09-3.99 (m, 3H), 3.98-3.90 (m, 2H), 3.50-3.18 (m, 6H), 1.72-1.47 (m, 4H), 1.44-1.30 (m, 4H); $^{13}$C NMR (75 MHz, CDCl$_3$) δ 138.9, 138.8, 138.6, 134.0, 129.8, 128.3, 128.3, 128.2, 128.1, 128.0, 127.9, 127.6, 127.5, 127.4, 117.9, 96.3, 79.1, 76.5, 75.3, 74.7, 73.3, 73.3, 71.3, 70.3, 69.5, 69.4, 68.2, 51.4, 51.2, 29.6, 28.8, 28.7, 28.6, 26.6, 26.1, 25.7, 25.0, 21.6. HR ESI Calcd for C$_{36}$H$_{45}$N$_3$O$_6$ [M+Na$^+$]: 638.3201 found: 638.3229.

Azides 29*a-29*f were obtained starting from allyl 2,3,4-tri-O-benzyl-α-D-galactopyranoside and intermediates 26*a-26*f.

| comp. | structure | HRMS |
|---|---|---|
| 29*a | 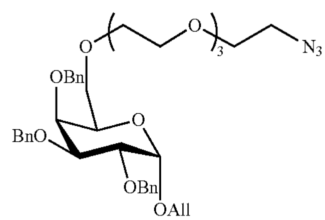 | C$_{38}$H$_{50}$N$_3$O$_9$<br>Calc.: 693.8278 [M + H$^+$]<br>Found: 693.8241 |
| 29*b | 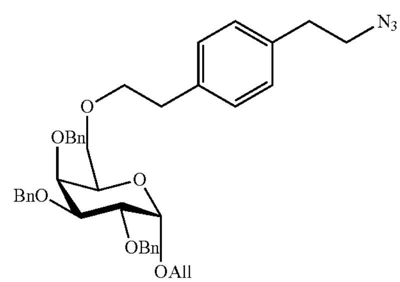 | C$_{36}$H$_{46}$N$_3$O$_6$<br>Calc.: 617.7764 [M + H$^+$]<br>Found: 617.7721 |
| 29*c | 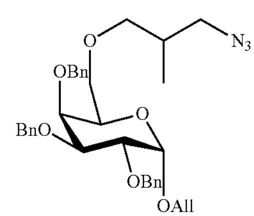 | C$_{34}$H$_{42}$N$_3$O$_6$<br>Calc.: 589.7231 [M + H$^+$]<br>Found: 589.7274 |
| 29*d | 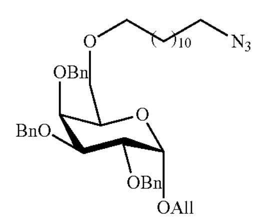 | C$_{42}$H$_{58}$N$_3$O$_6$<br>Calc.: 701.9361 [M + H$^+$]<br>Found: 701.9400 |
| 29*e | 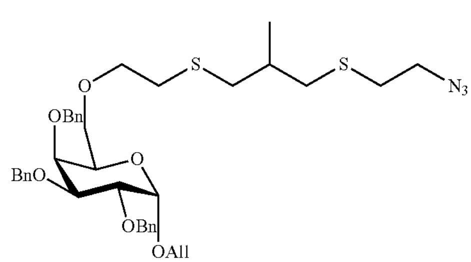 | C$_{38}$H$_{50}$N$_3$S$_2$O$_6$<br>Calc.: 709.9618 [M + H$^+$]<br>Found: 709.9651 |

| comp. | structure | HRMS |
|---|---|---|
| 29*f | 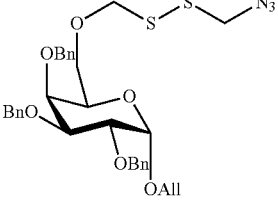 | $C_{32}H_{38}N_3S_2O_6$<br>Calc.: 625.8021 [M + H$^+$]<br>Found: 625.7996 |

In a similar manner, the analogues in glucose series 29a-29f were obtained starting from allyl 2,3,4-tri-O-benzyl-α-D-glucopyranoside and intermediates 26*a-26*f.

| comp. | structure | mass spec |
|---|---|---|
| 29**a | 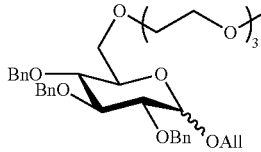 | $C_{38}H_{50}N_3O_9$<br>Calc.: 693.8278 [M + H$^+$]<br>Found: 693.8241 |
| 29**b | 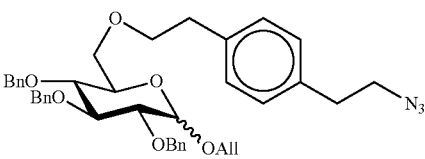 | $C_{36}H_{46}N_3O_6$<br>Calc.: 617.7764 [M + H$^+$]<br>Found: 617.7721 |
| 29**c | 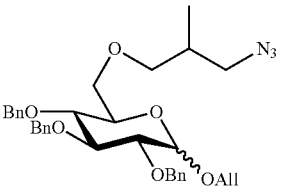 | $C_{34}H_{42}N_3O_6$<br>Calc.: 589.7231 [M + H$^+$]<br>Found: 589.7274 |
| 29**d | 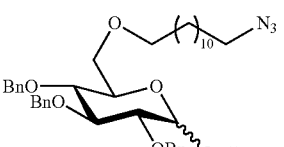 | $C_{42}H_{58}N_3O_6$<br>Calc.: 701.9361 [M + H$^+$]<br>Found: 701.9400 |
| 29**e | 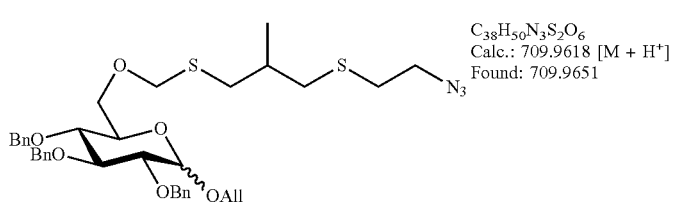 | $C_{38}H_{50}N_3S_2O_6$<br>Calc.: 709.9618 [M + H$^+$]<br>Found: 709.9651 |
| 29**f | 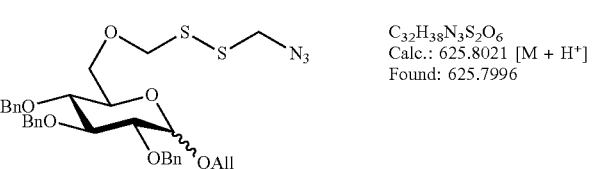 | $C_{32}H_{38}N_3S_2O_6$<br>Calc.: 625.8021 [M + H$^+$]<br>Found: 625.7996 |

Example B.18: Synthesis of 6-(6'-azidohexyl)-2,3,4-tri-O-benzyl-α/β-D-galactopyranose (30*)

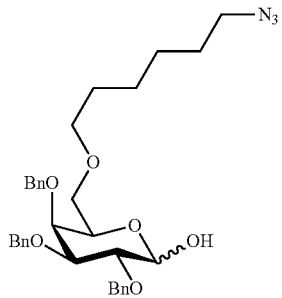

Allyl 6-(6'-azidohexyl)-2,3,4-tri-O-benzyl-α-D-galactopyranoside 29* (1.4 g, 2.3 mmol) was dissolved in MeOH (16 mL) and PdCl$_2$ (0.21 g, 1.17 mmol) was added to the solution at r.t. The mixture was stirred at for 4 h after which the mixture was filtered over celite and the solvent was removed in vacuo. The crude product was purified by flash column chromatography (gradient hexanes/EtOAc=1:0→1:1) to yield lactol 30* (1.2 g, 88%) as a colorless oil.

$R_f$=0.50 (Hexanes/EtOAc=2:1); IR (film) $v_{max}$ 3414, 2933, 2862, 2093, 1454, 1255, 1060, 910, 733, 696 cm$^{-1}$; $^1$H NMR (400 MHz, CDCl$_3$) δ 7.45-7.20 (m, 30H), 5.33-5.27 (m, 1H), 5.01-4.90 (m, 3H), 4.85-4.71 (m, 7H), 4.66 (ddd, J=16.7, 11.5, 6.0 Hz, 3H), 4.18-4.09 (m, 1H), 4.05 (dd, J=9.2, 3.6 Hz, 1H), 3.96 (s, 2H), 3.93 (d, J=2.8 Hz, 1H), 3.88 (d, J=2.8 Hz, 1H), 3.78 (dd, J=9.6, 7.5 Hz, 1H), 3.63-3.52 (m, 3H), 3.52-3.37 (m, 5H), 3.37-3.28 (m, 2H), 3.28-3.21 (m, 5H), 1.65-1.49 (m, 8H), 1.42-1.24 (m, 8H); $^{13}$C NMR (101 MHz, CDCl$_3$) δ 138.8, 138.7, 138.5, 138.4, 128.5, 128.5, 128.4, 128.3, 128.3, 128.3, 128.3, 128.1, 127.9, 127.7, 127.7, 127.7, 127.6, 97.9, 92.0, 82.3, 80.9, 78.8, 76.7, 75.2, 74.9, 74.8, 74.7, 73.8, 73.7, 73.6, 73.1, 73.1, 71.5, 71.4, 69.6, 69.6, 69.5, 51.5, 29.5, 28.9, 26.6, 25.8; HR ESI Calcd for C$_{33}$H$_{41}$N$_3$O$_6$ [M+Na$^+$]: 598.2883 found: 598.2869.

Example B.19: Synthesis of 6-(6'-Azidohexyl)-2,3,4-tri-O-benzyl-β-D-galactopyranosyl N-phenyl trifluoroacetimidate (31*)

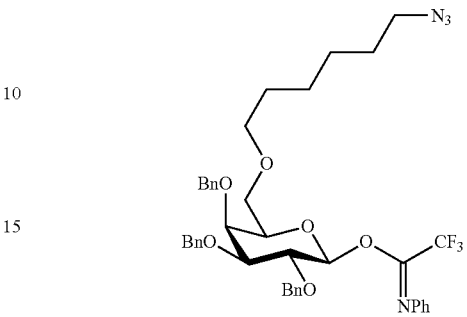

To a solution of 6-(6'-azidohexyl)-2,3,4-tri-O-benzyl-α/β-D-galactopyranose 30* (400 mg, 0.70 mmol) in DCM (7 mL) was added cesium carbonate (340 mg, 1.04 mmol). To the mixture was added 2,2,2-trifluoro-N-phenylacetimidoyl chloride (216 mg, 1.04 mmol) and the reaction mixture was stirred at r.t. for 3.5 h after which it was filtered over celite and washed with DCM. The solvent was removed in vacuo and the crude product was purified by flash column chromatography on silica gel (gradient hexanes/EtOAc=10:1→1:1) to yield the imidate 31* (490 mg, 94%) as a colorless oil.

[α]$_D^{r.t.}$=+60.8 (c=0.4, CHCl$_3$); $R_f$=0.80 (Hexanes/EtOAc=2:1); IR (film) $v_{max}$ 3064, 2934, 2865, 2094, 1717, 1598, 1454, 1321, 1207, 1099, 1027, 910, 734, 696 cm$^{-1}$, $^1$H NMR (400 MHz, CDCl$_3$) δ 7.45-6.60 (m, 20H), 5.56 (s, 1H), 4.90 (d, J=11.5 Hz, 1H), 4.75 (s, J=1.5 Hz, 2H), 4.68 (s, J=12.4 Hz, 2H), 4.58 (d, J=11.6 Hz, 1H), 4.00 (t, J=8.7 Hz, 1H), 3.84 (d, J=2.4 Hz, 1H), 3.58-3.39 (m, 4H), 3.34 (dt, J=9.3, 6.5 Hz, 1H), 3.23 (dt, J=9.3, 6.5 Hz, 1H), 3.14 (t, J=6.9 Hz, 2H), 1.52-1.38 (m, 4H), 1.32-1.16 (m, 4H); $^{13}$C NMR (101 MHz, CDCl$_3$) δ 138.6, 138.3, 138.2, 128.8, 128.6, 128.5, 128.4, 128.4, 128.3, 128.0, 127.9, 127.8, 127.7, 124.3, 119.4, 82.3, 78.3, 77.4, 77.2, 76.8, 75.7, 74.9, 74.6, 73.4, 73.2, 71.4, 68.7, 51.5, 29.7, 28.9, 26.7, 25.8; HR ESI Calcd for C$_{41}$H$_{45}$F$_3$N$_4$O$_6$ [M+Na$^+$]: 769.3183 found: 769.3239.

Starting from hemiacetals 29*a-29*f, imidate donors 31*a-31*f were synthesized according to the procedures described in examples 30 and 31.

| comp. | structure | HRMS |
|---|---|---|
| 31*a | ![structure] | C$_{43}$H$_{50}$F$_3$N$_4$O$_9$<br>Calc.: 824.8834 [M + H$^+$]<br>Found: 824.8804 |

-continued
| comp. | structure | HRMS |
|---|---|---|
| 31*b | 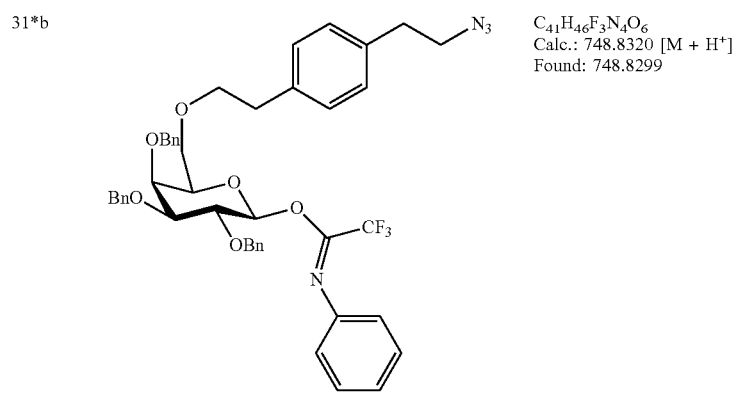 | $C_{41}H_{46}F_3N_4O_6$<br>Calc.: 748.8320 [M + H⁺]<br>Found: 748.8299 |
| 31*c | 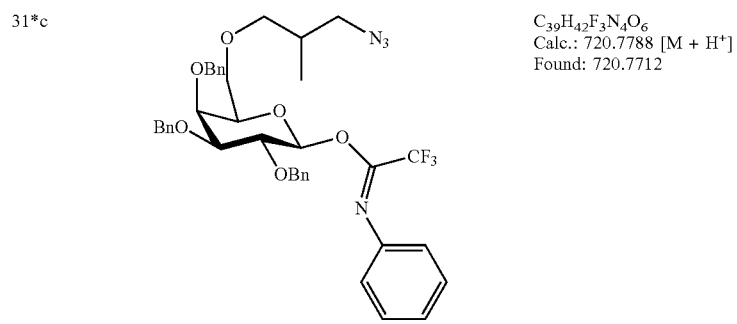 | $C_{39}H_{42}F_3N_4O_6$<br>Calc.: 720.7788 [M + H⁺]<br>Found: 720.7712 |
| 31*d | 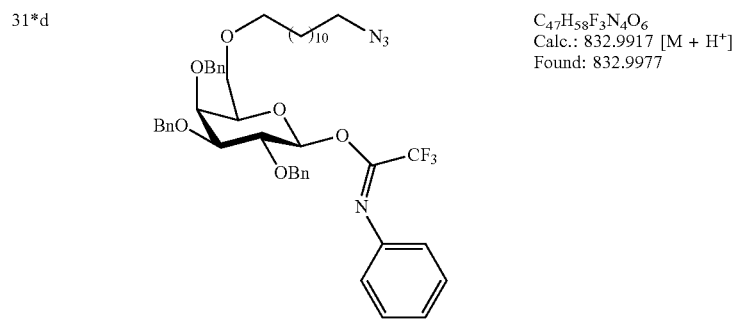 | $C_{47}H_{58}F_3N_4O_6$<br>Calc.: 832.9917 [M + H⁺]<br>Found: 832.9977 |
| 31*e | 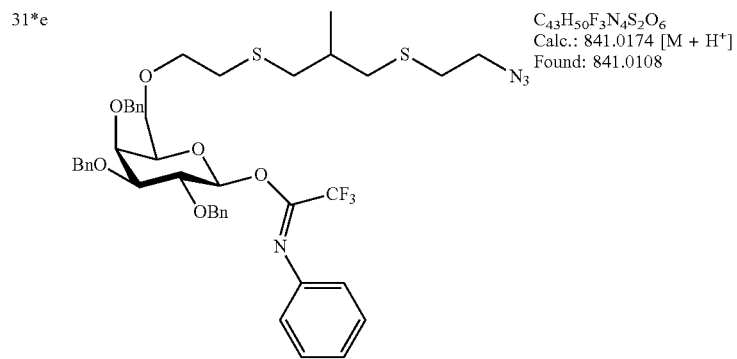 | $C_{43}H_{50}F_3N_4S_2O_6$<br>Calc.: 841.0174 [M + H⁺]<br>Found: 841.0108 |

| comp. | structure | HRMS |
|---|---|---|
| 31*f | 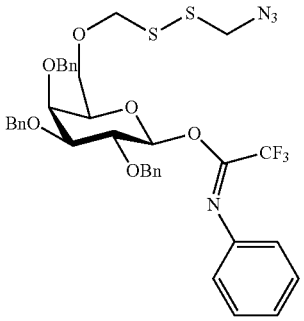 | $C_{37}H_{38}F_3N_4S_2O_6$<br>Calc.: 756.8577 [M + H⁺]<br>Found: 756.8506 |
In a similar manner, imidate donors in glucose series 31a-31f were accessed starting from the corresponding hemiacetals 29a-29f.
| comp. | structure | HRMS |
|---|---|---|
| 31**a | 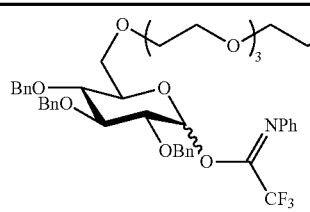 | $C_{43}H_{50}F_3N_4O_9$<br>Calc.: 824.8834 [M + H⁺]<br>Found: 824.8804 |
| 31**b | 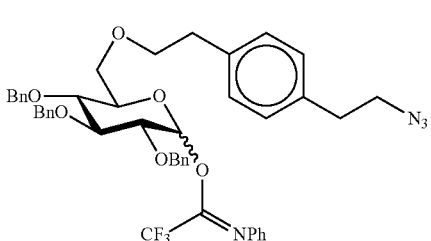 | $C_{41}H_{46}F_3N_4O_6$<br>Calc.: 748.8320 [M + H⁺]<br>Found: 748.8299 |
| 31**c | 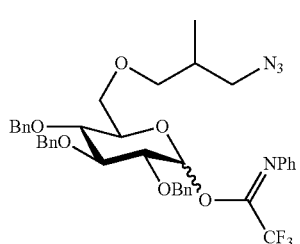 | $C_{39}H_{42}F_3N_4O_6$<br>Calc.: 720.7788 [M + H⁺]<br>Found: 720.7712 |
| 31**d | 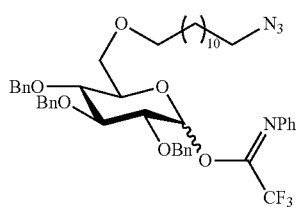 | $C_{47}H_{58}F_3N_4O_6$<br>Calc.: 832.9917 [M + H⁺]<br>Found: 832.9977 |

| comp. | structure | HRMS |
|---|---|---|
| 31**e | 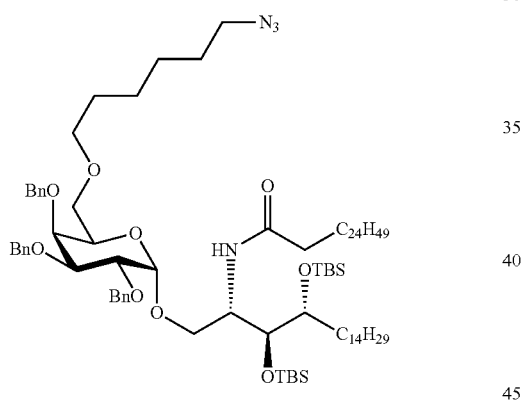 | $C_{43}H_{50}F_3N_4S_2O_6$<br>Calc.: 841.0174 [M + H$^+$]<br>Found: 841.0108 |
| 31**f | 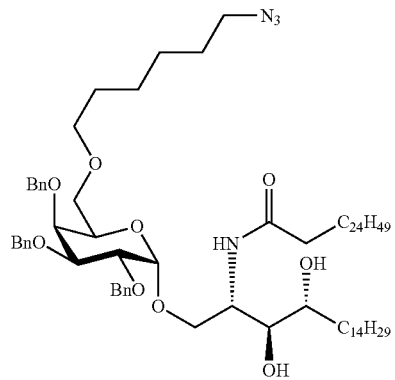 | $C_{37}H_{38}F_3N_4S_2O_6$<br>Calc.: 756.8577 [M + H$^+$]<br>Found: 756.8506 |

Example B.20: Synthesis of (2S,3S,4R)-3,4-bis-tert-butyldimethylsilyloxy-2-hexacosanoylamino-1-(6-(6'-azidohexyl)-2,3,4-tri-O-benzyl)-α-D-galactopyranosyl)octadecane (32*)

Nucleophile 23* (156 mg, 0.169 mmol) and glycosylating agent 31* (189 mg, 0.253 mmol) were co-evaporated with toluene three times and dried on high vacuum for 3 h after which they were dissolved in Et$_2$O (2 mL) and THF (0.4 mL) and cooled to 40° C. To the mixture was added TMSOTf (9.0 μL, 0.051 mmol) and the solution was warmed to 10° C. over the period of 3 h. The reaction was quenched by the addition of NEt$_3$ (0.05 mL) and solvents were removed in vacuo and the crude product was purified by silica flash column chromatography (gradient hexanes/EtOAc=10:1→4:1) to afford glycoside 32* (180 mg, 72% α-anomer) as a white foam.

[α]$_D^{r.t.}$=+18.9 (c=1, CHCl$_3$); R$_f$=0.46 (Hexanes/EtOAc=6.5:1); IR (film) ν$_{max}$ 3328, 2925, 2854, 2096, 1731, 1656, 1452, 1348, 1246, 1156, 1099, 1058, 835, 777, 696 cm$^{-1}$; $^1$H NMR (400 MHz, CDCl$_3$) δ 7.39-7.27 (m, 15H), 5.99 (d, J=7.07 Hz, 1H), 4.95 (d, J=11.5 Hz, 1H), 4.83 (d, J=3.7 Hz, 1H), 4.81-4.59 (m, 6H), 4.11-4.08 (m, 1H), 4.04 (dd, J=10.1, 3.6 Hz, 1H), 3.96-3.82 (m, 6H), 3.65 (ddd, J=7.0, 5.1, 1.85 Hz, 1H), 3.50-3.45 (m, 1H), 3.40 (dq, J=6.7, 4.0 Hz, 1H), 3.33-3.27 (m, 1H), 3.25 (t, J=6.9 Hz, 2H), 2.02-1.98 (m, 2H), 1.62-1.49 (m, 8H), 1.30-1.23 (m, 72H), 0.91-0.87 (m, 24H), 0.07 (s, 3H), 0.06 (s, 3H), 0.03 (s, 6H). $^{13}$C NMR (101 MHz, CDCl$_3$) δ 173.1, 138.8, 138.7, 138.6, 128.33, 128.30, 128.2, 128.1, 127.8, 127.6, 127.50, 127.46, 127.3, 100.2, 79.1, 77.20, 76.57, 75.7, 75.6, 74.9, 74.8, 73.4, 72.9, 71.4, 69.7, 69.4, 69.0, 51.8, 51.4, 36.8, 33.2, 31.9, 29.9, 29.74, 29.71, 29.66, 29.60, 29.5, 29.4, 28.8, 26.6, 26.14, 26.09, 25.7, 25.6, 22.7, 18.3, 18.2, 14.1, −3.7, −3.9, −4.6, −4.9; HR ESI Calcd for C$_{89}$H$_{156}$N$_4$O$_9$Si$_2$ [M+Na$^+$]: 1505.1333 found: 1505.1388.

Example B.21: Synthesis of (2S,3S,4R)-2-hexacosanoylamino-1-(6-(6'-azidohexyl)-2,3,4-tri-O-benzyl-α-D-galactopyranosyl)octadecane-3,4-diol (33*)

To a solution of bis-TBS ether 32* (16.0 mg, 10.8 μmol) in THF (1 mL) was added a solution of TBAF (1 M in THF, 0.150 mL, 0.15 mmol) slowly. After 3.5 h the reaction mixture was diluted with CH$_2$Cl$_2$ (10 mL). Solvents were removed in vacuo and crude product was purified by silica flash column chromatography (gradient hexanes/EtOAc=1:0→1:1) to afford diol 33* (10.5 mg, 78%) as a clear oil.

[α]$_D^{r.t.}$=+121.9 (c=0.2, CHCl$_3$); R$_f$=0.40 (Hexanes/EtOAc=2:1); IR (film) ν$_{max}$ 3329, 2919, 2851, 2096, 1640, 1543, 1467, 1455, 1350, 1094, 1046, 907, 730, 696 cm$^{-1}$; $^1$H NMR (400 MHz, CDCl$_3$) δ 7.32-7.18 (m, 15H), 6.34 (d, J=7.91 Hz, 1H), 4.88-4.51 (m, 7H), 4.15 (m, 1H), 3.98-3.96 (m, 1H), 3.88-3.74 (m, 5H), 3.41-3.21 (m, 6H), 3.17 (t, J=6.5 Hz, 2H), 2.19-2.08 (t, J=7.05 Hz, 2H), 1.53-1.35 (m, 8H), 1.31-1.18 (m, 72H), 0.81 (m, 6H); $^{13}$C NMR (101 MHz, CDCl$_3$) δ 173.0, 138.5, 138.3, 137.8, 128.44, 128.39, 128.2, 128.1, 128.1, 127.9, 127.62, 127.60, 127.4, 99.1, 79.3, 76.2, 76.0, 74.7, 74.5, 74.2, 73.2, 72.7, 71.4, 69.8, 51.3, 49.5, 36.7, 31.9, 29.7, 29.5, 29.4, 29.4, 29.3, 28.8, 26.5, 25.9, 25.7, 25.7, 22.7, 14.1; HR ESI Calcd for C$_{77}$H$_{128}$N$_4$O$_9$ [M+Na$^+$]: 1275.9574 found: 1275.9536.

Example B.22: Synthesis of (2S,3S,4R)-1-(6-(6'-aminohexyl)-α-D-galactopyranosyl)-2-hexacosanoyl-laminooctadecane-3,4-diol (34*)

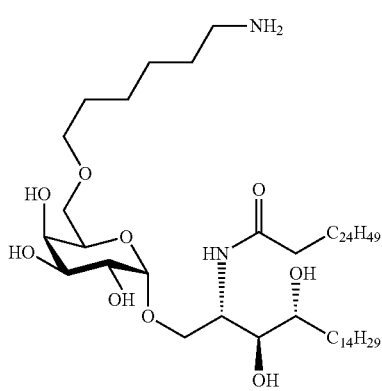

To a solution diol 33* (55 mg, 0.044 mmol) in EtOH (0.5 mL) and chloroform (0.15 mL) was added Pd(OH)$_2$ on charcoal (10% w/w, wet 38 mg). The solution was stirred at r.t. under an atmosphere of Ar for 15 min. after which H$_2$ gas was inserted into the suspension and the mixture was hydrogenated for 12 h. The mixture was filtered over celite and thoroughly washed with CH$_2$Cl$_2$, THF and MeOH. Solvents were removed in vacuo and the crude was purified by silica flash column chromatography on silica gel (CH$_2$Cl$_2$/MeOH=4:1) to afford linker equipped glycosphingolipid 34* (38 mg, 90%) as a pale yellow powder.

[α]$_D^{r.t.}$=+66.1 (c=1.0, Pyridine); R$_f$=0.44 (CH$_2$Cl$_2$/MeOH=4:1);

IR (film) ν$_{max}$ 3292, 2918, 2850, 1640, 1539, 1468, 1304, 1073, 1038, 970, 721 cm$^{-1}$;

$^1$H NMR (400 MHz, d-pyr) δ 8.88 (d, J=8.5 Hz, 1H), 5.54 (d, J=2.5 Hz, 1H), 5.24-5.21 (m, 1H), 4.62-4.55 (m, 3H), 4.44-4.32 (m, 5H), 4.00-3.92 (m, 2H), 3.31-3.26 (m, 2H), 2.56 (t, J=7.4 Hz, 2H), 2.22-2.18 (m, 1H), 2.00-1.90 (m, 2H), 1.90-1.78 (m, 4H), 1.73-1.60 (m, 1H), 1.55-1.47 (m, 2H), 1.44-1.20 (m, 70H), 0.87 (m, 6H); $^{13}$C NMR (101 MHz, d-pyr) δ 173.2, 100.4 (J$_{CH}$=169 Hz), 76.0, 72.2, 71.0, 70.9, 70.7, 70.6, 70.3, 69.6, 67.5, 50.4, 39.6, 36.5, 33.9, 31.8, 30.1, 29.9, 29.7, 29.68, 29.65, 29.62, 29.59, 29.5, 29.48, 29.28, 27.8, 26.3, 26.19, 26.17, 25.6, 22.6, 14.0; HR ESI Calcd for C$_{56}$H$_{112}$N$_2$O$_9$ [M+H$^+$]: 957.8441 found: 957.8468.

The following glycosphingolipids were prepared in a similar manner.

| Comp. | Structure | HRMS |
|---|---|---|
| 34*a | 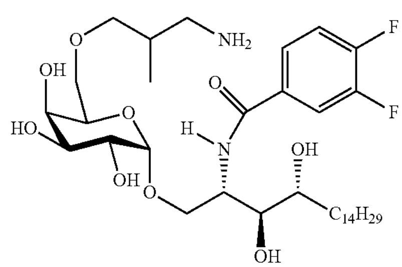 | C$_{35}$H$_{61}$F$_2$N$_2$O$_9$<br>Calc.: 692.8730 [M + H$^+$]<br>Found: 692.8707 |
| 34*b | 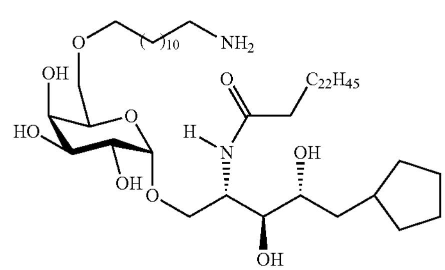 | C$_{52}$H$_{103}$N$_2$O$_9$<br>Calc.: 901.3922 [M + H$^+$]<br>Found: 901.3958 |
| 34*c | 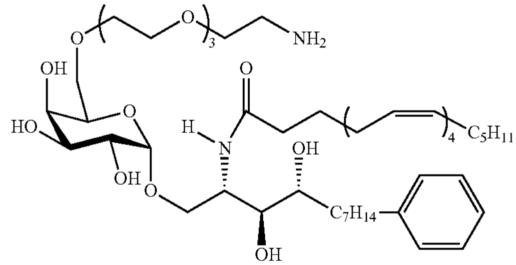 | C$_{51}$H$_{87}$N$_2$O$_{12}$<br>Calc.: 921.2527 [M + H$^+$]<br>Found: 921.2500 |

-continued
| Comp. | Structure | HRMS |
|---|---|---|
| 34*d | 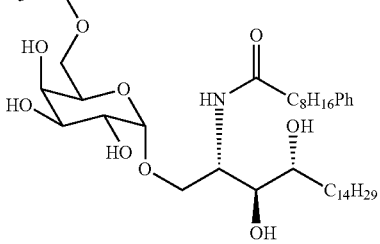 | C₄₅H₈₂N₂O₉<br>Calc: 795.6020 [M + H⁺]<br>Found: 795.5984 |
| 34*e | 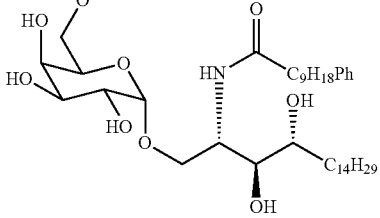 | C₄₆H₈₄N₂O₉<br>Calc: 809.6177 [M + H⁺]<br>Found: 809.6157 |
| 34*f | 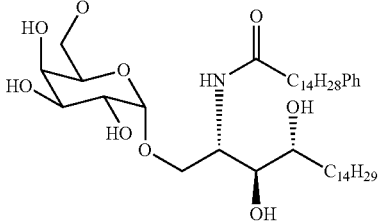 | C₅₁H₉₄N₂O₉<br>Calc: 879.6959 [M + H⁺]<br>Found: 879.6789 |
| 34*g | 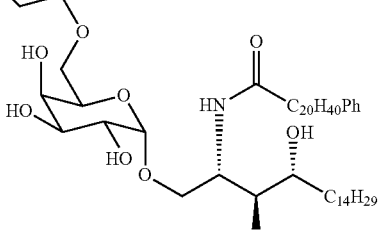 | C₅₇H₁₀₆N₂O₉<br>Calc: 963.7898 [M + H⁺]<br>Found: 963.7854 |

| Comp. | Structure | HRMS |
|---|---|---|
| 34*h | 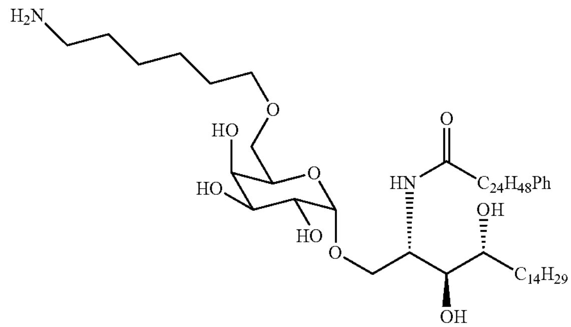 | $C_{61}H_{114}N_2O_9$<br>Calc: 1018.8524 [M + H⁺]<br>Found: 1018.8514 |
| 34*i | 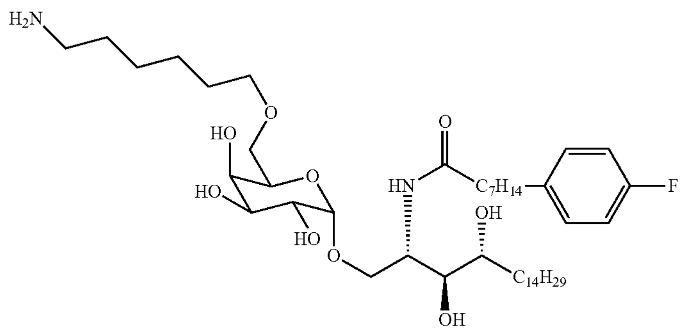 | $C_{44}H_{79}FN_2O_9$<br>Calc: 799.5770 [M + H⁺]<br>Found: 799.5755 |
| 34*j | 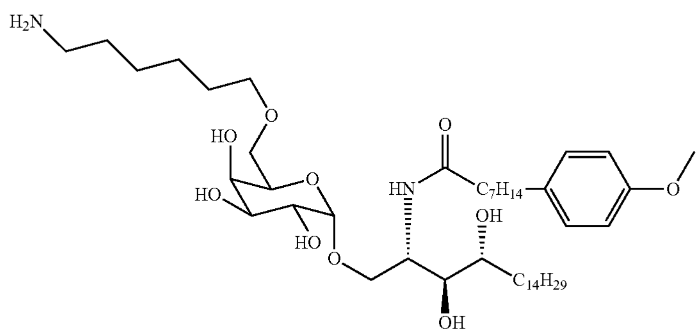 | $C_{45}H_{82}N_2O_9$<br>Calc: 811.5969 [M + H⁺]<br>Found: 811.5932 |
| 34*k | 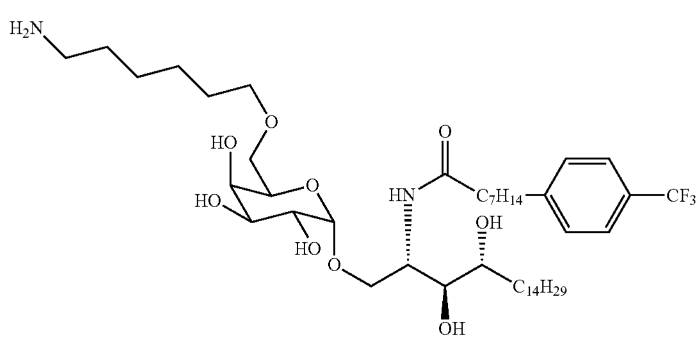 | $C_{45}H_{79}N_2O_9$<br>Calc: 849.5738 [M + H⁺]<br>Found: 849.5715 |

| Comp. | Structure | HRMS |
|---|---|---|
| 34*l | 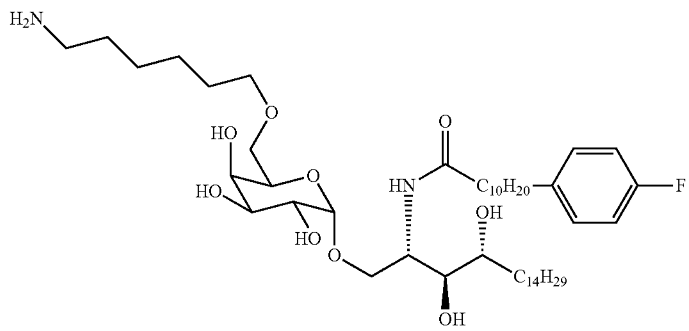 | $C_{47}H_{85}FN_2O_9$<br>Calc: 841.6239 [M + H$^+$]<br>Found: 841.6227 |
| 34*m | 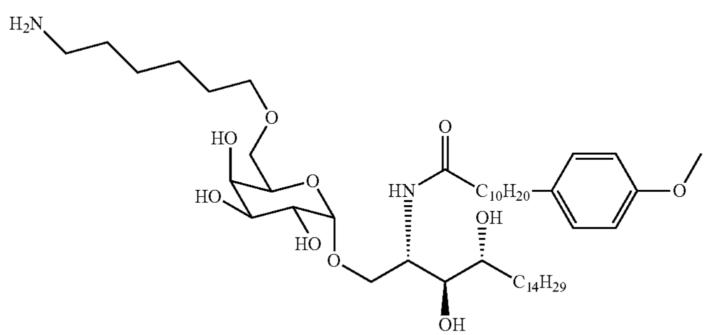 | $C_{45}H_{82}N_2O_9$<br>Calc: 853.6439 [M + H$^+$]<br>Found: 853.6430 |
| 34*n | 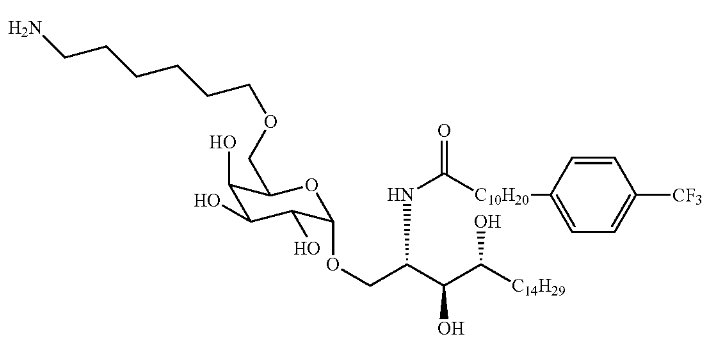 | $C_{45}H_{79}N_2O_9$<br>Calc: 891.6207 [M + H$^+$]<br>Found: 891.6198 |
| 34*o | 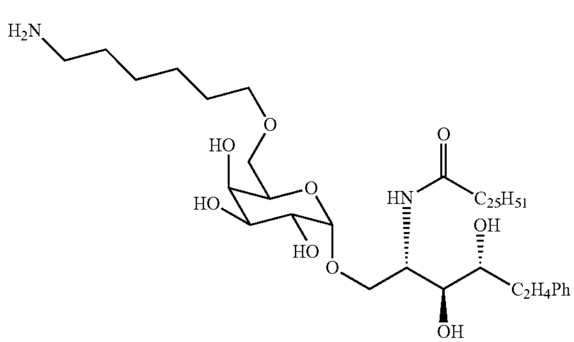 | $C_{50}H_{92}N_2O_9$<br>Calc: 864.6803 [M + H$^+$]<br>Found: 864.6809 |

| Comp. | Structure | HRMS |
|---|---|---|
| 34*p | (H2N-hexyl-O-galactopyranosyl linked structure with HN-C(O)-C25H51, OH, OH, C7H14Ph) | C55H102N2O9<br>Calc: 934.7585 [M + H+]<br>Found: 934.7536 |
| 34*q | (H2N-hexyl-O-galactopyranosyl linked structure with HN-C(O)-C23H47, OH, OH, C5H11) | C45H90N2O9<br>Calc: 803.6646 [M + H+]<br>Found: 803.6625 |
| 34*r | (H2N-hexyl-O-galactopyranosyl-S linked structure with HN-C(O)-C23H47, OH, OH, C14H29) | C54H108N2O8S<br>Calc: 945.7826 [M + H+]<br>Found: 945.7812 |

C. Synthesis of Conjugates

Example C.1: Synthesis of 2,5-dioxopyrrolidin-1-yl 5-((6-(((2R,3R,4S,5R,6S)-6-(((2S,3S,4R)-2-hexacosanamido-3,4-dihydroxyoctadecyl)oxy)-3,4,5-trihydroxytetrahydro-2H-pyran-2-yl)methoxy)hexyl)amino)-5-oxopentanoate (35*)

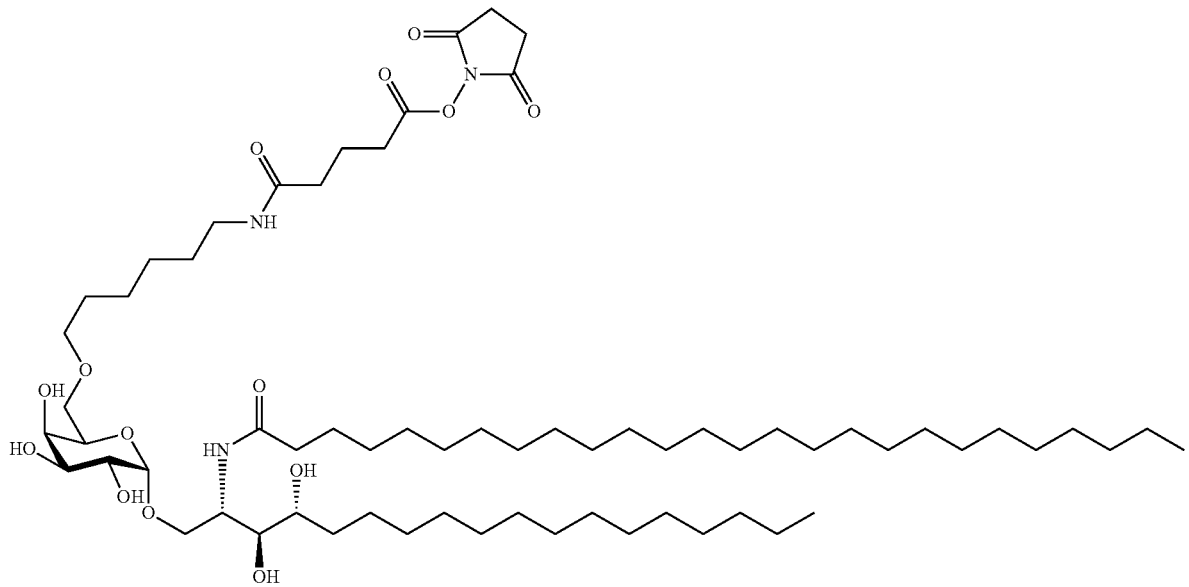

To glycosphingolipid 34* (10 mg, 10.44 µmol) in CHCl$_3$:MeOH:Et$_3$N mixture (1:1:0.1, 7 ml) was added excess glutaric anhydride (14.9 mg, 131 µmol) in one portion and left to stir at the r.t. After three days the completion of the reaction was indicated by the disappearance of the starting material mass on the LCMS, the reaction mixture was evaporated to dryness and the resultant residue was triturated with dichloromethane to give intermediate carboxylic acid (8 mg, 71.5%) as a white powder.

IR (film) v$_{max}$ 3300, 2918, 2850, 1718, 1637, 1539, 1466, 1304, 1073, 1038, 970, 719 cm$^{-1}$; $^1$H NMR (400 MHz, Pyridine-d$_5$) δ 8.45-8.33 (m, 2H), 5.53 (d, J=3.8 Hz, 1H), 5.29-5.18 (m, 1H), 4.63 (ddd, J=13.0, 9.9, 4.5 Hz, 2H), 4.46 (t, J=6.1 Hz, 1H), 4.44-4.25 (m, 5H), 4.02 (ddd, J=39.8, 9.9, 6.0 Hz, 2H), 3.46 (dq, J=13.3, 6.6 Hz, 4H), 2.66 (t, J=7.3 Hz, 2H), 2.57 (t, J=7.3 Hz, 2H), 2.44 (t, J=7.5 Hz, 2H), 2.37-2.21 (m, 3H), 1.97-1.74 (m, 4H), 1.75-1.62 (m, 1H), 1.61-1.50 (m, 4H), 1.47-1.06 (m, 65H), 0.86 (t, J=6.6 Hz, 6H); $^{13}$C NMR (101 MHz, pyridine) δ 172.78, 101.07, 76.28, 72.14, 71.08, 70.59, 70.44, 70.36, 69.79, 68.33, 50.90, 39.26, 36.43, 35.49, 33.94, 31.76, 30.03, 29.80, 29.74, 29.68, 29.64, 29.55, 29.47, 29.42, 29.25, 26.80, 26.14, 26.04, 25.83, 22.57, 21.73, 13.91; MALDI-TOF (THAP, RN) [M−H]$^−$ calcd 1069.861, found 1069.642.

To a solution of intermediate carboxylic acid (1.45 mg, 1.36 µmol) in DMSO:THF (1:1, 500 µL) was added N-hydroxysuccinimide (0.18 mg, 1.61 µmol) in one portion, followed by a solution of 1-ethyl-3-(3-dimethylaminopropyl)carbodiimide hydrochloride (1.3 mg, 6.78 µmol). After five days, disappearance of the starting material mass in LCMS indicated the completion of the reaction. 2-Mercaptoethanol (20 µL) was then added to the reaction mixture to quench the 1-ethyl-3-(3-dimethylaminopropyl)carbodiimide hydrochloride. NHS ester activated carboxylic acid 35* was used without any purification for coupling to the SP-3 capsular polysaccharide related saccharides:

HRMS (ESI) C$_{35}$H$_{122}$N$_3$O$_{14}$ [M+H]$^+$ calcd 1167.8921, found 1168.8931.

Example C.2: Synthesis of 4-nitrophenyl (6-(((2R,3R,4S,5R,6S)-6-(((2S,3S,4R)-2-hexacosanamido-3,4-dihydroxyoctadecyl)oxy)-3,4,5-trihydroxytetrahydro-2H-pyran-2-yl)methoxy)hexyl)carbamate (36*)

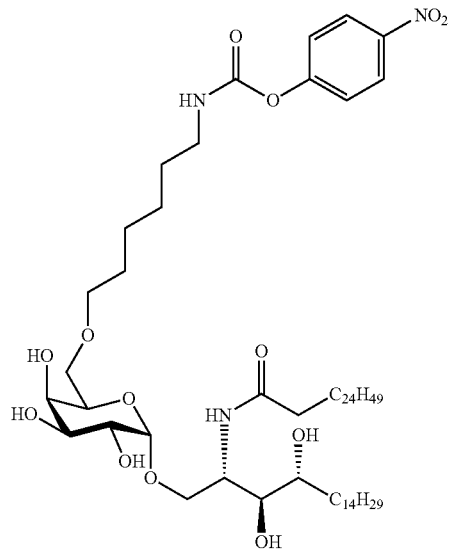

Glycosphingolipid 34* (3.9 mg, 4.1 µmol) was dissolved in 0.5 mL of dry pyridine, then to it was added bis(4-nitrophenyl)carbonate (6.1 mg, 20 µmol), followed by Et$_3$N (25 µl, 0.179 mmol). The resulting yellow solution was stirred at rt overnight, then concentrated in vacuo and purified by column chromatography on silica gel, using a gradient of 0-5-10-20% MeOH in DCM, yielding 3.6 mg (3.2 µmol, 79% yield) of glycosphingolipid 36* as a pale yellow oil. $^1$H NMR (400 MHz, pyridine) δ 9.02 (t, J=5.6 Hz, 1H), 8.49 (d, J=8.7 Hz, 1H), 8.26 (d, J=9.2 Hz, 2H), 7.54 (d, J=9.2 Hz, 2H), 5.56 (d, J=3.8 Hz, 1H), 5.26 (s, 2H), 4.67 (ddd, J=13.1, 10.0, 4.5 Hz, 2H), 4.51 (t, J=6.0 Hz, 1H), 4.41 (dd, J=9.0, 5.6 Hz, 2H), 4.35 (s, 2H), 4.10 (dd, J=9.8, 5.7 Hz, 1H), 4.02 (dd, J=9.8, 6.5 Hz, 1H), 3.52 (td, J=9.2, 2.7 Hz, 2H), 3.45 (dd, J=13.0, 6.9 Hz, 2H), 2.46 (t, J=7.2 Hz, 2H), 2.36-2.23 (m, 1H), 1.97-1.79 (m, 4H), 1.74-1.65 (m, 3H), 1.64-1.54 (m, 2H), 1.41 (d, J=7.1 Hz, 5H), 1.34-1.22 (m, 65H), 0.87 (t, J=6.7 Hz, 6H). $^{13}$C NMR (101 MHz, pyridine) δ 171.70, 155.90, 152.65, 143.22, 123.92, 121.09, 100.02, 75.15, 71.05, 70.01, 69.98, 69.62, 69.41, 69.35, 68.71, 67.28, 49.83, 40.13, 35.35, 32.84, 30.69, 30.68, 28.95, 28.73, 28.62, 28.59, 28.57, 28.55, 28.50, 28.48, 28.46, 28.41, 28.34, 28.19, 28.18, 25.59, 25.08, 24.98, 24.75, 21.51, 12.85.

HRMS: expected [M+Na]$^+$=1144.8322, found: 1444.8373.

Example C.3: Synthesis of N-(((2S,3S,4R)-1-(((2S,3R,4S,5R,6R)-6-(((6-(3-(2,5-dioxo-2,5-dihydro-1H-pyrrol-1-yl)propanamido)hexyl)oxy)methyl)-3,4,5-trihydroxytetrahydro-2H-pyran-2-yl)oxy)-3,4-dihydroxyoctadecan-2-yl)hexacosanamide (37*)

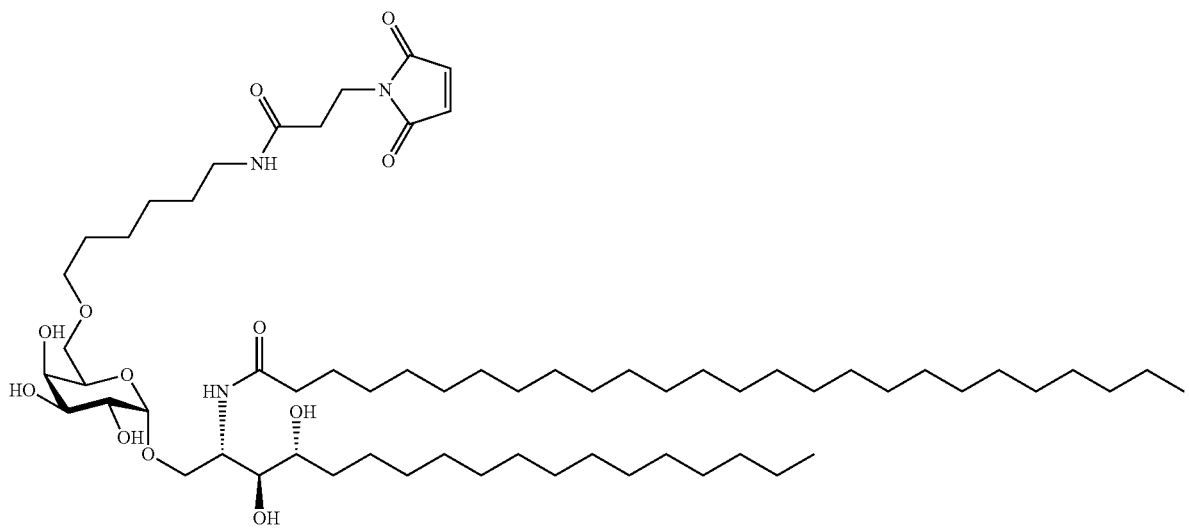

To a stirred solution of glycosphingolipid 34* (11.4 mg, 12 μmol) and DIPEA (5.3 μL, 30 μmol) in CHCl$_3$ (1.2 mL) and MeOH (0.4 mL) was added at room temperature N-succinimidyl-3-maleimidopropionate (7.9 mg, 30 μmol). The mixture was stirred for 2 h at that temperature and concentrated. The residue was purified by trituration with EtOAc (3 mL) and MeOH (3 mL) to give maleimide 37* (8.2 mg, 7.4 μmol) as a white solid.

$^1$H NMR (400 MHz, CD$_3$OD/CDCl$_3$ 1:3) δ 6.70 (s, 2H), 4.86 (d, J=3.8 Hz, 1H), 4.16-4.10 (m, 1H), 3.92-3.80 (m, 3H), 3.79-3.72 (m, 3H), 3.71-3.57 (m, 4H), 3.46 (m, 4H), 3.09 (t, J=7.1 Hz, 2H), 2.43 (t, J=7.2 Hz, 2H), 2.20-2.11 (m, 2H), 1.66-1.15 (m, 82H), 0.83 (t, J=6.8 Hz, 6H).

Example C.4: Synthesis of (2S,3S,4S,5R,6R)-methyl 6-(((2R,3S,4R,5R,6R)-6-(2-(benzyl((benzyloxy)carbonyl)amino)ethoxy)-2-((benzyloxy)methyl)-4,5-dihydroxytetrahydro-2H-pyran-3-yl)oxy)-4-(((2S,3R,4R,5S,6R)-6-((benzyloxy)methyl)-3,4-dihydroxy-5-(((2R,3R,4S,5S,6S)-3,4,5-trihydroxy-6-(methoxycarbonyl)tetrahydro-2H-pyran-2-yl)oxy)tetrahydro-2H-pyran-2-yl)oxy)-3,5-dihydroxytetrahydro-2H-pyran-2-carboxylate (38*)

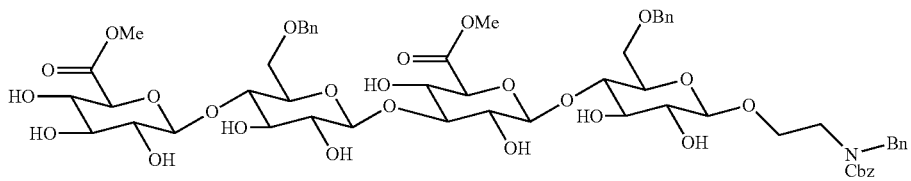 [SMILES: COC(=O)C1OC(OC2C(COCc3ccccc3)OC(OC3C(O)C(OC4C(COCc5ccccc5)OC(OCCN(Cc5ccccc5)C(=O)OCc5ccccc5)C(O)C4O)OC(C(=O)OC)C3O)C(O)C2O)C(O)C(O)C1O]

Tetrasaccharide 10* (30.0 mg, 0.026 mmol) was taken in methanol (5 mL) and treated with Amberlite®120H⁺ (5 mg) to it and heated to reflux for 24 h. The reaction mixture was cooled and filtered through cotton plug, washed thoroughly with MeOH (3 mL×4). Combined organics were evaporated in vacuum to get pale yellow solid (30 mg, 98%) corresponding to target compounds 38*.

¹H NMR (400 MHz, cd₃od) δ 7.56-6.86 (m, 20H), 5.14 (d, J=9.7 Hz, 2H), 4.70-4.33 (m, 9H), 4.22 (dd, J=32.2, 7.4 Hz, 1H), 3.99-3.72 (m, 11H), 3.70-3.40 (m, 15H), 3.39-3.32 (m, 2H), 3.29-3.15 (m, 2H).

Example C.5: Synthesis of (2S,3S,4S,5R,6R)-methyl 6-(((2R,3S,4R,5R,6R)-6-(2-aminoethoxy)-4,5-dihydroxy-2-(hydroxymethyl)tetrahydro-2H-pyran-3-yl)oxy)-4-(((2S,3R,4R,5S,6R)-3,4-dihydroxy-6-(hydroxymethyl)-5-(((2R,3R,4S,5S,6S)-3,4,5-trihydroxy-6-(methoxycarbonyl)tetrahydro-2H-pyran-2-yl)oxy)tetrahydro-2H-pyran-2-yl)oxy)-3,5-dihydroxytetrahydro-2H-pyran-2-carboxylate (39*)

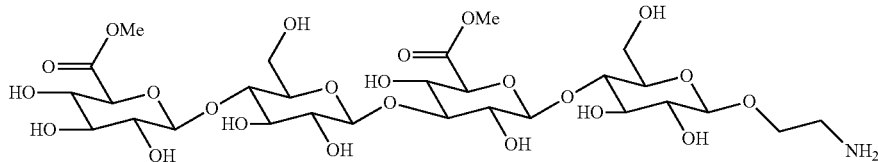 [SMILES: COC(=O)C1OC(OC2C(CO)OC(OC3C(O)C(OC4C(CO)OC(OCCN)C(O)C4O)OC(C(=O)OC)C3O)C(O)C2O)C(O)C(O)C1O]

Tetrasaccharide 38* (30.0 mg) was taken in methanol (5 mL) and added 10% Pd/C (30 mg) to it and stirred at 50 psi for 24 h. The reaction mixture was filtered through PTFE filter, washed thoroughly with methanol (3 mL×3), and with 10% aq. methanol (3 mL×3). Combined filtrate was evaporated in vacuum. 1H, HSQC nmr showed that still one benzyl group left. So, re subjected to same reaction conditions with ~10 mg of Pd/C added to material in methanol and hydrogenated at 60 psi for 16 h. RM was filtered through PTFE filter, washed thoroughly with methanol (3 mL×3), and with 10% aq methanol (3 mL×3). Combined filtrates were evaporated in vacuum to get white solid (18 mg, 89%) corresponding to target tetrasaccharide 39*.

¹H NMR (600 MHz, cd₃od) δ 4.65 (d, J=7.9 Hz, 1H), 4.56 (d, J=7.9 Hz, 1H), 4.47 (d, J=7.9 Hz, 1H), 4.38 (d, J=7.8 Hz, 1H), 4.05 (dt, J=11.5, 4.7 Hz, 1H), 4.02-3.98 (m, 1H), 3.96 (d, J=9.8 Hz, 1H), 3.94-3.84 (m, 4H), 3.84-3.76 (m, 5H), 3.65 (dd, J=5.9, 3.3 Hz, 2H), 3.58-3.44 (m, 8H), 3.41 (t, J=9.1 Hz, 1H), 3.38-3.32 (m, 3H), 3.30-3.24 (m, 2H), 3.17 (t, J=5.0 Hz, 2H).

Example C.5: Synthesis of (2S,3S,4S,5R,6R)-methyl 6-(((2R,3S,4R,5R,6R)-4,5-dihydroxy-2-(hydroxymethyl)-6-(2-(6-(4-nitrophenoxy)-6-oxohexanamido)ethoxy)tetrahydro-2H-pyran-3-yl)oxy)-4-(((2S,3R,4R,5S,6R)-3,4-dihydroxy-6-(hydroxymethyl)-5-(((2R,3R,4S,5S,6S)-3,4,5-trihydroxy-6-(methoxycarbonyl)tetrahydro-2H-pyran-2-yl)oxy)tetrahydro-2H-pyran-2-yl)oxy)-3,5-dihydroxytetrahydro-2H-pyran-2-carboxylate (40*)

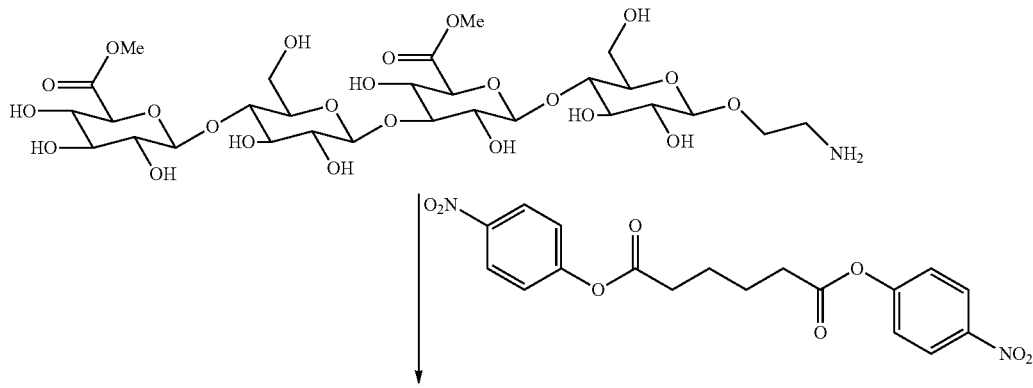

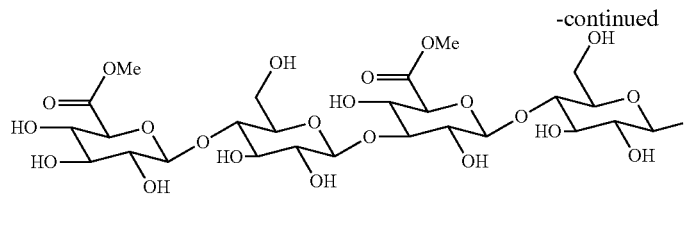
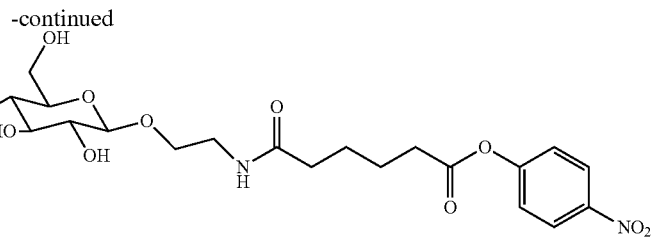

Tetrasaccharide 39* (3.0 mg, 3.92 μmol) and bis(4-nitrophenyl) adipate (9.89 mg, 0.025 mmol) were taken in a mixture of pyridine (1 mL) and DCM (1 mL) and stirred for 5 min, then treated with 5 μL of $Et_3N$ and stirred for 20 min. Solvents were removed under vacuum. Washed with DCM (3×1 mL) to remove excess adipate ester, and the remaining white solid was dried to get product 40* (3.9 mg, 98%). $^1$H NMR (400 MHz, $cd_3od$) δ 8.31 (d, J=8.8 Hz, 2H), 7.39 (d, J=8.9 Hz, 2H), 4.65 (d, J=7.8 Hz, 1H), 4.54 (d, J=7.8 Hz, 1H), 4.47 (d, J=7.8 Hz, 1H), 4.31 (d, J=7.7 Hz, 1H), 4.04-3.74 (m, 13H), 3.70-3.37 (m, 17H), 3.28-3.19 (m, 3H), 2.69 (t, J=10.0 Hz, 2H), 2.28 (t, J=5.9 Hz, 2H), 1.86-1.66 (m, 4H).

Example C.6: Synthesis of 4-nitrophenyl 6-((6-(((2R,3R,4S,5R,6S)-6-(((2S,3S,4R)-2-hexacosanamido-3,4-dihydroxyoctadecyl)oxy)-3,4,5-trihydroxytetrahydro-2H-pyran-2-yl)methoxy)hexyl)amino)-6-oxohexanoate (41*)

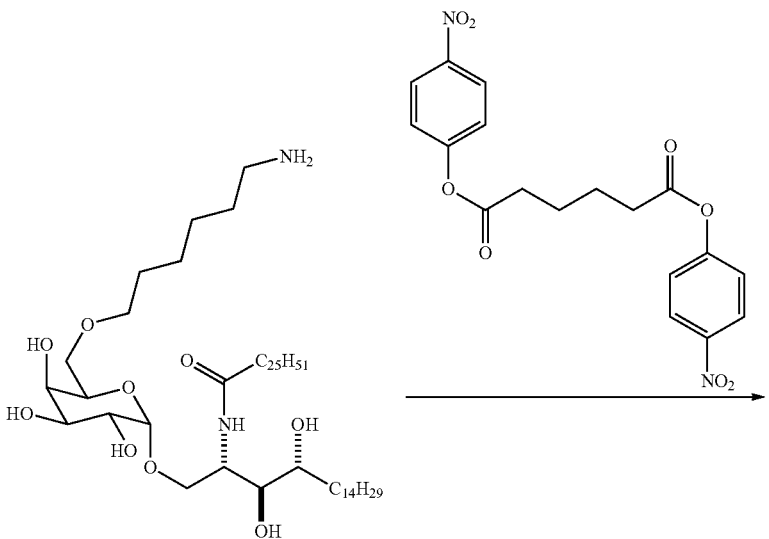

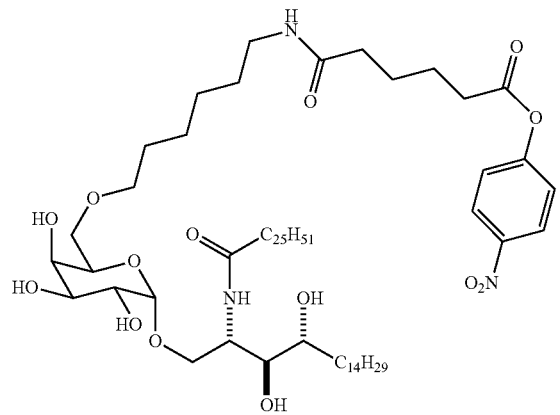

Glycosphingolipid 34* (13.0 mg, 0.014 mmol) and bis(4-nitrophenyl) adipate (26.0 mg, 0.068 mmol) were taken in a solvent mixture of pyridine (1 mL) and DCM (1 mL) at rt and stirred for 1 h, then treated with 5 μL of Et₃N and stirred for 15 min. Solvents were removed under vacuum to obtain a yellow solid. Crude product was purified the by flash chromatography using DCM and MeOH as eluent to obtain the compound 41* as white solid (8.5 mg, 52%).

$^1$H NMR (400 MHz, cd₃od) δ 8.23 (d, J=8.9 Hz, 2H), 7.25 (d, J=8.9 Hz, 2H), 4.85 (d, J=3.4 Hz, 1H), 4.12 (s, 1H), 3.94-3.79 (m, 3H), 3.78-3.53 (m, 4H), 3.51-3.39 (m, 4H), 3.13 (t, J=6.6 Hz, 2H), 2.60 (t, J=6.5 Hz, 2H), 2.16 (dt, J=15.1, 7.3 Hz, 4H), 1.82-1.10 (m, 84H), 0.82 (t, J=6.5 Hz, 6H).

Example C.7: Synthesis of (2S,3S,4S,5R,6R)-methyl 4-(((2S,3R,4R,5S,6R)-3,4-dihydroxy-6-(hydroxymethyl)-5-(((2R,3R,4S,5S,6S)-3,4,5-trihydroxy-6-(methoxycarbonyl)tetrahydro-2H-pyran-2-yl)oxy)tetrahydro-2H-pyran-2-yl)oxy)-6-(((2R,3S,4R,5R,6R)-6-(2-(6-((6-(((2R,3R,4S,5R,6S)-6-(((2S,3S,4R)-2-hexacosanamido-3,4-dihydroxyoctadecyl)oxy)-3,4,5-trihydroxytetrahydro-2H-pyran-2-yl)methoxy)hexyl)amino)-6-oxohexanamido)ethoxy)-4,5-dihydroxy-2-(hydroxymethyl)tetrahydro-2H-pyran-3-yl)oxy)-3,5-dihydroxytetrahydro-2H-pyran-2-carboxylate (42*)

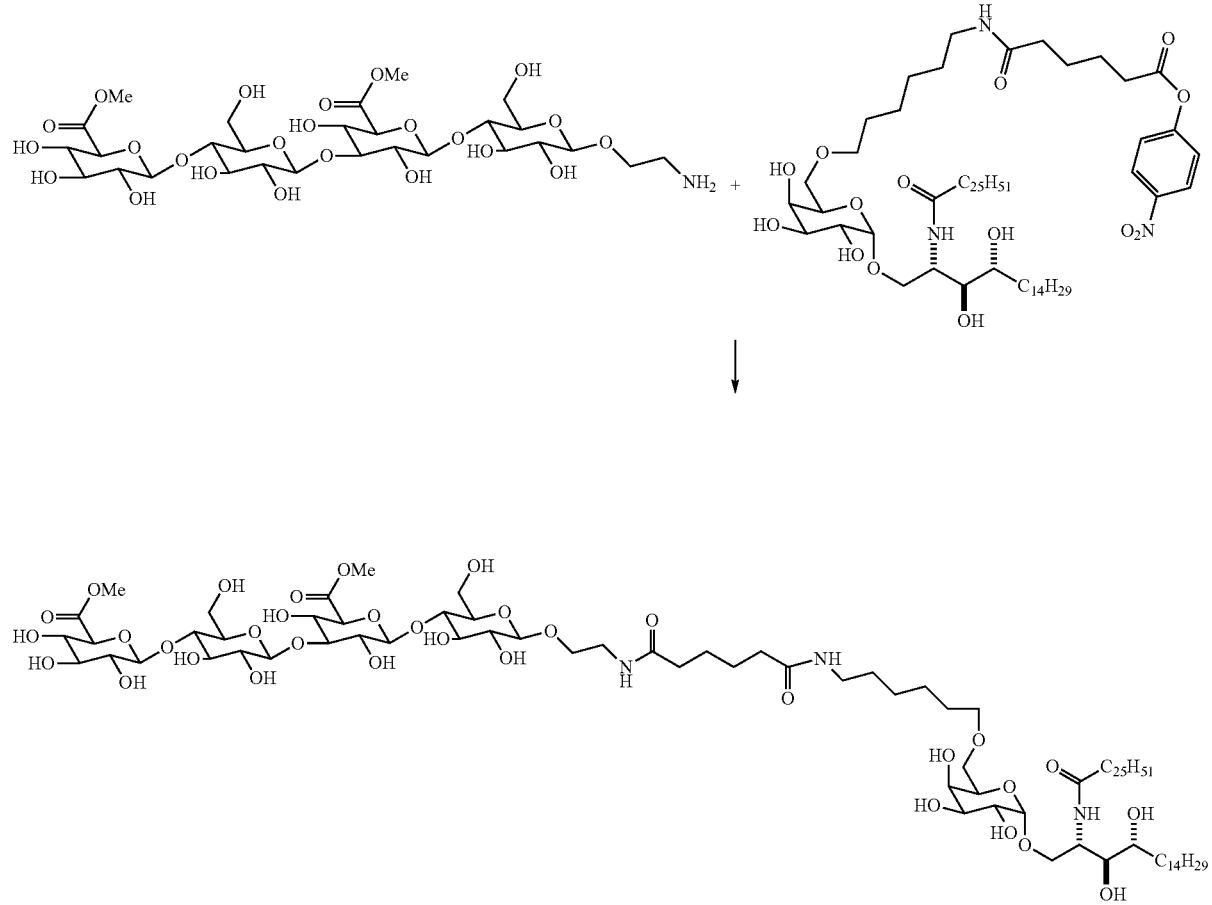

Tetrasaccharide 39* (4.6 mg, 6.01 μmol) and glycosphingolipid 41* (4.8 mg, 3.98 μmol) were dissolved in pyridine (1 mL)—DMSO (0.5 mL) solvent mixture and stirred for 15 min. HOBt (0.92 mg, 5.97 μmol) and triethylamine (30 μL) were added and the stirring was continued for 18 h. The reaction mixture was dried in vacuum and was purified by C18 Sep-Pak column using water-MeOH—CHCl₃ solvent combinations to get target product 42* as white solid (3.0 mg, 41%).

$^1$H NMR (600 MHz, cd₃od) δ 4.86 (d, J=3.7 Hz, 1H), 4.52 (d, J=7.9 Hz, 1H), 4.49 (d, J=7.8 Hz, 1H), 4.40 (d, J=8.0 Hz, 1H), 4.26 (d, J=7.8 Hz, 1H), 4.18-4.08 (m, 1H), 3.98-3.74 (m, 12H), 3.74-3.36 (m, 21H), 3.29-3.25 (m, 1H), 3.20-3.07 (m, 2H), 2.23-2.08 (m, 6H), 1.66-1.08 (m, 92H), 0.84 (t, J=7.0 Hz, 6H). MALDI-TOF: calculated for $C_{90}H_{165}N_3NaO_{34}$ [M+Na]⁺, 1856, found 1857.

Example C.8: Synthesis of (2S,3S,4S,5R,6R)-4-(((2S,3R,4R,5S,6R)-5-(((2R,3R,4S,5S,6S)-6-carboxy-3,4,5-trihydroxytetrahydro-2H-pyran-2-yl)oxy)-3,4-dihydroxy-6-(hydroxymethyl)tetrahydro-2H-pyran-2-yl)oxy)-6-(((2R,3S,4R,5R,6R)-6-(2-(6-((6-(((2R,3R,4S,5R,6S)-6-(((2S,3S,4R)-2-hexacosanamido-3,4-dihydroxyoctadecyl)oxy)-3,4,5-trihydroxytetrahydro-2H-pyran-2-yl)methoxy)hexyl)amino)-6-oxohexanamido)ethoxy)-4,5-dihydroxy-2-(hydroxymethyl)tetrahydro-2H-pyran-3-yl)oxy)-3,5-dihydroxytetrahydro-2H-pyran-2-carboxylic acid (43*)

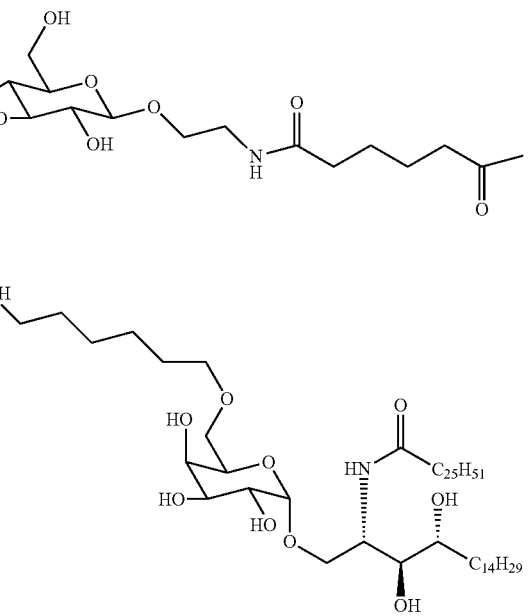

Conjugate 42* (0.55 mg, 0.296 mmol) was taken in methanol (0.5 mL)—THF (0.25 mL) at rt, treated with 30 μL of freshly prepared 0.05 M aq. NaOH solution, and stirred at rt for 1.5 h. The reaction mixture was neutralized with Amberlite® 120H⁺, then filtered through filter syringe, washed thoroughly with methanol-CHCl₃ solvent mixture (2 mL×3), and the filtrate was evaporated in vacuum to get white colored solid which was washed with CHCl₃ and decanted twice. The remaining white solid was dried in vacuum to get desired product 43* (0.41 mg, 77%).

$^1$H NMR (400 MHz, cd$_3$od) δ 4.86 (d, J=3.3 Hz, 1H), 4.60 (d, J=8.0 Hz, 1H), 4.49 (d, J=8.0 Hz, 1H), 4.41 (d, J=7.9 Hz, 1H), 4.28 (d, J=7.9 Hz, 1H), 4.19-4.11 (m, 1H), 3.96-3.76 (m, 9H), 3.73-3.37 (m, 19H), 3.14 (d, J=6.6 Hz, 2H), 2.28-2.09 (m, 6H), 1.79-1.06 (m, 92H), 0.85 (t, J=6.7 Hz, 6H). MALDI-TOF: calculated for $C_{88}H_{160}N_3NaO_{34}$ [M+Na-2H]⁺, 1826, found 1827.

D. Biological Evaluation

Example D.1: Synthesis of Liposomes (see FIG. 1)

Mixing of lipids and storage. A solution of liposome precursor was made by mixing conjugate 43* (0.2 mg, 0.111 μmol), 1,2-distearoyl-sn-glycero-3-phosphocholine (DSPC) (3.36 mg, 4.25 μmol) and cholesterol (1.1 mg, 2.85 μmol) in 2.2 mL of a solution of 1:4 chloroform:methanol. Then, this stock solution of 45 doses was split evenly in 5 glass vials of 5 cc volume, and each solution was evaporated in vacuo to a thin film on the glass, and stored under argon at −20° C. Each vial is meant to contain 9 doses of the liposomal formulation, reconstituted by hydrating the liposomes in 900 μL of phosphate buffer saline (PBS), so that each dose is 100 μL of the solution. One dose=4.4 μg (2.5 nmol) of conjugate 43*, which is equal to 1.7 μg of SP3 tetrasaccharide antigen (not including the linker).

Rehydration of the lipid films. On the day before each immunization, one frozen vial was thawed. Lipid film was rehydrated by adding 900 μL of sterile phosphate buffer saline (PBS) to the glass storage vial and stirring at 60° C. (T$_m$ of DSPC=55° C.) for one 30 min. (used a rotavap to stir the flask and the heat bath to control the temperature), yielding a mildly opalescent solution constituted of large multilamellar vesicles (LMV).

Lipid extrusion into defined liposomes. After rehydration of the lipid films, the resulting opalescent solution was taken up in a glass syringe and slowly extruded through a preheated (to 60° C.) lipid mini-extruder system equipped with the appropriate track-etch polycarbonate membrane between the two syringes (400 μm). Each solution was passed a minimum number of 31 times through the membrane.

Mini-extruder: Avanti Polar Lipids, inc. http://avantilipids.com/index.php?option=com_content&view=article&id=185&Itemid=193

Membrane: Whatman, Nucleopore, product #800282 (0.4 μm).

Analysis of liposomes. An aliquot of the liposomal solutions was loaded into a plastic UV cell and analyzed using dynamic light scattering (Malvern instruments, Zetasizer μV). The analysis confirmed the size and population distribution of each liposomal formulation. A uniform population with an observed diameter between 200 and 250 nm was observed.

Example D.2: Synthesis of CRM$_{197}$ Conjugate (44*)

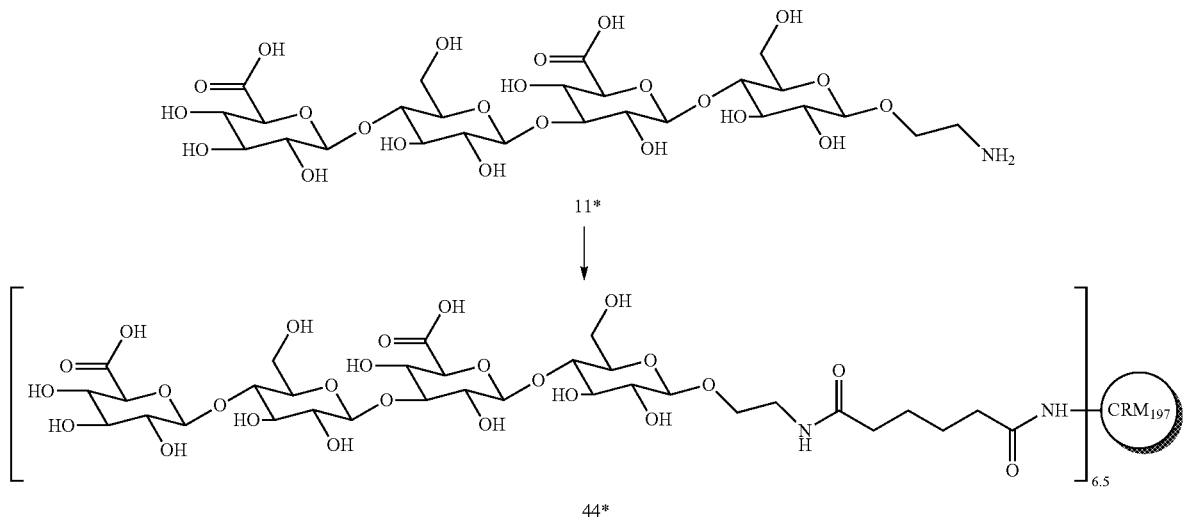

Tetrasaccharide 11* (2 mg, 2.8 nmol) solubilized in 100 µL anhydrous dimethyl sulfoxide (DMSO) was added dropwise to a stirred solution of di-N-hydroxy-succinimidyl adipate ester in 10-fold molar excess solubilized in 200 µL anhydrous DMSO with 10 µL triethylamine (Et$_3$N) and reacted for 2 h at room temperature. Then 0.4 ml of 100 mM Na-phosphate buffer, pH 7.4, was added and unreacted di-N-hydroxy-succinimidyl adipate ester was extracted twice with chloroform. The aqueous phase was recovered and reacted with 1 mg CRM$_{197}$ (Pfénex Inc., San Diego, Calif., USA) solubilized in 1 mL 100 mM Na-phosphate buffer, pH 7.4, at room temperature for 12 h. The reaction product was desalted and concentrated using 10 kDa centrifugal filters (Millipore). Protein concentration was determined with the Micro BCA Protein Assay Kit (Pierce) according to the manufacturer's recommendations.

SDS-PAGE

Figure 2:
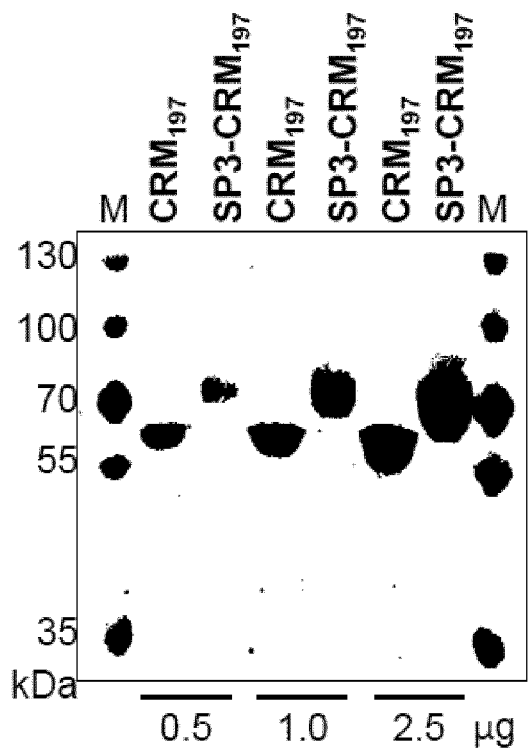
FIG. 2. Characterization of the SP3 tetrasaccharide-$CRM_{197}$ conjugate 44*:
(a) SDS-PAGE; (b) MALDI-TOF-MS.
Figure 2:
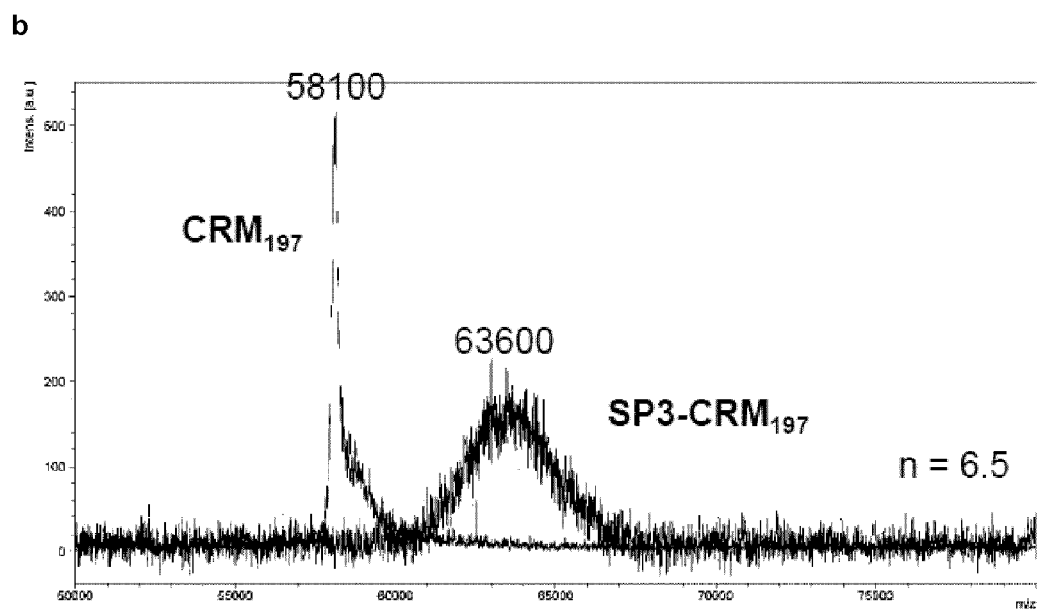

Samples were dissolved in Lammli buffer (0.125 M Tris, 20% (v/v) glycerol, 4% (w/v) SDS, 5% (v/v) beta-mercaptoethanol, bromophenol blue, pH 6.8) and boiled at 95° C. for 10 min. Samples were run in 10% polyacrylamide gels and stained with 0.025% Coomassie Brilliant Blue R-250 in an aqueous solution containing 40% (v/v) methanol and 7% (v/v) acetic acid. Characterization of the conjugate 44* by sodium dodecyl sulfate-polyacrylamide gel electrophoresis (SDS-PAGE) revealed an expected shift of the glycoconjugate towards higher masses and band broadening compared to unconjugated CRM$_{197}$ carrier protein (see FIG. 2a).

MALDI-TOF Mass Spectrometry

MALDI-TOF mass spectra of CRM$_{197}$ and SP3 tetrasaccharide CRM$_{197}$ conjugate 44* were obtained using an Autoflex Speed instrument (Bruker Daltonics, Bremen, Germany). The mass spectrometer was operated in positive linear mode. Spectra were acquired over an m/z range from 30,000 to 210,000 and data was analyzed with the Flex-Analysis software provided with the instrument. 2',4'-dihydroxyacetophenone (DHAP) was used as matrix, samples were spotted using the dried droplet technique. MALDI-TOF-MS measurement reveals that conjugate 44* presents an antigen loading of ~6.5 molecules of SP3 tetrasaccharide per molecule CRM$_{197}$ on average (see FIG. 2b).

Example D.3: Immunizations

Two groups (six mice each) of six to eight-weeks old female C57BL/6 mice (purchased from Charles River, Germany) were immunized subcutaneously (s.c.) with SP3 tetrasaccharide liposomes obtained at example D.1 (1.7 µg of SP3 tetrasaccharide antigen per mouse) or with SP3 tetrasaccharide-CRM$_{197}$ conjugate 44* prepared at example D.2 corresponding to 1.7 µg SP3 tetrasaccharide antigen per mouse with Alum adjuvant. The conjugate 44* was mixed with Alhydrogel (Brenntag) (1 µL Alhydrogel per µg protein) and incubated at 4° C. at least 12 h prior to the immunizations. Blood was collected in one-week intervals via the tail vein. Sera were separated from erythrocytes by centrifugation.

Example D.4: Preparation of Microarrays

Oligosaccharides bearing an amine linker, or proteins, were immobilized on CodeLink N-hydroxyl succinimide (NHS) ester activated glass slides (SurModics Inc., Eden Prairie, Minn., USA) with a piezoelectric spotting device (S3; Scienion, Berlin, Germany). Microarray slides were incubated in a humid chamber to complete reaction for 24 h, quenched with 50 mM aminoethanol solution, pH 9 for 1 h at 50° C., washed three times with deionized water, and stored desiccated until use.

Example D.5: Microarray Binding Assays

Slides were blocked with 1% bovine serum albumin (BSA) in phosphate-buffered saline (PBS) (w/v) for 1 h at room temperature, washed three times with PBS and dried by centrifugation (300×g, 5 min.). A FlexWell 64 (Grace Bio-Labs, Bend, Oreg., USA) grid was applied to microarray slides. Resulting 64 wells were used for 64 individual experiments. Slides were incubated with serum, diluted 1:200 with 1% BSA in PBS (w/v) in a humid chamber for 1 h at room temperature, washed three times with 0.1% Tween-20 in PBS (v/v) and dried by centrifugation (300×g, 5 min.). Slides were incubated with fluorescence-labeled secondary antibodies diluted in 1% BSA in PBS (w/v) in a humid chamber for 1 h at room temperature, washed three times with 0.1% Tween-20 in PBS (v/v), rinsed once with deionized water and dried by centrifugation (300×g, 5 min.) prior to scanning with a GenePix 4300A microarray scanner (Molecular Devices, Sunnyvale, Calif., USA). Image analysis was carried out with the GenePix Pro 7 software (Molecular Devices). The photomultiplier tube (PMT) voltage was adjusted such that scans were free of saturation signals. Background-subtracted mean fluorescence intensity (MFI) values were exported to Microsoft Excel for further analyses. Secondary antibodies used were: Alexa Fluor® 594 Goat Anti-Mouse IgG1 (γ1) (Life Technologies) diluted 1:400, Alexa Fluor® 647 Goat Anti-Mouse IgG2a (γ2a) (Life Technologies) diluted 1:200, Alexa Fluor® 488 Goat Anti-Mouse IgG3 (γ3) (Life Technologies) diluted 1:200.

Figure 3:
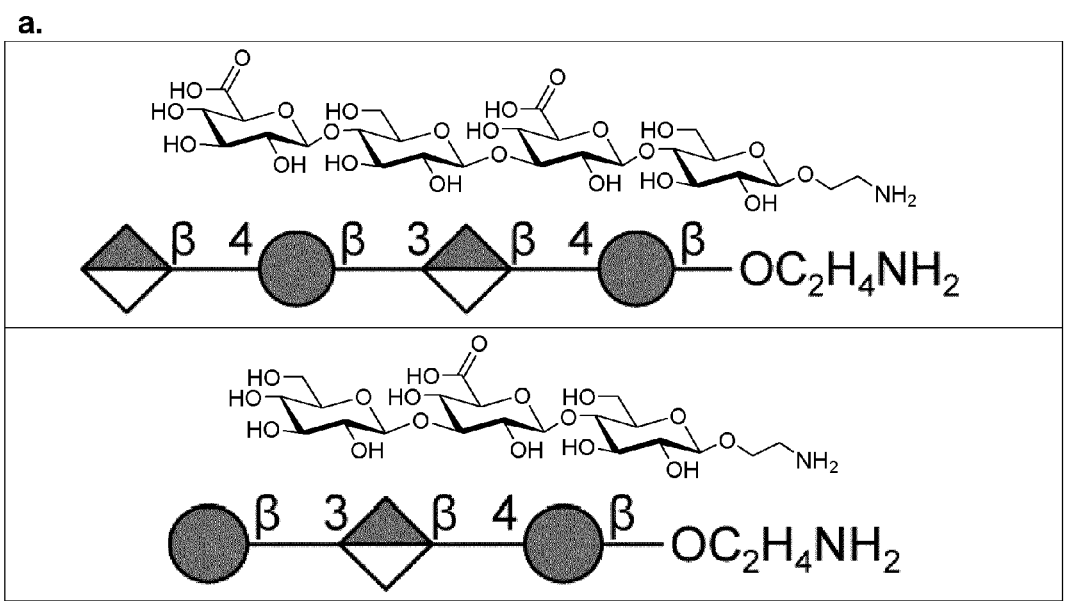
FIG. 3. Primary antibody response against the liposome containing conjugate 43* and SP3 tetrasaccharide-$CRM_{197}$ conjugate 44* in mice:
(a) representation of the printed saccharide with symbols;
(b) microarray printing pattern;
(c) immune response of a mouse immunized with the liposome containing the conjugate 43* (time frame: day 0 to week 2);
(d), (e), (f) comparison of the primary antibody response against the liposomes containing conjugate 43* and SP3 tetrasaccharide-$CRM_{197}$ conjugate 44* (averaged data of six mice of both groups).
Figure 3:
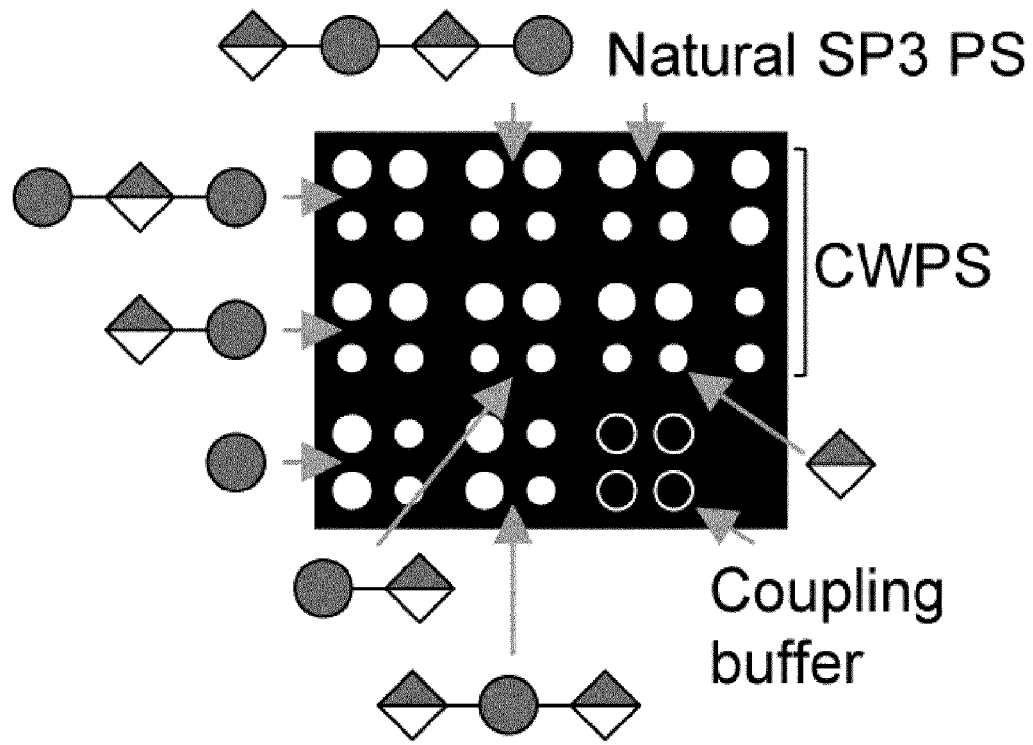
Figure 3:
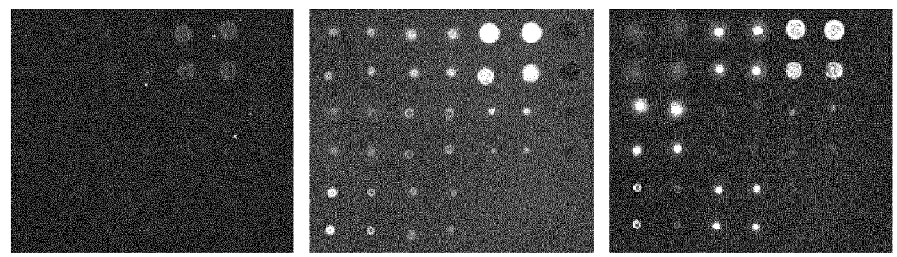
Figure 3:
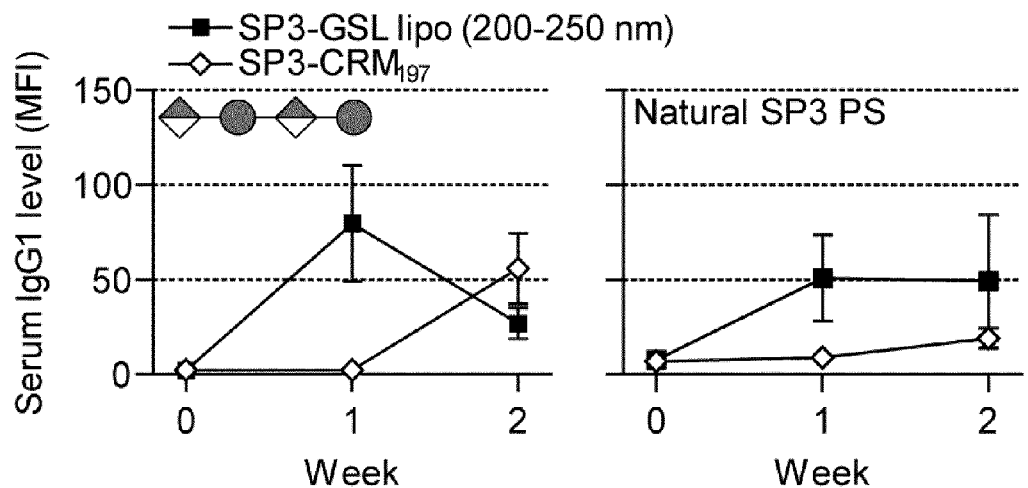
Figure 3:
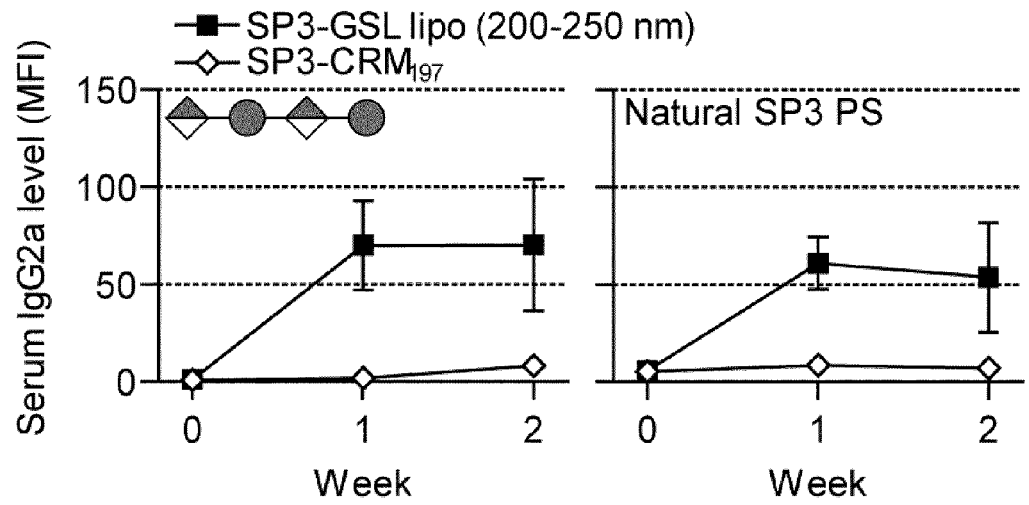
Figure 3:
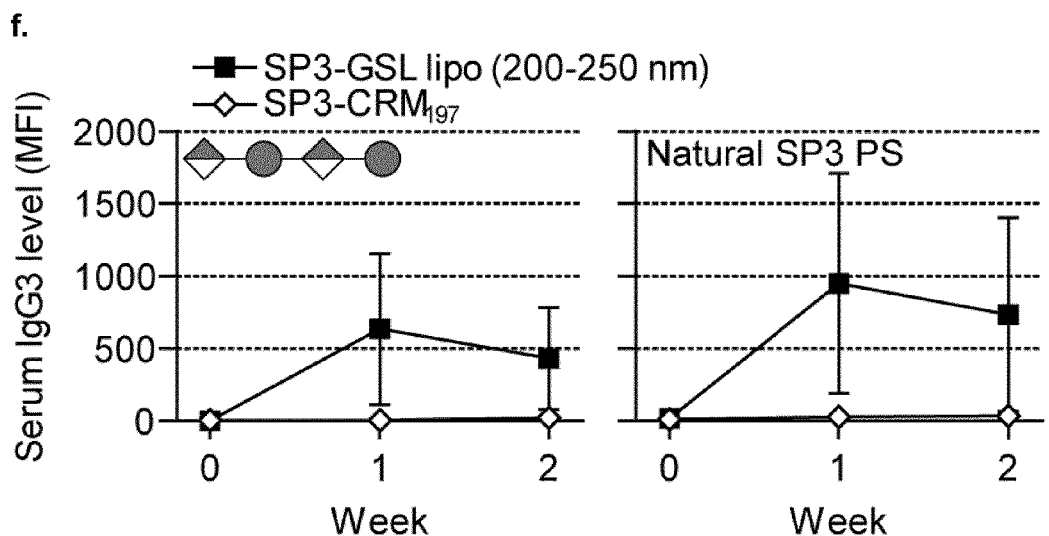

The primary immune response was assessed by glycan microarray screening of serum samples retrieved at weeks 0, 1 and 2. SP3 oligosaccharides, natural SP3 polysaccharide as well as S. pneumoniae cell wall polysaccharide (CWPS) as negative control were printed on NHS ester-activated microarray slides (see FIG. 3b). Representative microarray scans of one mouse immunized with SP3 liposomes are shown in FIG. 3c, indicating that IgG3 antibodies were elicited against the immunogen, the SP3 tetrasaccharide, as well as smaller substructures and the natural SP3 polysaccharide. No antibodies against the CWPS were detected in any of the mice, demonstrating the specificity of the antibody response towards SP3-related antigens. Cross-reactivity to the natural SP3 polysaccharide gives a first indication that the antibodies are capable of binding to the surface of S. pneumoniae bacteria so that to promote protection. After immunization with SP3 liposomes containing conjugate 43*, antibodies of the IgG1, IgG2a and IgG3 subtypes against the SP3 tetrasaccharide as well as against the natural SP3 polysaccharide in all immunized mice were detected (FIGS. 3d, 3e, 3f show averaged data of six mice of both groups). IgG2a and IgG3 antibodies were only detected in mice immunized with SP3 liposomes containing conjugate 43*, not in those immunized with the SP3-CRM$_{197}$ conjugate 44*. The SP3-CRM$_{197}$ conjugate 44* elicited IgG1 antibodies only two weeks after the immunization. Antibody responses after immunization with SP3 liposomes containing conjugate 43* were faster and were detectable already one week after the immunization.

These data demonstrate the immunogenicity of the conjugate 43* formulated as liposomes. Serum IgG responses in mice were superior to the SP3-CRM$_{197}$ conjugate 44* in terms of kinetics and IgG2a and IgG3 production. Isotype switching indicates T cell-dependent antibody responses. Serum IgG antibodies were detectable one week after the first immunization with the conjugate 43* formulated as liposomes. Antibodies cross-reacting with the natural SP3 polysaccharide indicates the potential of these antibodies to bind to S. pneumoniae bacteria and to confer protection against pneumococcal infection.

The invention claimed is:

1. A conjugate of general formula (I-A)

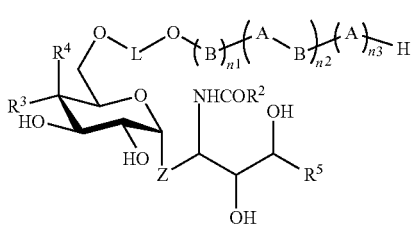

I-A wherein
A is

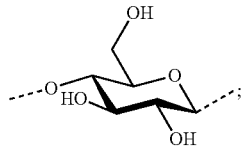

B is

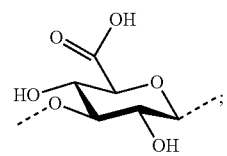

$R^2$ is $-(X^1)_{p1}-(X^2)_{p2}-(X^3)_{p3}-X^4$;
$R^3$ and $R^4$ are selected from $-H$ and $-OH$ and cannot be simultaneously $-H$ or $-OH$;
$R^5$ is $-(Y^1)_{m1}-(Y^2)_{m2}-(3)_{m3}-Y^4$;
Z represents $-O-CH_2-$, $-S-CH_2-$ or $-CH_2-CH_2-$;
$X^4$ represents: $-H$ or

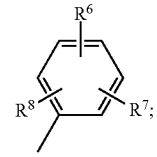

$Y^4$ represents: $-H$ or -Ph;
$X^1$, $X^2$, $X^3$, $Y^1$, $Y^2$, $Y^3$ are independently of each other selected from: $-CH_2-$,

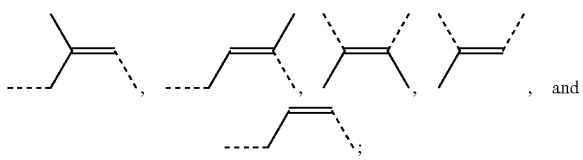

, and n2 is an integer selected from 1, 2, 3, 4, 5, 6, 7, 8, 9 and 10;
n1, n3 represent independently of each other an integer selected from 0 and 1;
L represents $-L^1-NH-L^2-NH-L^3-$;
$L^1$ represents $-L^{1'}-L^{1''}-L^{1'''}-$ or $-L^{1'}-L^{1''}-$ or $-L^{1'}-$; and
$L^3$ represents $-L^{3'}-L^{3''}-L^{3'''}-$ or $-L^{3'}-L^{3''}-$ or $-L^{3'}-$; and
$L^{1'}$, $L^{1''}$, $L^{1'''}$, $L^{3'}$, $L^{3''}$, and $L^{3'''}$ are independently of each other selected from: $-CH_2-$, $-C_2H_4-$, $-C_3H_6-$, $-C_4H_8-$, $-C_5H_{10}-$, $-C_6H_{12}-$, $-C_7H_{14}-$, $-C_8H_{16}-$, $-C_9H_{18}-$, $-C_{10}H_{20}-$, $-(CH_2-CH_2-O)_o-CH_2-CH_2-$, and $-(CH_2-CH_2-O)_o-CH_2-$;

$L^2$ is selected from: —C(O)—,

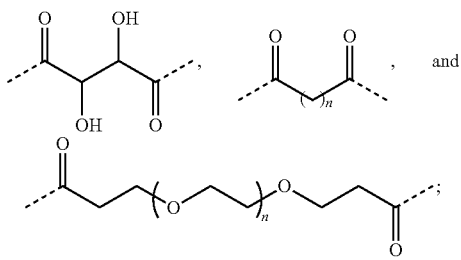

and $R^6$, $R^7$ and $R^8$ are independently of each other selected from: —H, —CH$_3$, —C$_2$H$_5$, —F, —Cl, —Br, —OCH$_3$ and —CF$_3$;

n and o represent independently of each other an integer selected from 1, 2, 3, 4, 5 and 6;

p1, p2, p3, m1, m2 and m3 represent independently of each other an integer from 0 to 10.

2. The conjugate according to claim 1 general formula (I-B)

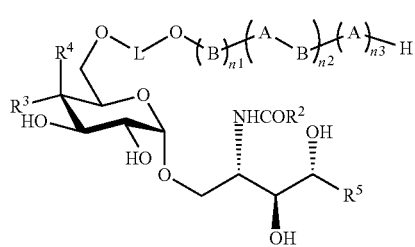

wherein
A is

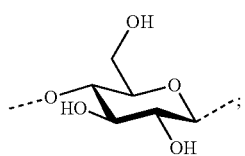

B is

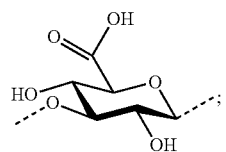

$R^2$ is —(X$^1$)$_{p1}$—(X$^2$)$_{p2}$—(X$^3$)$_{p3}$—X$^4$;
$R^3$ and $R^4$ are selected from —H and —OH and cannot be simultaneously —H or —OH;
$R^5$ is —(Y$^1$)$_{m1}$—(Y$^2$)$_{m2}$—(Y$^3$)$_{m3}$—Y$^4$;

$X^4$ represents:

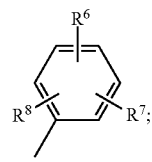

$Y^4$ represents: —H or -Ph;
$X^1$, $X^2$, $X^3$, $Y^1$, $Y^2$ and $Y^3$ are independently of each other selected from:
—CH$_2$—, and

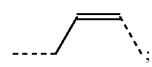

n2 is an integer selected from 1, 2, 3, 4, 5, 6, 7, 8, 9 and 10;
n1 and n3 represent independently of each other an integer selected from 0 and 1;
L represents -L$^1$-NH-L$^2$-NH-L$^3$-;
L$^1$ represents -L$^{1'}$-L$^{1''}$-L$^{1'''}$- or -L$^{1'}$-L$^{1''}$- or -L$^{1'}$-; and
L$^3$ represents -L$^{3'}$-L$^{3''}$-L$^{3'''}$- or -L$^{3'}$-L$^{3'''}$- or -L$^{3'}$-; and
L$^{1'}$, L$^{1''}$, L$^{1'''}$, L$^{3'}$, L$^{3''}$, and L$^{3'''}$ are independently of each other selected from: —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—;
$L^2$ is selected from: —C(O)—,

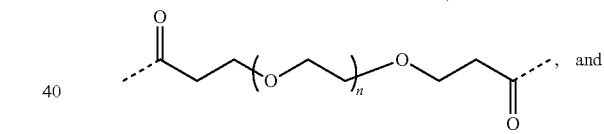
, and

$R^6$, $R^7$ and $R^8$ are independently of each other selected from: —H, —CH$_3$, —C$_2$H$_5$, —F, —Cl, —Br, —OCH$_3$ and —CF$_3$;
n represents an integer selected from 1, 2, 3, 4, 5 and 6;
p1, p2, p3, m1, m2 and m3 represent independently of each other an integer from 0 to 10.

3. The conjugate according to claim 1, wherein $R^3$ is —H and $R^4$ is —OH.

4. The conjugate according to claim 1 general formula (I-C)

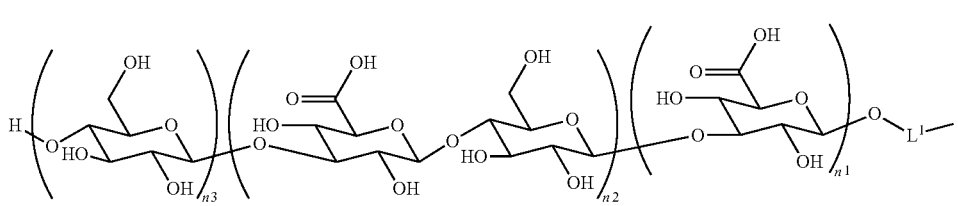

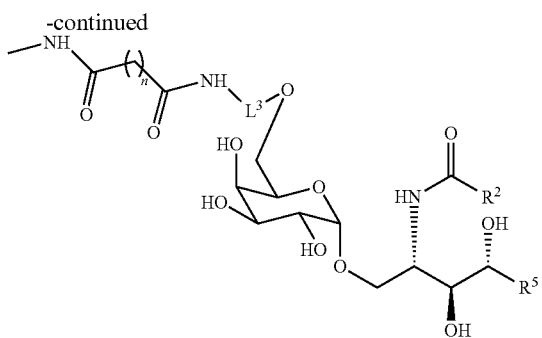

wherein
R² is —(X¹)$_{p1}$—(X²)$_{p2}$—(X³)$_{p3}$—X⁴;
R⁵ is —(Y¹)$_{m1}$—(Y²)$_{m2}$—(Y³)$_{m3}$—Y⁴;
X⁴ represents: —H

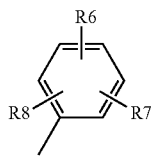

Y⁴ represents —H or -Ph;
X¹, X², X³, Y¹, Y², Y³ are independently of each other selected from:
—CH₂—,

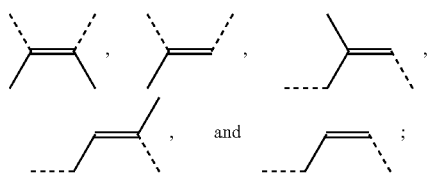

n2 is an integer selected from 1, 2, 3, 4, 5, 6, 7, 8, 9 and 10;
n1, n3 represent independently of each other an integer selected from 0 and 1;
L¹ represents -L¹'-L¹''-L¹'''- or -L¹'-L¹''- or -L¹'-; and
L³ represents -L³'-L³''-L³'''- or -L³'-L³''- or -L³'-; and
L¹', L¹'', L¹''', L³', L³'', and L³''' are independently of each other selected from: —CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —(CH₂—CH₂—O)$_o$—CH₂—CH₂— and —(CH₂—CH₂—O)$_o$—CH₂—;
R⁶, R⁷ and R⁸ are independently of each other selected from: —H, —CH₃, —C₂H₅, —F, —Cl, —Br, —OCH₃ and —CF₃;
R⁹ to R²⁰ represent independently of each other —H, —CH₃, —C₂H₅, or —C₃H₇;
o represents an integer selected from 1, 2, 3, 4, 5 and 6;
n represents an integer selected from 1, 2, 3, 4, 5 and 6;
p1, p2, p3, m1, m2 and m3 represent independently of each other an integer from 0 to 10.

5. The conjugate according to claim 1, wherein R² is selected from —(CH₂)₂₄—CH₃, —(CH₂)₂₃—CH₃, —(CH₂)₂₂—CH₃, —(CH₂)₂₁—CH₃, —(CH₂)₂₀—CH₃, —(CH₂)₁₉—CH₃, —(CH₂)₁₈—CH₃, —(CH₂)₁₇—CH₃, —(CH₂)₁₆—CH₃, —(CH₂)₁₅—CH₃, —(CH₂)₁₄—CH₃, —(CH₂)₁₃—CH₃, —(CH₂)₁₂—CH₃, —(CH₂)₁₁—CH₃, —(CH₂)₁₀—CH₃, —(CH₂)₉—CH₃, —(CH₂)₈—CH₃,

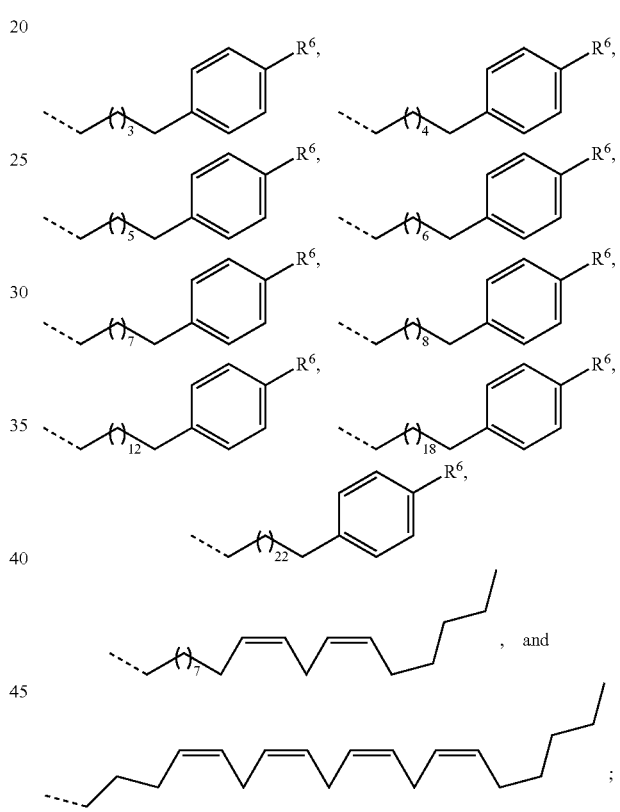

and R⁶ is selected from: —H, —CH₃, —F, —Cl, —OCH₃ and —CF₃.

6. The conjugate according to claim 1, wherein R⁵ is selected from —(CH₂)₁₃—CH₃, —(CH₂)₁₂—CH₃, —(CH₂)₁₁—CH₃, —(CH₂)₁₀—CH₃, —(CH₂)₉—CH₃, —(CH₂)₈—CH₃, —(CH₂)₇—CH₃, —(CH₂)₆—CH₃, —(CH₂)₅—CH₃, —(CH₂)₄—CH₃, —(CH₂)₂-Ph, —(CH₂)₃-Ph, —(CH₂)₄-Ph, —(CH₂)₅-Ph, —(CH₂)₆-Ph, —(CH₂)₇-Ph, —(CH₂)₈-Ph, and —(CH₂)₉-Ph.

7. The conjugate according to claim 1, wherein -L¹- and -L³- are independently of each other selected from: —CH₂—, —C₂H₄—, —C₃H₆—, —C₄H₈—, —C₅H₁₀— and —C₆H₁₂—.

8. A pharmaceutical composition comprising a conjugate according to claim 1 together with at least one pharmaceutically acceptable acceptable carrier, excipient and/or diluent.

9. The conjugate according to claim 4, wherein $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_{9}$—$CH_3$, —$(CH_2)_{8}$—$CH_3$,

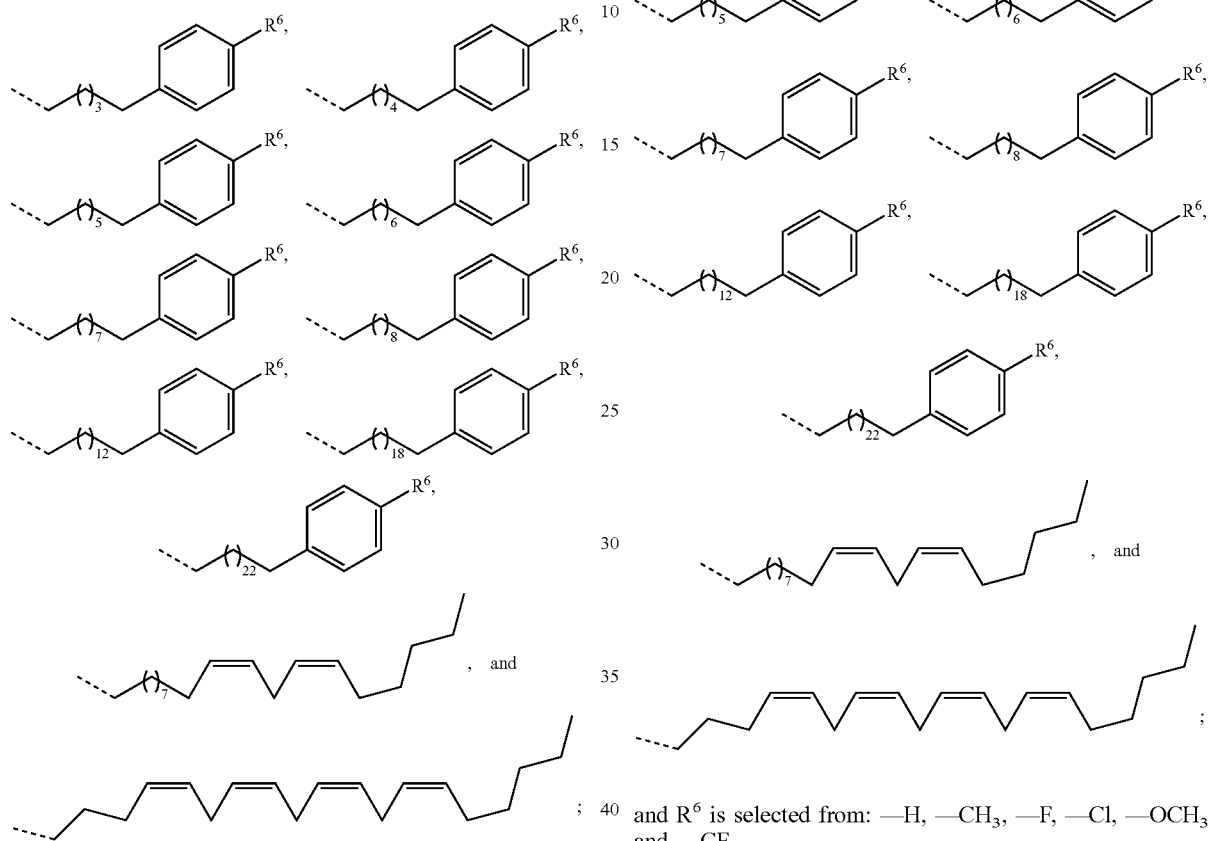

and $R^6$ is selected from: —H, —$CH_3$, —F, —Cl, —$OCH_3$ and —$CF_3$.

10. The conjugate according to claim 4, wherein $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_{9}$—$CH_3$, —$(CH_2)_{8}$—$CH_3$, —$(CH_2)_{7}$—$CH_3$, —$(CH_2)_{6}$—$CH_3$, —$(CH_2)_{5}$—$CH_3$, —$(CH_2)_{4}$—$CH_3$, —$(CH_2)_{2}$-Ph, —$(CH_2)_{3}$-Ph, —$(CH_2)_{4}$-Ph, —$(CH_2)_{5}$-Ph, —$(CH_2)_{6}$-Ph, —$(CH_2)_{7}$-Ph, —$(CH_2)_{8}$-Ph, and —$(CH_2)_{9}$-Ph.

11. The conjugate according to claim 4, wherein -$L^1$- and -$L^3$- are independently of each other selected from: —$CH_2$—, —$C_2H_4$—, —$C_3H_6$—, —$C_4H_8$—, —$C_5H_{10}$— and —$C_6H_{12}$—.

12. The conjugate according to claim 2, wherein $R^3$ is —H and $R^4$ is —OH.

13. The conjugate according to claim 2, wherein $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_{9}$—$CH_3$, —$(CH_2)_{8}$—$CH_3$,

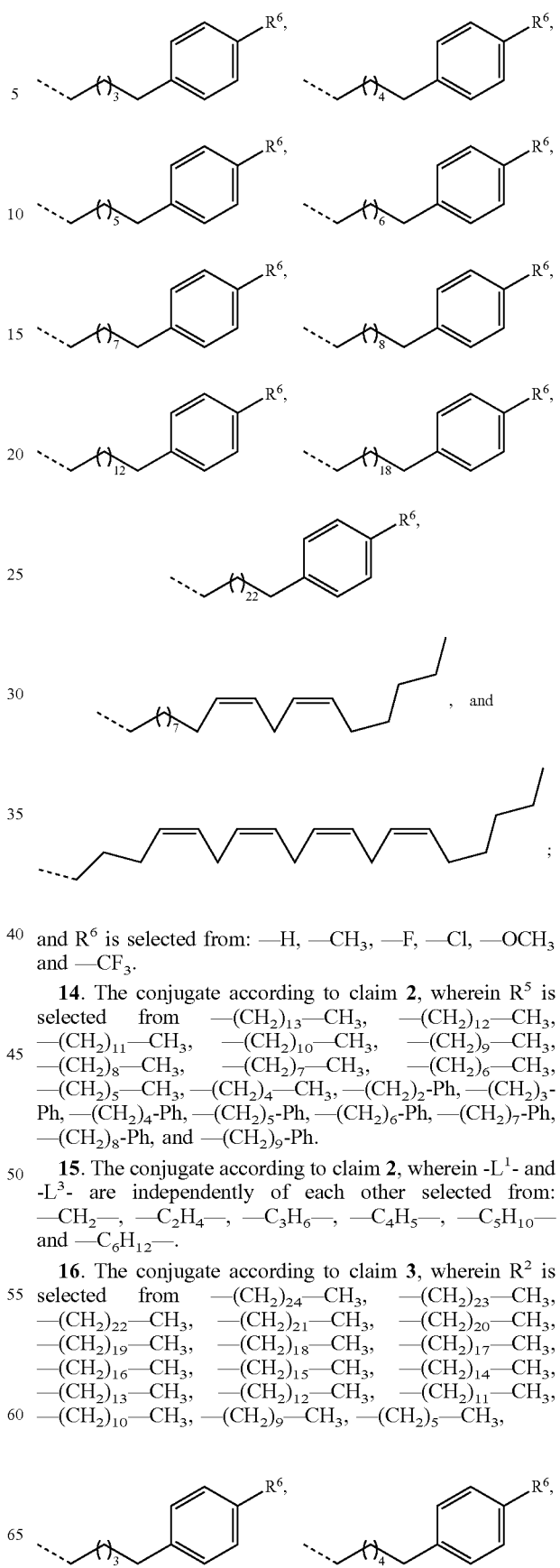

and $R^6$ is selected from: —H, —$CH_3$, —F, —Cl, —$OCH_3$ and —$CF_3$.

14. The conjugate according to claim 2, wherein $R^5$ is selected from —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_{9}$—$CH_3$, —$(CH_2)_{8}$—$CH_3$, —$(CH_2)_{7}$—$CH_3$, —$(CH_2)_{6}$—$CH_3$, —$(CH_2)_{5}$—$CH_3$, —$(CH_2)_{4}$—$CH_3$, —$(CH_2)_{2}$-Ph, —$(CH_2)_{3}$-Ph, —$(CH_2)_{4}$-Ph, —$(CH_2)_{5}$-Ph, —$(CH_2)_{6}$-Ph, —$(CH_2)_{7}$-Ph, —$(CH_2)_{8}$-Ph, and —$(CH_2)_{9}$-Ph.

15. The conjugate according to claim 2, wherein -$L^1$- and -$L^3$- are independently of each other selected from: —$CH_2$—, —$C_2H_4$—, —$C_3H_6$—, —$C_4H_8$—, —$C_5H_{10}$— and —$C_6H_{12}$—.

16. The conjugate according to claim 3, wherein $R^2$ is selected from —$(CH_2)_{24}$—$CH_3$, —$(CH_2)_{23}$—$CH_3$, —$(CH_2)_{22}$—$CH_3$, —$(CH_2)_{21}$—$CH_3$, —$(CH_2)_{20}$—$CH_3$, —$(CH_2)_{19}$—$CH_3$, —$(CH_2)_{18}$—$CH_3$, —$(CH_2)_{17}$—$CH_3$, —$(CH_2)_{16}$—$CH_3$, —$(CH_2)_{15}$—$CH_3$, —$(CH_2)_{14}$—$CH_3$, —$(CH_2)_{13}$—$CH_3$, —$(CH_2)_{12}$—$CH_3$, —$(CH_2)_{11}$—$CH_3$, —$(CH_2)_{10}$—$CH_3$, —$(CH_2)_{9}$—$CH_3$, —$(CH_2)_{5}$—$CH_3$,

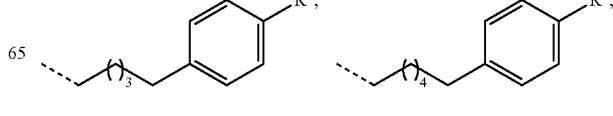

-continued

[chemical structures with R⁶ substituted phenyl groups on chains of length 5, 6, 7, 8, 12, 18, 22, and a polyunsaturated chain]

, and

[polyunsaturated chain structure]

;

and R⁶ is selected from: —H, —CH₃, —F, —Cl, —OCH₃ and —CF₃.

17. The conjugate according to claim 3, wherein $R^5$ is selected from —(CH₂)₁₃—CH₃, —(CH₂)₁₂—CH₃, —(CH₂)₁₁—CH₃, —(CH₂)₁₀—CH₃, —(CH₂)₉—CH₃, —(CH₂)₈—CH₃, —(CH₂)₇—CH₃, —(CH₂)₆—CH₃, —(CH₂)₅—CH₃, —(CH₂)₄—CH₃, —(CH₂)₂-Ph, —(CH₂)₃-Ph, —(CH₂)₄-Ph, —(CH₂)₅-Ph, —(CH₂)₆-Ph, —(CH₂)₇-Ph, —(CH₂)₈-Ph, and —(CH₂)₉-Ph.

18. The conjugate according to claim 3, wherein -L¹- and -L³- are independently of each other selected from: —CH₂—, —C₂H₄—, —C₃H₆—, —C₄H₈—, —C₅H₁₀— and —C₆H₁₂—.

* * * * *